(12) United States Patent
Cai et al.

(10) Patent No.: US 10,214,514 B2
(45) Date of Patent: Feb. 26, 2019

(54) HEDGEHOG ANTAGONISTS HAVING ZINC BINDING MOIETIES

(71) Applicants: Curis, Inc., Lexington, MA (US); GENENTECH, INC., South San Francisco, CA (US)

(72) Inventors: Xiong Cai, Bedford, MA (US); Changgeng Qian, Wayland, MA (US); Haixiao Zhai, Bedford, MA (US)

(73) Assignees: Curis, Inc., Lexington, MA (US); Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/629,081

(22) Filed: Jun. 21, 2017

(65) Prior Publication Data

US 2017/0349573 A1    Dec. 7, 2017

Related U.S. Application Data

(60) Division of application No. 13/932,395, filed on Jul. 1, 2013, now Pat. No. 9,708,299, which is a continuation of application No. PCT/US2012/020092, filed on Jan. 3, 2012.

(60) Provisional application No. 61/564,549, filed on Nov. 29, 2011, provisional application No. 61/429,350, filed on Jan. 3, 2011.

(51) Int. Cl.
| | | |
|---|---|---|
| *C07D 401/14* | (2006.01) | |
| *C07D 401/12* | (2006.01) | |
| *C07D 239/26* | (2006.01) | |
| *C07D 213/16* | (2006.01) | |
| *C07D 235/18* | (2006.01) | |
| *C07D 403/12* | (2006.01) | |
| *C07D 213/56* | (2006.01) | |
| *C07D 239/42* | (2006.01) | |
| *C07D 213/82* | (2006.01) | |

(52) U.S. Cl.
CPC ......... *C07D 403/12* (2013.01); *C07D 213/16* (2013.01); *C07D 213/56* (2013.01); *C07D 213/82* (2013.01); *C07D 235/18* (2013.01); *C07D 239/42* (2013.01); *C07D 401/12* (2013.01); *C07D 401/14* (2013.01)

(58) Field of Classification Search
CPC .. C07D 401/14; C07D 401/12; C07D 239/26; C07D 213/16; C07D 235/18
See application file for complete search history.

(56) References Cited

U.S. PATENT DOCUMENTS

2005/0209278 A1* 9/2005 McDonald .......... C07D 211/66
514/317

FOREIGN PATENT DOCUMENTS

WO    03/066579 A2    8/2003

* cited by examiner

*Primary Examiner* — Samira J Jean-Louis
(74) *Attorney, Agent, or Firm* — Elmore Patent Law Group, P.C.; Edgar Harlan; Carolyn Elmore

(57) ABSTRACT

The present invention provides compounds which antagonize hedgehog signaling and inhibit HDAC activity. The compounds can be used in methods of treating proliferative diseases and disorders such as cancer.

9 Claims, No Drawings

HEDGEHOG ANTAGONISTS HAVING ZINC BINDING MOIETIES

RELATED APPLICATIONS

This application is a divisional of U.S. application Ser. No. 13/932,395, filed on Jul. 1, 2013, which is a continuation of International Application No. PCT/US2012/020092, which designated the United States and was filed on Jan. 3, 2012, published in English, which claims the benefit of U.S. Provisional Application No. 61/429,350, filed on Jan. 3, 2011 and U.S. Provisional Application No. 61/564,549, filed on Nov. 29, 2011. The entire teachings of the above applications are incorporated herein by reference.

BACKGROUND OF THE INVENTION

Hedgehog (Hh) protein was first identified in *Drosophila melanogaster* as a segment-polarity gene involved in embryo patterning (Nusslein-Voihard et al., Roux. Arch. Dev. Biol., 193: 267-282 (1984)). Three orthologs of *Drosophila* hedgehog (Sonic, Desert and Indian) were later found to occur in all vertebrates, including fish, birds and mammals. Desert hedgehog (DHh) is expressed principally in the testes, both in mouse embryonic development and in the adult rodent and human; Indian hedgehog (IHh) is involved in bone development during embryogenesis and in bone formation in the adult; and, Sonic hedgehog (SHh) is expressed at high levels in the notochord and floor plate of developing vertebrate embryos. In vitro explant assays as well as ectopic expression of SHh in transgenic animals have shown that SHh plays a key role in neuronal tube patterning (Echelard et al., Cell, 75:1417-1430 (1993); Ericson et al., Cell, 81: 747-56 (1995); Marti et al., Nature, 375: 322-5 (1995); Krauss et al., Cell, 75: 1432-44 (1993); Riddle et al., Cell, 75: 1401-16 (1993); Roelink et al., Cell, 81: 445-55 (1995); Hynes et al., Neuron, 19: 15-26 (1997)). Hh also plays a role in the development of limbs (Krauss et al., Cell, 75: 143-144 (1993); Laufer et al., Cell, 79: 993-1003 (1994)), somites (Fan and Tessier-Lavigne, Cell, 79: 1175-86 (1994); Johnson et al., Cell, 79: 1165-73 (1994)), lungs (Bellusci et al., Develop., 124: 53-63 (1997) and skin (Oro et al., Science, 276: 817-21 (1997)).

Likewise, IHh and DHh are involved in bone, gut and germinal cell development (Apelqvist et al., Curr. Biol., 7: 80 1-4 (1997); Bellusci et al., Development, 124: 53-63 (1997); Bitgood et al., Curr. Biol., 6: 298-304 (1996); Roberts et al., Development, 121: 3163-74 (1995)).

Human SHh is synthesized as a 45 kDa precursor protein which is autocatalytically cleaved to yield a 20 kDa N-terminal fragment that is responsible for normal hedgehog signaling activity; and a 25 kDa C-terminal fragment that is responsible for autoprocessing activity in which the N-terminal fragment is conjugated to a cholesterol moiety (Lee, J. J., et al. (1994) Science, 266: 1528-1536; Bumcrot, D. A., et al. (1995), Mol. Cell Biol., 15: 2294-2303; Porter, J. A., et al. (1995) Nature, 374: 363-366). The N-terminal fragment consists of amino acid residues 24-197 of the full-length precursor sequence which remains membrane-associated through the cholesterol at its C-terminus (Porter, J. A., et al. (1996) Science, 274: 255-258; Porter, J. A., et al. (1995) Cell, 86(2): 1-34). Cholesterol conjugation is responsible for the tissue localization of the hedgehog signal.

At the cell surface, the Hh signal is thought to be relayed by the 12 transmembrane domain protein Patched (Ptc) (Hooper and Scott, Cell, 59: 751-65 (1989); Nakano et al., Nature, 341: 508-13 (1989)) and the G-protein-coupled-like receptor Smoothened (Smo) (Alcedo et al., Cell, 86(22): 1-232 (1996); van den Heuvel and Ingham, Nature, 382: 547-551 (1996)). Both genetic and biochemical evidence support a receptor model where Ptc and Smo are part of a multicomponent receptor complex (Chen and Struhl, Cell, 87: 553-63 (1996); Marigo et al., Nature, 384: 176-9 (1996); Stone et al., Nature, 384: 129-34 (1996)). Upon binding of Hh to Ptc, the normal inhibitory effect of Ptc on Smo is relieved, allowing Smo to transduce the Hh signal across the plasma membrane. However, the exact mechanism by which Ptc controls Smo activity has yet to be clarified.

The signaling cascade initiated by Smo results in activation of Gli transcription factors that translocate into the nucleus where they control transcription of target genes. Gli has been shown to influence transcription of Hh pathway inhibitors such as Ptc and Hip 1 in a negative feedback loop indicating that tight control of Hh pathway activity is required for proper cellular differentiation and organ formation.

Hedgehog pathway signaling has been implicated in tumorigenesis when reactivated in adult tissues through sporadic mutations or other mechanisms. Three mechanisms have been proposed for the Hedgehog pathway's involvement in cancer: Type 1 cancers are caused by loss-of-function mutations in Patched 1 ($PTCH_1$) or gain-of-function mutations in Smoothened (SMOH) lead to constitutive Hedgehog (Hh) pathway activation. Type 2 cancers rely on an autocrine model in which tumor cells themselves produce and respond to Hh ligand. Type 3 is a paracrine model in which tumor cells produce Hh ligand and surrounding stromal cells respond by producing additional growth factors to support tumor growth or survival, for example, IGF (Insulin-Like Growth Factor) and VEGF (Vascular Endothelial Growth Factor) (Rubin, L. L. and de Sauvage, F. J. Nature Rev. Drug Discovery, 5: 1026-1033 (2006)).

Dysfunctional Ptc gene mutations have also been associated with a large percentage of sporadic basal cell carcinoma tumors (Chidambaram et al., Cancer Research, 56: 4599-601 (1996); Gailani et al., Nature Genet., 14: 78-81 (1996); Haim et al., Cell, 85: 841-51 (1996); Jolmson et al., Science, 272: 1668-71 (1996); Unden et al., Cancer Res., 56: 4562-5; Wicking et al., Am. J. Hum. Genet., 60: 21-6 (1997)). Loss of Ptc function is thought to cause an uncontrolled Smo signaling in basal cell carcinoma. Similarly, activating Smo mutations have been identified in sporadic BCC tumors (Xie et al., Nature, 391: 90-2 (1998)), emphasizing the role of Smo as the signaling subunit in the receptor complex for SHh.

The development of resistance to Shh pathway inhibitors has been observed in animal tumor models (Buonamici, S. et al., Science Trans. Med., 2010, 2: 51ra70; Osherovich, L. SciBX 2010, 3(40)) and in humans (Yauch, R. et al, Science, 2009). Several mechanisms for resistance were identified, including SMO mutations, Gli2 amplification and upregulation of the IGF-1R-PI3K signaling pathway.

Various inhibitors of hedgehog signaling have been investigated. The first Hedgehog signaling inhibitor to be discovered was cyclopamine, a natural alkaloid that has been shown to arrest cell cycle at GO-Gl and to induce apoptosis in SCLC. A number of synthetic small molecule Hedgehog pathway inhibitors are currently under development (Trembley, M. R. et al., Expert Opin. Ther. Patents, 19(8):1039-56 (2009)). Despite advances with these and other compounds, there remains a need for potent inhibitors of the hedgehog signaling pathway.

Histone acetylation is a reversible modification, with deacetylation being catalyzed by a family of enzymes termed histone deacetylases (HDACs). HDAC's are represented by 18 genes in humans and are divided into four distinct classes (J. Mol Biol, 2004, 338(1): 17-31). In mammalians class I HDAC's (HDAC1-3, and HDAC8) are related to yeast RPD3 HDAC, class 2 HDAC's (HDAC4-7, HDAC9 and HDAC10) are related to yeast HDAC1, class 4 (HDAC11), and class 3 HDAC's (a distinct class encompassing the sirtuins) are related to yeast Sir2.

Csordas (Biochem. J., 1990, 286: 23-38) teaches that histones are subject to post-translational acetylation of the ε-amino groups of N-terminal lysine residues, a reaction that is catalyzed by histone acetyl transferase (HAT1). Acetylation neutralizes the positive charge of the lysine side chain, and is thought to impact chromatin structure. Indeed, access of transcription factors to chromatin templates is enhanced by histone hyperacetylation, and enrichment in underacetylated histone H4 has been found in transcriptionally silent regions of the genome (Taunton et al., Science, 1996, 272:408-411). In the case of tumor suppressor genes, transcriptional silencing due to histone modification can lead to oncogenic transformation and cancer.

Several classes of HDAC inhibitors currently are marketed or under evaluation in clinical trials. Examples include the hydroxamic acid derivatives suberoylanilide hydroxamic acid (SAHA) and Romidepsin, which are marketed, and PXD101, LH-589 and LAQ824, which are currently in clinical development. In the benzamide class of HDAC inhibitors, MS-275, MGCD$_{0103}$ and CI-994 are currently being investigated in clinical trials. Mourne et al. (Abstract #4725, AACR 2005), demonstrate that thiophenyl modification of benzamides significantly enhances HDAC inhibitory activity against HDAC1.

In addition, recent studies have shown that the acetylation of Gli proteins functions as a key transcriptional checkpoint of Hedgehog signaling. It was found that an autoregulatory loop exists whereby Shh increases HDAC1 levels and HDAC1 in turn enhances Hh-induced signal activation by deacetylation of Gli1 and Gli2. Moreover, inhibitors of class 1 HDACs suppress Gli1 and Gli2 activation, thus suppressing Hh-dependent growth of neural progenitors and tumor cells. (Canettieri, G. et al., Nature Cell Biology, 2010, 12: 132-142).

Certain cancers have been effectively treated with agents targeting multiple signaling pathways. A recent study demonstrated that the combined targeting of HDACs and Hh signaling enhanced cytotoxicity in pancreatic adenocarcinoma. (Chun, S. et al., Cancer Biol. & Therapy, 2009, 8(14): 1328-1339). However, treatment regimes using a cocktail of cytotoxic drugs often are limited by dose limiting toxicities and drug-drug interactions. More recent advances with molecularly targeted drugs have provided some new approaches to combination treatment for cancer, allowing multiple targeted agents to be used simultaneously, or combining these new therapies with standard chemotherapeutics or radiation to improve outcome without reaching dose limiting toxicities. However, in many cases, dose-limiting toxicities are reached before pharmacologically meaningful levels of exposure are achieved, and the ability to use such combinations currently is limited to drugs that show compatible pharmacokinetic and pharmacodynamic properties. In addition, the regulatory requirements to demonstrate safety and efficacy of combination therapies can be more costly and lengthy than corresponding single agent trials. Once approved, combination strategies may also be associated with increased costs to patients, as well as decreased patient compliance.

SUMMARY OF THE INVENTION

The present invention relates to hedgehog antagonist compounds having zinc-binding moieties and their use in the treatment of hedgehog and HDAC related diseases and disorders such as cancer and other diseases and disorders characterized by uncontrolled cell proliferation. The compounds of the present invention act as HDAC inhibitors by virtue of their ability to bind zinc ions and as inhibitors of the Hedgehog signaling pathway. Combining hedgehog antagonism and HDAC inhibition into a single molecule may provide a synergistic effect in therapeutic applications, and in particular, to the treatment of cancer.

Accordingly, one aspect of the present invention provides a compound of Formula (I) or Formula (II):

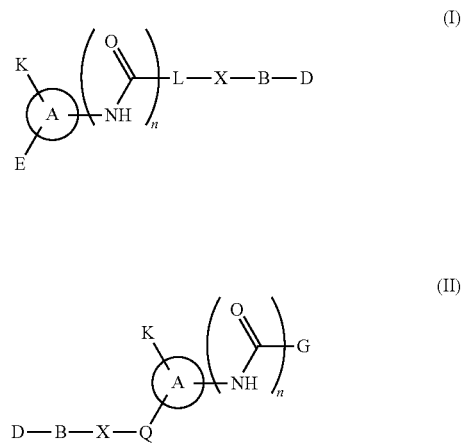

or a geometric isomer, enantiomer, diastereomer, racemate, pharmaceutically acceptable salt or prodrug thereof;

wherein:

Ring A is an aromatic, saturated or partially unsaturated carbocycle; preferably a monocyclic, bicyclic or polycyclic $C_3$-$C_{12}$-carbocycle;

E is substituted or unsubstituted aryl or substituted or unsubstituted heteroaryl or substituted or unsubstituted saturated or partially unsaturated heterocyclyl;

L is substituted or unsubstituted aryl or substituted or unsubstituted heteroaryl or substituted or unsubstituted saturated or partially unsaturated heterocyclyl;

Q is substituted or unsubstituted aryl; substituted or unsubstituted heteroaryl or substituted or unsubstituted saturated or partially unsaturated heterocyclyl;

G is substituted or unsubstituted aryl, substituted or unsubstituted heteroaryl or substituted or unsubstituted saturated or partially unsaturated heterocyclyl;

K is halogen, preferably Cl;

X is absent, —O—, —N(R$_2$)—, —S—, —S(O)—, —S(O)$_2$—, —C(O)—, —C(O)O—, —OC(O)—, —C(O)N(R$_2$)—, —N(R$_2$)C(O)—, —S(O)$_2$N(R$_2$)—, or —N(R$_2$)S(O)$_2$—;

R$_2$ is hydrogen or aliphatic, preferably hydrogen or C$_1$-C$_6$-alkyl, and more preferably hydrogen or methyl;

n is 0 or 1;
B is a bond or a linker; and
D is selected from:
(a)

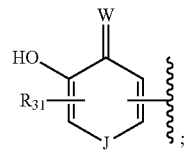

where W is O or S; J is O, NH or NCH$_3$; and R$_{31}$ is hydrogen or lower alkyl;
(b)

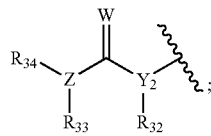

where W is O or S; Y$_2$ is absent, N, or CH; Z is N or CH; R$_{32}$ and R$_{34}$ are independently hydrogen, OR', aliphatic group, provided that if R$_{32}$ and R$_{34}$ are both present, one of R$_{32}$ or R$_{34}$ must be OR' and if Y$_2$ is absent, R$_{34}$ must be OR'; R$_{33}$ is hydrogen or aliphatic group; and R' is hydrogen, aliphatic or acyl, preferably hydrogen; preferably Y$_2$ and R$_{32}$ are absent, Z is N, R$_{34}$ is hydroxy and R$_{33}$ is hydrogen;
(c)

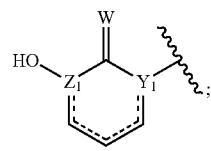

where W is O or S; Y$_1$ and Z$_1$ are independently N, C or CH; and
(d)

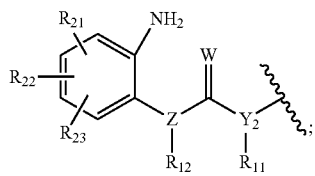

where Z, Y$_2$, and W are as previously defined; R$_{11}$ and R$_{12}$ are independently selected from hydrogen or aliphatic; R$_{21}$, R$_{22}$ and R$_{23}$ are independently selected from hydrogen, hydroxy, amino, halogen, alkoxy, alkylamino, dialkylamino, CF$_3$, CN, NO$_2$, sulfonyl, acyl, aliphatic, substituted aliphatic, aryl, substituted aryl, heteroaryl, substituted heteroaryl, heterocyclic, and substituted heterocyclic.

Another aspect of the invention provides methods of inhibiting hedgehog signaling activity in a cell, by contacting the cell with an effective hedgehog inhibitory amount of a compound of Formula I or Formula II, or a stereoisomer, geometric isomer, tautomer, solvate, metabolite, or pharmaceutically acceptable salt or prodrug thereof.

Another aspect of the invention provides methods of inhibiting HDAC activity in a cell, by contacting the cell with an effective HDAC inhibitory amount of a compound of Formula I or Formula II, or a stereoisomer, geometric isomer, tautomer, solvate, metabolite, or pharmaceutically acceptable salt or prodrug thereof.

DETAILED DESCRIPTION OF THE INVENTION

In one embodiment, the present invention provides compounds which are represented by Formula III or Formula IV:

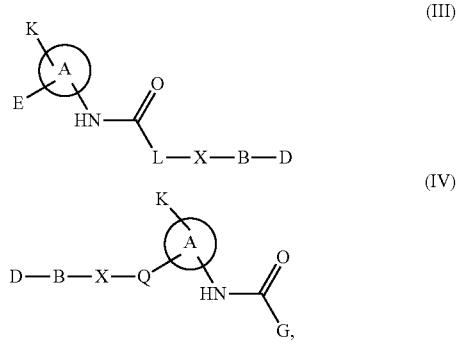

where Ring A, K, G, Q, X, B, D, L and E have the meanings given above.

In another embodiment, the compounds of the invention are represented by Formula V or VI:

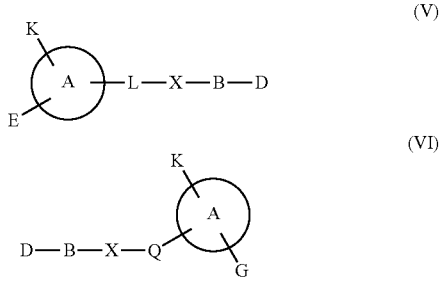

and stereoisomers, geometric isomers, tautomers, pharmaceutically acceptable salts and prodrugs thereof, wherein E, K, L, X, B, G, Q and D have the meanings given above.

In an embodiment, the compounds of the invention are represented by Formula VII or VIII:

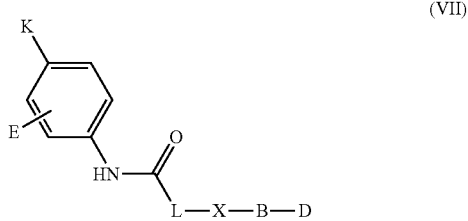

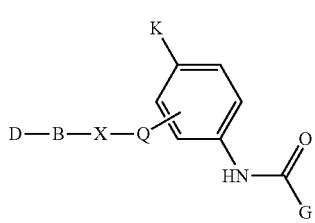

(VIII)

and stereoisomers, geometric isomers, tautomers, pharmaceutically acceptable salts and prodrugs thereof, wherein E, K, L, X, B, G, Q and D have the meanings given above. Preferably, G and L are each independently substituted or unsubstituted aryl or substituted or unsubstituted heteroaryl, and more preferably G and L are each independently substituted or unsubstituted phenyl or substituted or unsubstituted pyridyl. Preferably, E and Q are each independently substituted or unsubstituted heteroaryl.

In an embodiment, the compounds of the invention are represented by Formula IX or X:

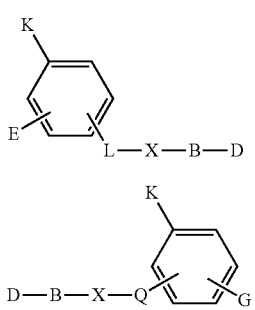

(IX)

(X)

and stereoisomers, geometric isomers, tautomers, pharmaceutically acceptable salts and prodrugs thereof, wherein E, K, L, X, B, G, Q and D have the meanings given above. Preferably, G and L are each independently heterocyclyl, preferably heterocycloalkyl.

In one embodiment, the present invention provides compounds which are represented by Formula XI:

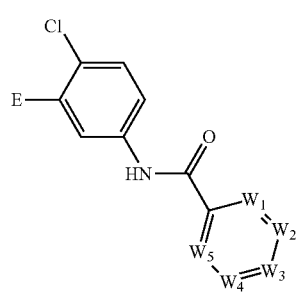

(XI)

and stereoisomers, geometric isomers, tautomers, pharmaceutically acceptable salts and prodrugs thereof;
wherein:
one of $W_1$-$W_5$ is C(X—B-D) and the others are each independently N or $CR_3$, provided that no more than three of $W_1$-$W_5$ are N;
each $R_3$ is independently selected from hydrogen, hydroxy, amino, halogen, alkoxy, alkylamino, dialkylamino, $CF_3$, CN, $NO_2$, sulfonyl, acyl, aliphatic, substituted aliphatic, aryl, substituted aryl, heteroaryl, substituted heteroaryl, heterocyclic, and substituted heterocyclic; and X, B and D have the meanings given for these variables above.

In preferred embodiments of the compounds of Formula XI, E is substituted or unsubstituted pyridyl, such as substituted or unsubstituted pyrid-2-yl, pyrid-3-yl or pyrid-4-yl, or substituted or unsubstituted benzimidazolyl, such as substituted or unsubstituted benzimidazol-2-yl. In particularly preferred embodiments, E is selected from the groups set forth below:

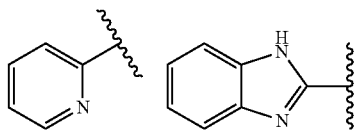

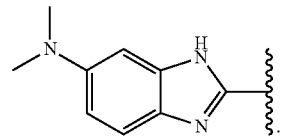

In another preferred embodiment of the compounds of Formula XI, the group

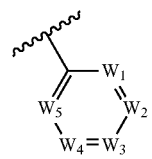

is selected from the groups shown below:

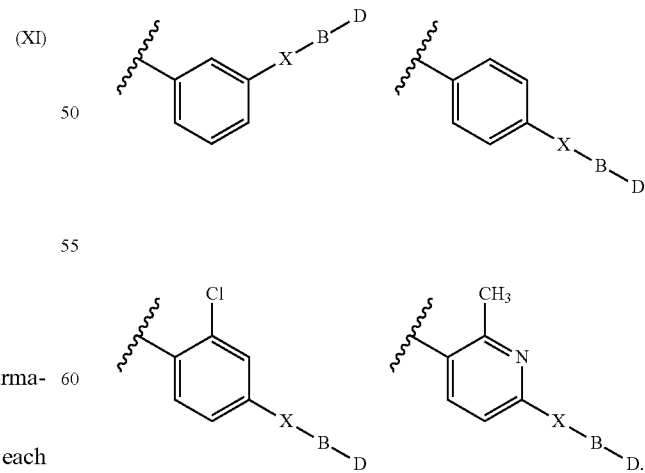

In another embodiment, the present invention provides compounds which are represented by Formula XII:

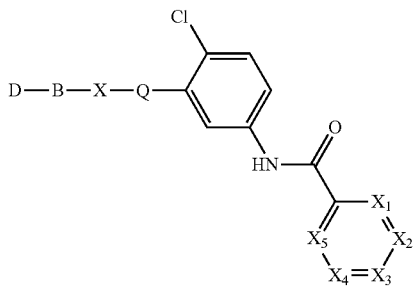

(XII)

and stereoisomers, geometric isomers, tautomers, pharmaceutically acceptable salts and prodrugs thereof; wherein:

$X_1$-$X_5$ are each independently selected from N and $CR_3$, provided that at least two of $X_1$-$X_5$ are $CR_3$; and Q, D, B, X and $R_3$ have the meanings given for these variables above.

In preferred embodiments of the compounds of Formula XII, Q is substituted or unsubstituted pyridyl, substituted or unsubstituted pyrimidyl or substituted or unsubstituted benzimidazolyl. In particularly preferred embodiments, Q is selected from the groups below,

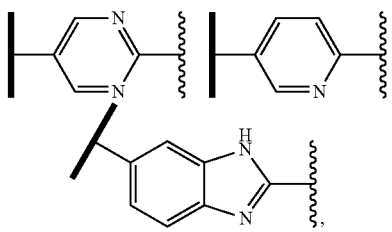

wherein the bond to the benzene ring is denoted by , and the bond to X is denoted by .

In other preferred embodiments of the compounds of Formula XII, the group

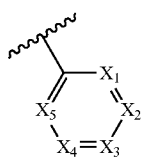

is substituted or unsubstituted phenyl, substituted or unsubstituted pyridyl, such as substituted or unsubstituted pyrid-2-yl, pyrid-3-yl or pyrid-4-yl, or substituted or unsubstituted pyrimidyl, such as pyrimid-2-yl, pyrimid-4-yl or pyrimid-5-yl. In particularly preferred embodiments, this group is selected from those set forth below:

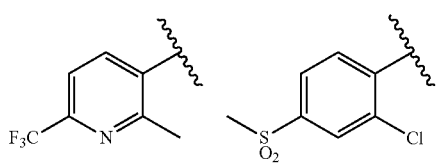

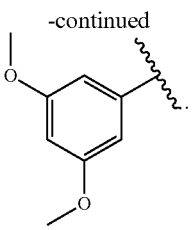

In a preferred embodiment, the bivalent B is a direct bond or straight- or branched-, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, or alkynylheteroaryl, in which groups one or more methylenes can be interrupted or terminated by O, S, S(O), $SO_2$, $N(R_2)$, C(O), substituted or unsubstituted aryl, substituted or unsubstituted heteroaryl, or substituted or unsubstituted heterocyclic; such divalent B linkers include but are not limited to alkyl, alkenyl, alkynyl, alkylaryl, alkenylaryl, alkynylaryl, alkylheterocyclyaryl, alkylheterocyclylarylalkyl, alkylheterocyclylheteroaryl, alkylheterocyclylheteroarylalkyl, alkoxyaryl, alkylaminoaryl, alkoxyalkyl, alkylaminoalkyl, alkylheterocycloalkyl, alkylheteroarylalkyl, alkylamino, aryl, heteroaryl, heterocyclyl, $N(R_2)$alkenyl, $N(R_2)$alkynyl, $N(R_2)$alkoxyalkyl, $N(R_2)$alkylaminoalkyl, $N(R_2)$alkylaminocarbonyl, $N(R_2)$alkylaryl, $N(R_2)$alkenylaryl, $N(R_2)$alkynylaryl, $N(R_2)$alkoxyaryl, $N(R_2)$alkylaminoaryl, $N(R_2)$cycloalkyl, $N(R_2)$aryl, $N(R_2)$heteroaryl, $N(R_2)$heterocycloalkyl, $N(R_2)$alkylheterocycloalkyl, alkoxy, O-alkenyl, O-alkynyl, O-alkoxyalkyl, O-alkylaminoalkyl, O-alkylaminocarbonyl, O-alkylaryl, O-alkenylaryl, O-alkynylaryl, O-alkoxyaryl, O-alkylaminoaryl, O-cycloalkyl, O-aryl, O-heteroaryl, O-heterocycloalkyl, O-alkylheterocycloalkyl, C(O)alkyl, C(O)-alkenyl, C(O)alkynyl, C(O)alkylaryl, C(O)alkenylaryl, C(O)alkynylaryl, C(O)alkoxyalkyl, C(O)alkylaminoalkyl, C(O)alkylaminocarbonyl, C(O)cycloalkyl, C(O)aryl, C(O)heteroaryl, C(O)heterocycloalkyl, $CON(R_2)$, $CON(R_2)$alkyl, $CON(R_2)$alkenyl, $CON(R_2)$alkynyl, $CON(R_2)$alkylaryl, $CON(R_2)$alkenylaryl, $CON(R_2)$alkynylaryl, $CON(R_2)$alkoxyalkyl, $CON(R_2)$alkylaminoalkyl, $CON(R_2)$alkylaminocarbonyl, $CON(R_2)$alkoxyaryl, $CON(R_2)$alkylaminoaryl, $CON(R_2)$cycloalkyl, $CON(R_2)$aryl, $CON(R_2)$heteroaryl, $CON(R_2)$heterocycloalkyl, $CON(R_2)$alkylheterocycloalkyl, $N(R_2)C(O)$alkyl, $N(R_2)C(O)$alkenyl, $N(R_2)C(O)$— alkynyl, $N(R_2)C(O)$alkylaryl, $N(R_2)C(O)$alkenylaryl, $N(R_2)C(O)$alkynylaryl, $N(R_2)C(O)$alkoxyalkyl, $N(R_2)C(O)$alkylaminoalkyl, $N(R_2)C(O)$alkylaminocarbonyl, $N(R_2)C(O)$alkoxyaryl, $N(R_2)C(O)$alkylaminoaryl, $N(R_2)C(O)$cycloalkyl, $N(R_2)C(O)$aryl, $N(R_2)C(O)$heteroaryl, $N(R_2)C(O)$heterocycloalkyl, $N(R_2)C(O)$alkylheterocycloalkyl, NHC(O)NH, NHC(O)NH-alkyl, NHC(O)NH-alkenyl, NHC(O)NH-alkynyl, NHC(O)NH-alkylaryl, NHC(O)NH-alkenylaryl, NHC(O)NH-alkynylaryl, NHC(O)NH-alkoxyaryl, NHC(O)NH-alkylaminoaryl, NHC(O)NH-cycloalkyl, NHC(O)NH-aryl, NHC(O)NH-heteroaryl, NHC(O)NH-heterocycloalkyl, NHC(O)NH-alkylheterocycloalkyl, S-alkyl, S-alkenyl, S-alkynyl, S-alkoxyalkyl, S-alkylaminoalkyl, S-alkylaryl, S-alkylaminocarbonyl, S-alkylaryl, S-alkynylaryl, S-alkoxyaryl, S-alkylaminoaryl, S-cycloalkyl, S-aryl, S-heteroaryl, S-heterocycloalkyl, S-alkylheterocycloalkyl, S(O)alkyl, S(O)alkenyl, S(O)alkynyl, S(O)alkoxyalkyl, S(O)alkylaminoalkyl, S(O)alkylaminocarbonyl, S(O)alkylaryl, S(O)alkenylaryl, S(O)alkynylaryl, S(O)alkoxyaryl, S(O)alkylaminoaryl, S(O)cycloalkyl, S(O)aryl, S(O)heteroaryl, S(O)heterocycloalkyl, S(O)alkylheterocycloalkyl, $S(O)_2$alkyl, $S(O)_2$alkenyl, $S(O)_2$alkynyl, $S(O)_2$alkoxyalkyl, $S(O)_2$alkylaminoalkyl, $S(O)_2$alkylaminocarbonyl, $S(O)_2$alkylaryl, $S(O)_2$alkenylaryl, $S(O)_2$alkynylaryl, $S(O)_2$alkoxyaryl, $S(O)_2$alkylaminoaryl, $S(O)_2$cycloalkyl, $S(O)_2$aryl, $S(O)_2$heteroaryl, $S(O)_2$heterocycloalkyl, $S(O)_2$alkylheterocycloalkyl, $S(O)_2$heterocyclylalkyl, $S(O)_2$heterocyclylalkenyl, $S(O)_2$heterocyclylalkynyl, $SO_2NH$, $SO_2NH$-alkyl, $SO_2NH$-alkenyl, $SO_2NH$-alkynyl, $SO_2NH$-alkylaryl, $SO_2NH$-alkenylaryl, $SO_2NH$-alkynylaryl, $SO_2NH$-cycloalkyl, $SO_2NH$-aryl, $SO_2NH$-heteroaryl, $SO_2NH$-heterocycloalkyl, $SO_2NH$-alkylheterocycloalkyl, alkylaryloxyalkoxy, alkylaryloxyalkylamino, alkylarylaminoalkoxy, alkylarylaminoalkylamino, alkylarylalkylaminoalkoxy, alkylarylalkylaminoalkoxy, alkenylaryloxyalkoxy, alkenylaryloxyalkylamino, alkenylarylaminoalkoxy, alkenylarylaminoalkylamino, alkenylarylalkylaminoalkoxy, alkenylarylalkylaminoalkylamino.

In a more preferred embodiment, B is a straight chain alkyl, alkenyl, alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, or alkynylhereroaryl. In these linkers, one or more methylenes can be interrupted or terminated by —O—, —N($R_2$)—, —C(O)—, —C(O)N($R_2$)—, or —C(O)O—.

In one embodiment, the linker B is between 1-24 carbon atoms, preferably 4-24 carbon atoms, preferably 4-18 carbon atoms, more preferably 4-12 carbon atoms, and most preferably about 4-10 carbon atoms.

In a preferred embodiment, B is selected from straight chain $C_1$-$C_{10}$ alkyl, $C_1$-$C_{10}$ alkenyl, $C_1$-$C_{10}$ alkynyl, $C_1$-$C_{10}$ alkoxy, alkoxy$C_1$-$C_{10}$alkoxy, alkylamino, alkoxy$C_1$-$C_{10}$alkylamino, alkylcarbonylamino, $C_1$-$C_{10}$ alkylaminocarbonyl, aryloxy$C_1$-$C_{10}$alkoxy, aryloxy$C_1$-$C_{10}$alkylamino, aryloxy$C_1$-$C_{10}$alkylamino carbonyl, $C_1$-$C_{10}$-alkylamino-alkylaminocarbonyl, $C_1$-$C_{10}$ alkyl(N-alkyl)aminoalkyl-aminocarbonyl, alkylaminoalkylamino, alkylcarbonylaminoalkylamino, alkyl(N-alkyl)aminoalkylamino, (N-alkyl)alkylcarbonylaminoalkylamino, alkylaminoalkyl, alkylaminoalkylaminoalkyl, alkylpiperazinoalkyl, piperazinoalkyl, alkylpiperazino, alkenylaryloxy$C_1$-$C_{10}$alkoxy, alkenylarylamino$C_1$-$C_{10}$alkoxy, alkenylaryllalkylamino$C_1$-$C_{10}$alkoxy, alkenylaryloxy$C_1$-$C_{10}$alkylamino, alkenylaryloxy$C_1$-$C_{10}$alkylaminocarbonyl, piperazinoalkylaryl, heteroaryl$C_1$-$C_{10}$alkyl, heteroaryl$C_2$-$C_{10}$alkenyl, heteroaryl$C_2$-$C_{10}$alkynyl, heteroaryl$C_1$-$C_{10}$alkylamino, heteroaryl$C_1$-$C_{10}$alkoxy, heteroaryloxy$C_1$-$C_{10}$alkyl, heteroaryloxy$C_2$-$C_{10}$alkenyl, heteroaryloxy$C_2$-$C_{10}$alkynyl, heteroaryloxy$C_1$-$C_{10}$alkylamino, heteroaryloxy$C_1$-$C_{10}$alkoxy. In the most preferred embodiments, the D group is attached to B via an aliphatic moiety carbon chain, an aryl group or a heteroaryl group within B.

In another preferred embodiment, B is a direct bond, aryl, heteroaryl, $C_2$-$C_{10}$-alkyl, $C_2$-$C_{10}$-alkenyl, aryl-$C_2$-$C_{10}$-alkyl, aryl-$C_2$-$C_{10}$-alkenyl, aryloxy-$C_1$-$C_{10}$-alkyl, heterocyclylheteroaryl, $C_1$-$C_{10}$-alkylheterocyclylheteroaryl, or $C_1$-$C_{10}$-alkylaminoheteroaryl.

It is understood that alkyl, alkenyl, alkynyl, aryl, heteroaryl, cycloalkyl, heterocyclyl and the like can be further substituted.

In certain embodiments, the compounds of Formulas I and II are represented by Formulas XIII and XIV, respectively:

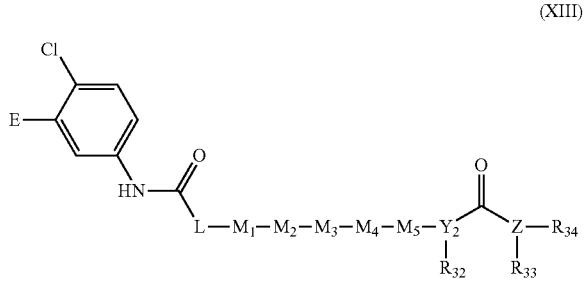

(XIII)

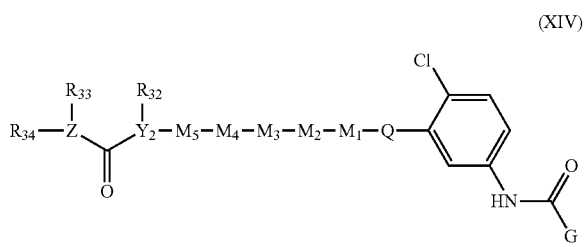

(XIV)

wherein $M_1$ is absent, O, S, $NR_2$, $C_1$-$C_6$ alkyl, $C_2$-$C_6$ alkenyl, $C_2$-$C_6$ alkynyl, aryl, heteroaryl, heterocyclic, SO, $SO_2$ or C=O; $M_2$ is absent, $C_1$-$C_6$ alkyl, O, $NR_2$-heterocyclic, aryl, heteroaryl, or C=O; $M_3$ is absent, O, $NR_2$, S, SO, $SO_2$, CO, $C_1$-$C_6$ alkyl, $C_2$-$C_6$ alkenyl, $C_2$-$C_6$ alkynyl, aryl, heteroaryl, or heterocyclic; $M_4$ is absent, O, $NR_2$, heteroaryl, heterocyclic or aryl; and $M_5$ is absent, $C_1$-$C_8$ alkyl, $C_2$-$C_8$ alkenyl, $C_2$-$C_5$alkynyl, heteroaryl, heterocyclic or aryl; and E, L, Q, G, Z, $Y_2$, $R_{32}$, $R_{33}$ and $R_{34}$ have the definitions given for these variables above. Preferably, $Y_2$ and $R_{32}$ are absent, Z is N, $R_{33}$ is H and $R_{34}$ is hydroxy.

Specific compounds of the invention are set forth in the Table below.

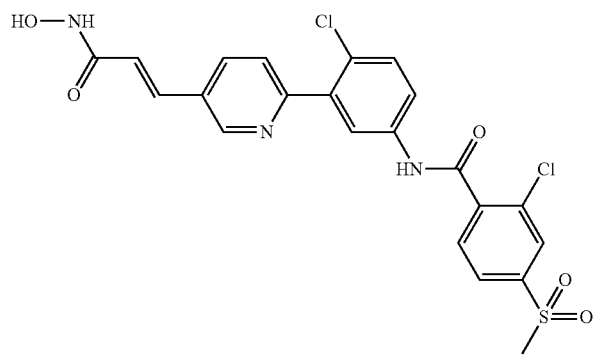 [SMILES: CS(=O)(=O)c1ccc(C(=O)Nc2ccc(Cl)c(-c3ccc(/C=C/C(=O)NO)cn3)c2)c(Cl)c1]
1
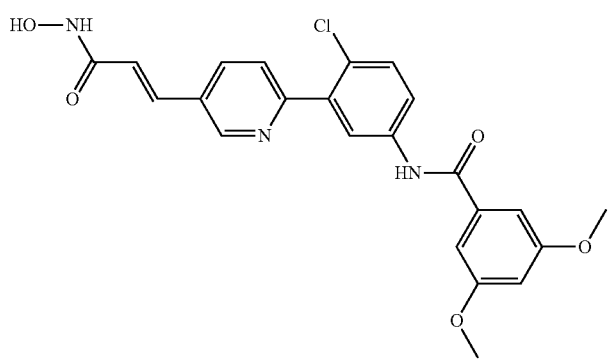 [SMILES: COc1cc(OC)cc(C(=O)Nc2ccc(Cl)c(-c3ccc(/C=C/C(=O)NO)cn3)c2)c1]
2
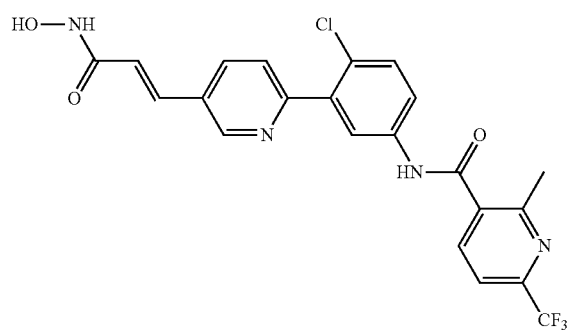 [SMILES: Cc1nc(C(F)(F)F)ccc1C(=O)Nc1ccc(Cl)c(-c2ccc(/C=C/C(=O)NO)cn2)c1]
3
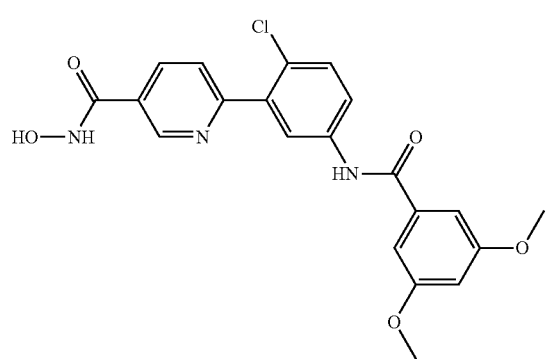 [SMILES: COc1cc(OC)cc(C(=O)Nc2ccc(Cl)c(-c3ccc(C(=O)NO)cn3)c2)c1]
4

-continued
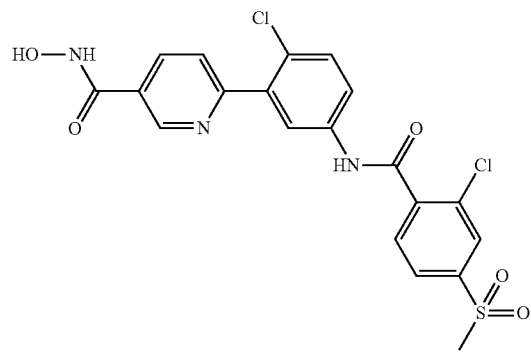 [SMILES: CS(=O)(=O)c1ccc(C(=O)Nc2ccc(Cl)c(-c3ccc(C(=O)NO)cn3)c2)c(Cl)c1]
5
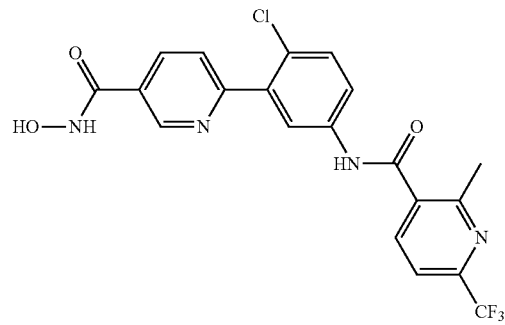 [SMILES: Cc1nc(C(F)(F)F)ccc1C(=O)Nc1ccc(Cl)c(-c2ccc(C(=O)NO)cn2)c1]
6
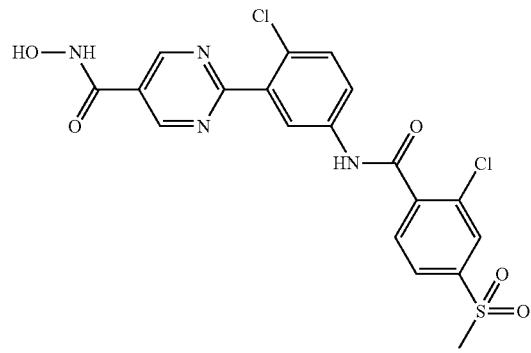 [SMILES: CS(=O)(=O)c1ccc(C(=O)Nc2ccc(Cl)c(-c3ncc(C(=O)NO)cn3)c2)c(Cl)c1]
7
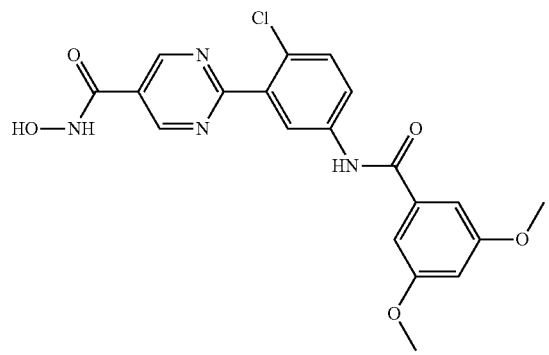 [SMILES: COc1cc(OC)cc(C(=O)Nc2ccc(Cl)c(-c3ncc(C(=O)NO)cn3)c2)c1]
8

-continued
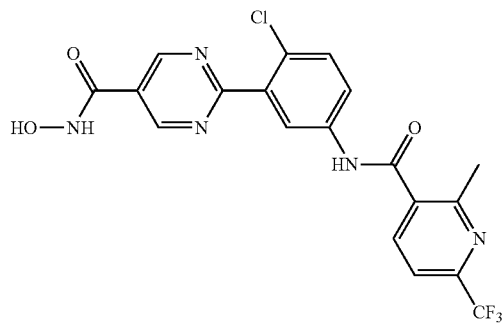 [SMILES: Cc1nc(C(F)(F)F)ccc1C(=O)Nc1ccc(Cl)c(-c2ncc(C(=O)NO)cn2)c1]
9
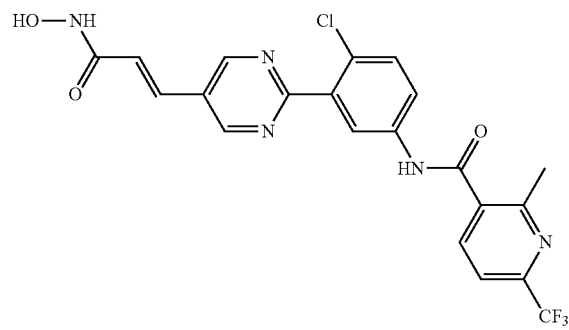
10
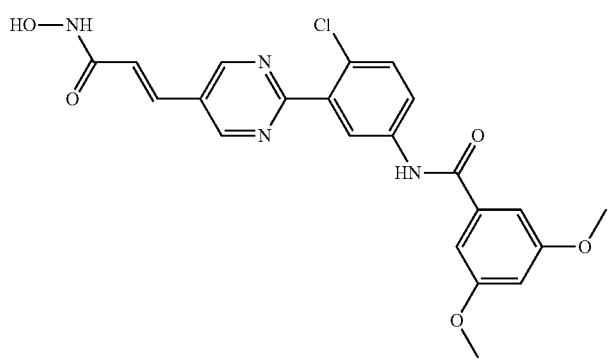 [SMILES: COc1cc(OC)cc(C(=O)Nc2ccc(Cl)c(-c3ncc(/C=C/C(=O)NO)cn3)c2)c1]
11
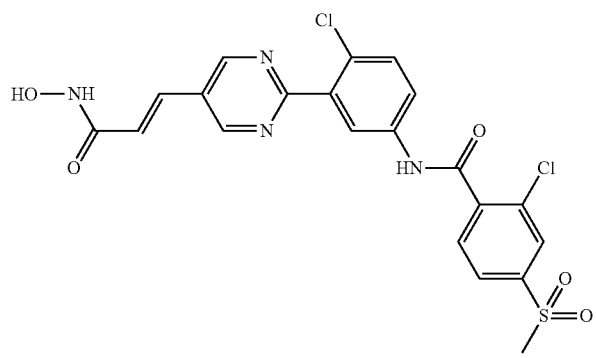 [SMILES: CS(=O)(=O)c1ccc(C(=O)Nc2ccc(Cl)c(-c3ncc(/C=C/C(=O)NO)cn3)c2)c(Cl)c1]
12

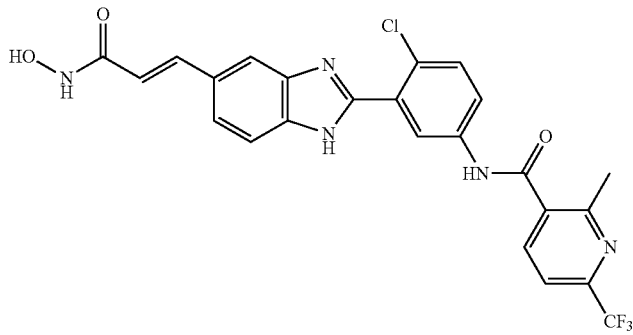 [SMILES: Cc1nc(C(F)(F)F)ccc1C(=O)Nc1ccc(Cl)c(-c2nc3cc(/C=C/C(=O)NO)ccc3[nH]2)c1]
13
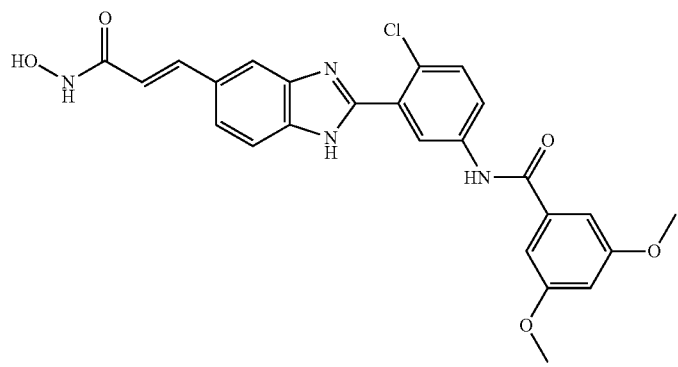 [SMILES: COc1cc(OC)cc(C(=O)Nc2ccc(Cl)c(-c3nc4cc(/C=C/C(=O)NO)ccc4[nH]3)c2)c1]
14
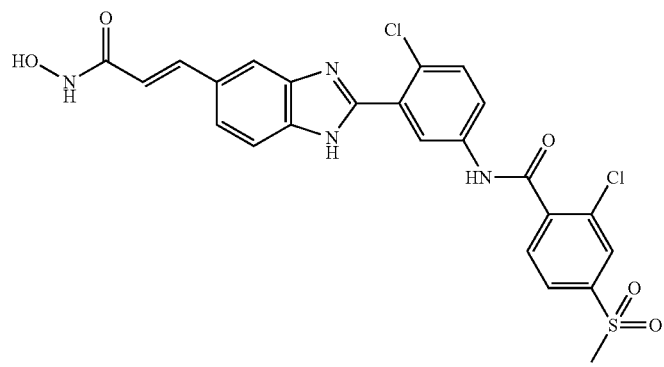 [SMILES: CS(=O)(=O)c1ccc(C(=O)Nc2ccc(Cl)c(-c3nc4cc(/C=C/C(=O)NO)ccc4[nH]3)c2)c(Cl)c1]
15
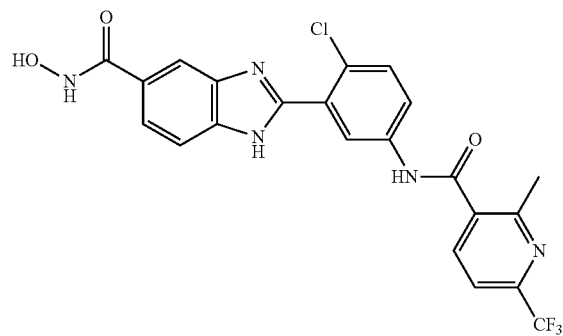 [SMILES: Cc1nc(C(F)(F)F)ccc1C(=O)Nc1ccc(Cl)c(-c2nc3cc(C(=O)NO)ccc3[nH]2)c1]
16

-continued
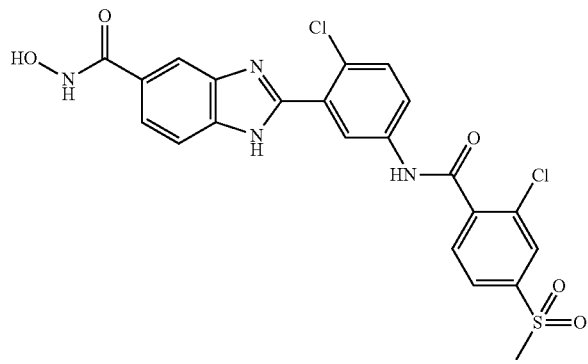 [SMILES: CS(=O)(=O)c1ccc(C(=O)Nc2ccc(Cl)c(-c3nc4cc(C(=O)NO)ccc4[nH]3)c2)c(Cl)c1]
17
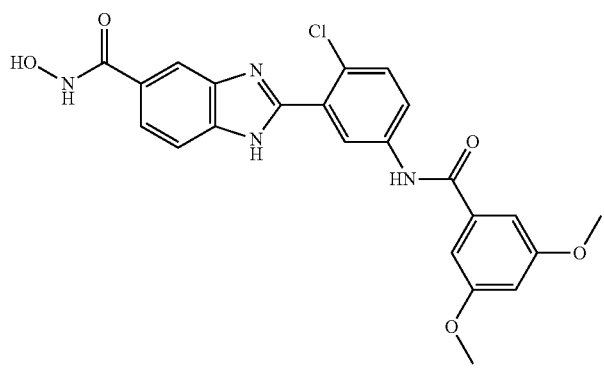 [SMILES: COc1cc(OC)cc(C(=O)Nc2ccc(Cl)c(-c3nc4cc(C(=O)NO)ccc4[nH]3)c2)c1]
18
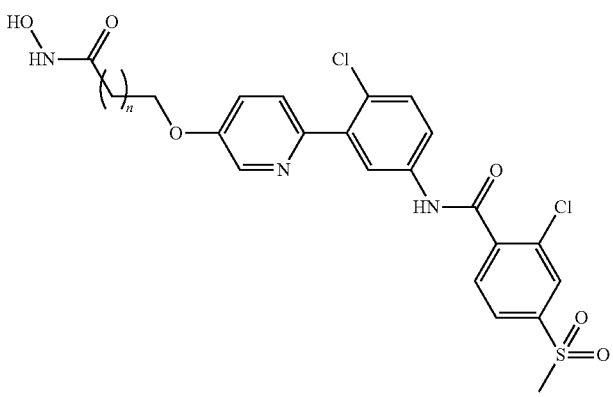
19: n = 1; 20: n = 2; 21: n = 3; 22: n = 4; 23: n = 5; 24: n = 6
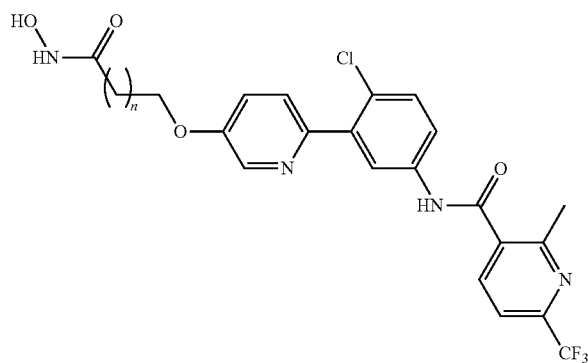
25: n = 1; 26: n = 2; 27: n = 3; 28: n = 4; 29: n = 5; 30: n = 6

-continued
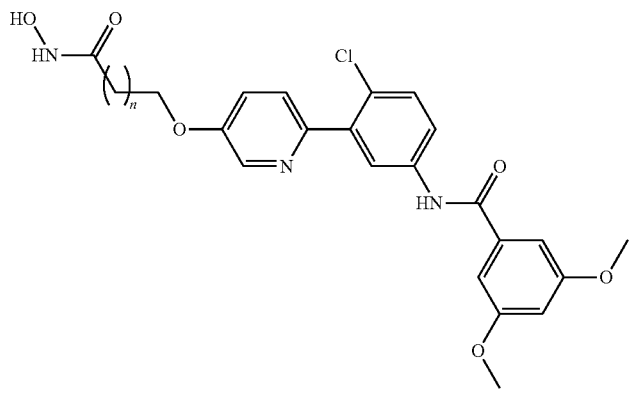
31: n = 1; 32: n = 2; 33: n = 3; 34: n = 4; 35: n = 5; 36: n = 6
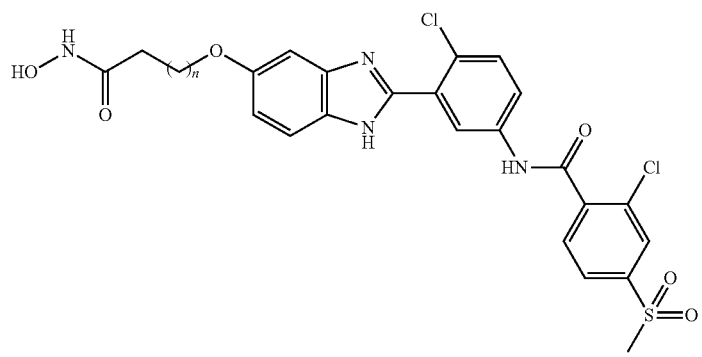
37: n = 1; 38: n = 2; 39: n = 3; 40: n = 4; 41: n = 5; 42: n = 6
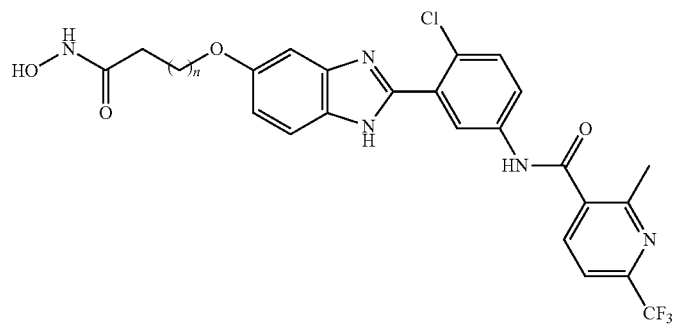
43: n = 1; 44: n = 2; 45: n = 3; 46: n = 4; 47: n = 5; 48: n = 6
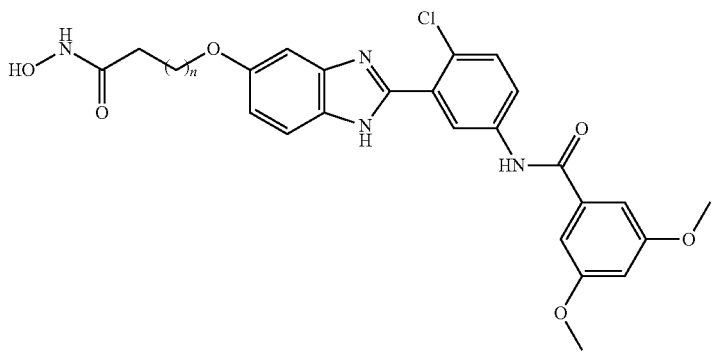
49: n = 1; 50: n = 2; 51: n = 3; 52: n = 4; 53: n = 5; 54: n = 6

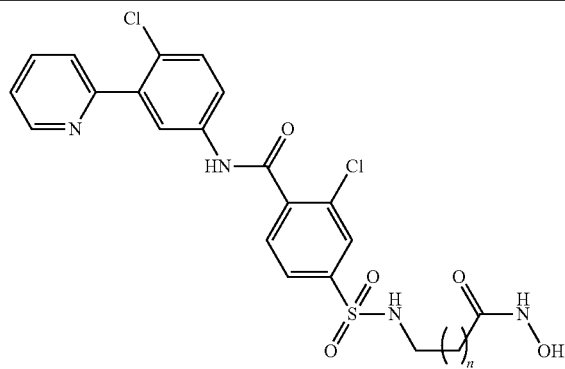
55: n = 1; 56: n = 2; 57: n = 3; 58: n = 4; 59: n = 5; 60: n = 6
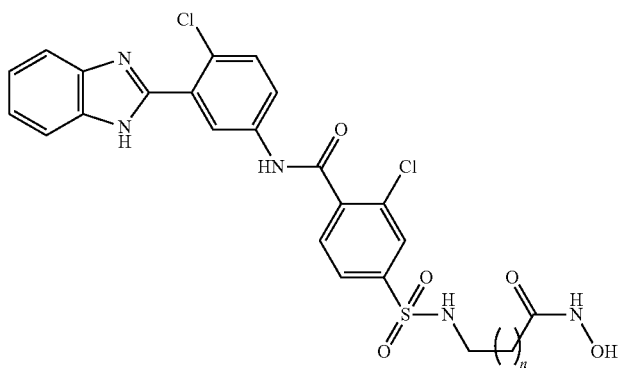
61: n = 1; 62: n = 2; 63: n = 3; 64: n = 4; 65: n = 5; 66: n = 6
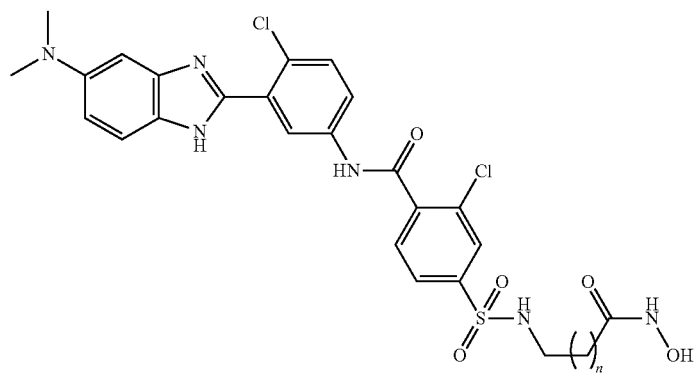
67: n = 1; 68: n = 2; 69: n = 3; 70: n = 4; 71: n = 5; 72: n = 6
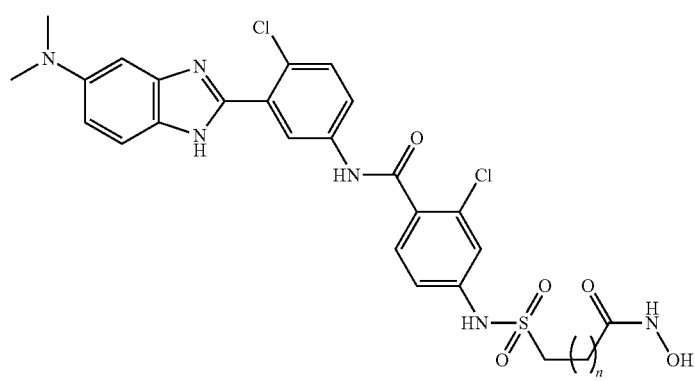
73: n = 1; 74: n = 2; 75: n = 3; 76: n = 4; 77: n = 5; 78: n = 6

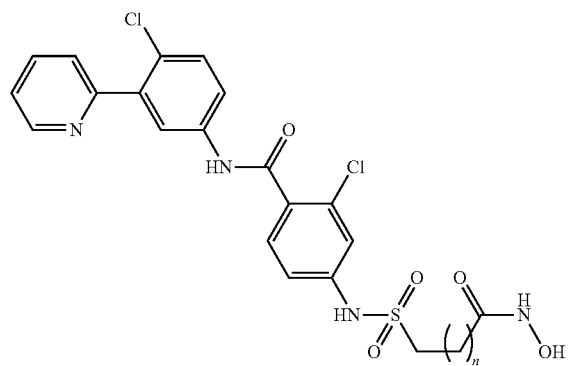
79: n = 1; 80: n = 2; 81: n = 3; 82: n = 4; 83: n = 5; 84: n = 6
85
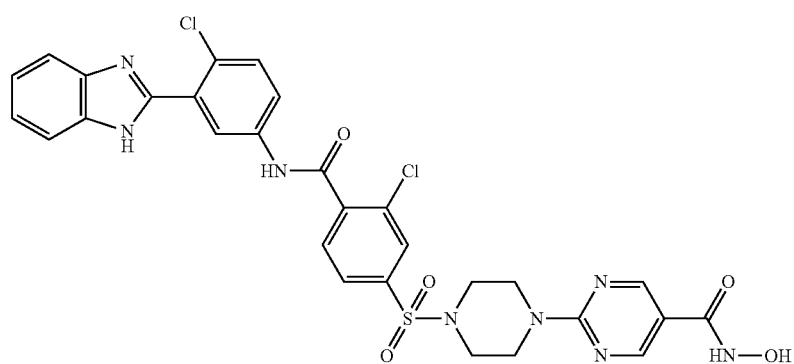 [SMILES: O=C(NO)c1cnc(N2CCN(S(=O)(=O)c3ccc(C(=O)Nc4ccc(Cl)c(-c5nc6ccccc6[nH]5)c4)c(Cl)c3)CC2)nc1]
86
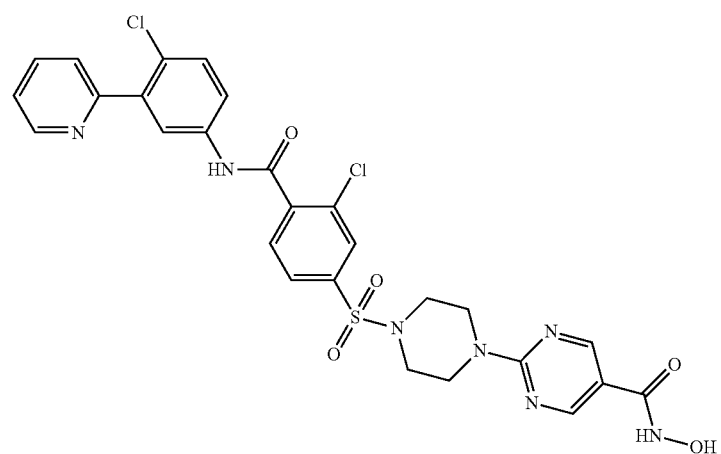 [SMILES: O=C(NO)c1cnc(N2CCN(S(=O)(=O)c3ccc(C(=O)Nc4ccc(Cl)c(-c5ccccn5)c4)c(Cl)c3)CC2)nc1]

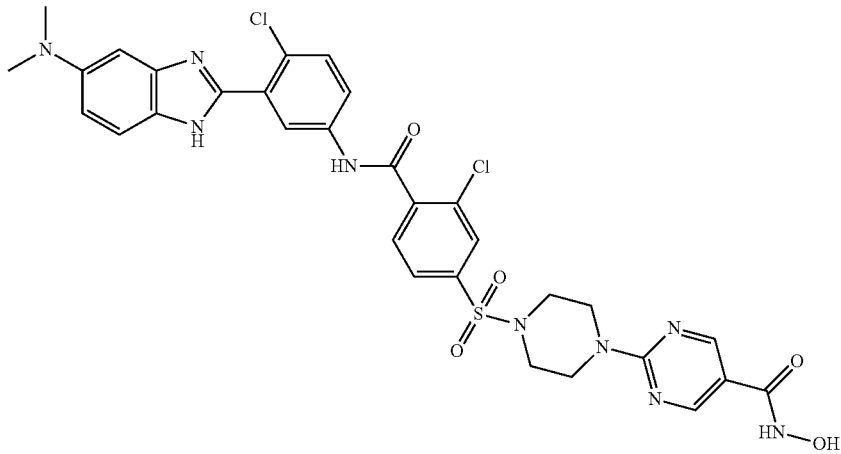 [SMILES: CN(C)c1ccc2[nH]c(-c3cc(NC(=O)c4ccc(S(=O)(=O)N5CCN(c6ncc(C(=O)NO)cn6)CC5)cc4Cl)ccc3Cl)nc2c1]
87
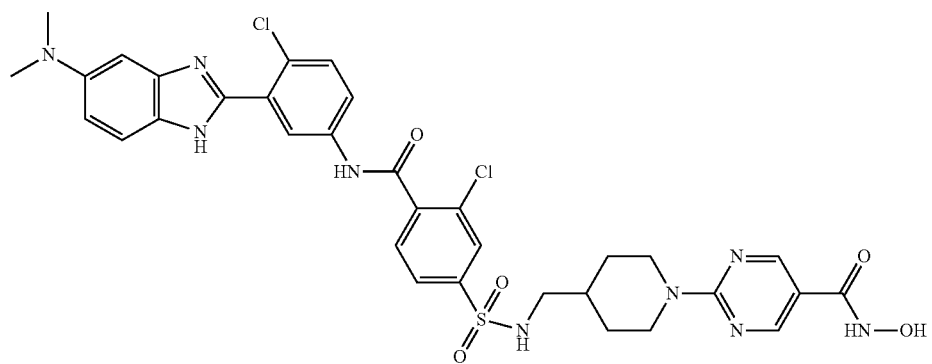 [SMILES: CN(C)c1ccc2[nH]c(-c3cc(NC(=O)c4ccc(S(=O)(=O)NCC5CCN(c6ncc(C(=O)NO)cn6)CC5)cc4Cl)ccc3Cl)nc2c1]
88
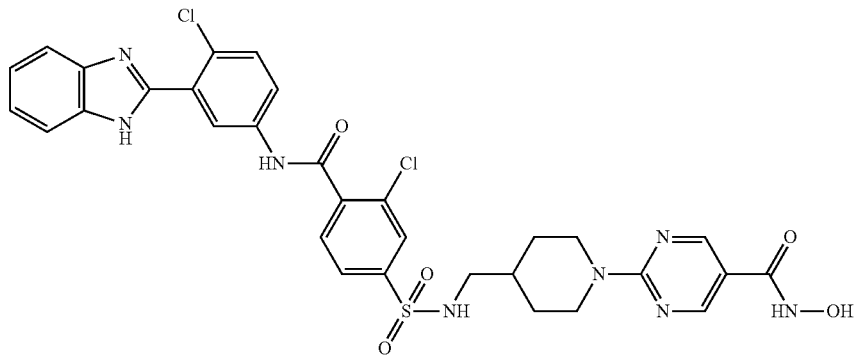 [SMILES: O=C(NO)c1cnc(N2CCC(CNS(=O)(=O)c3ccc(C(=O)Nc4ccc(Cl)c(-c5nc6ccccc6[nH]5)c4)c(Cl)c3)CC2)nc1]
89
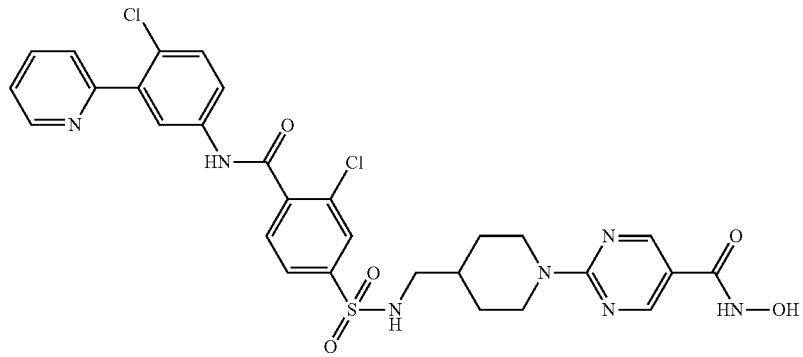 [SMILES: O=C(NO)c1cnc(N2CCC(CNS(=O)(=O)c3ccc(C(=O)Nc4ccc(Cl)c(-c5ccccn5)c4)c(Cl)c3)CC2)nc1]
90

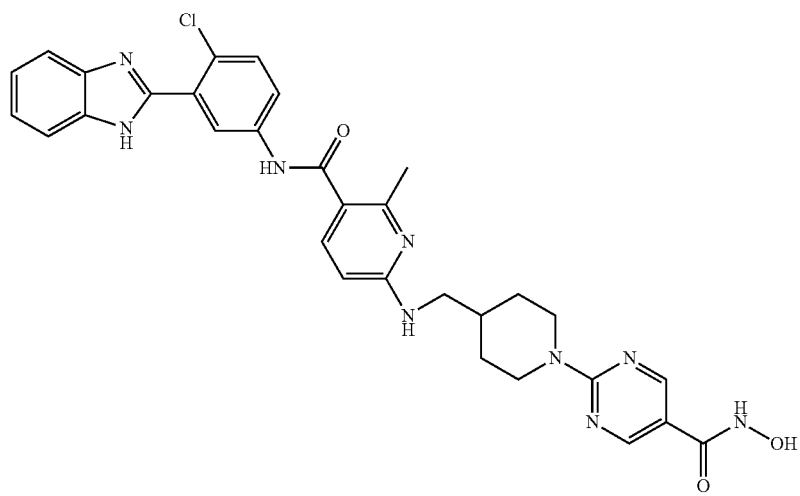 [SMILES: Cc1nc(NCC2CCN(c3ncc(C(=O)NO)cn3)CC2)ccc1C(=O)Nc1ccc(Cl)c(-c2nc3ccccc3[nH]2)c1]
91
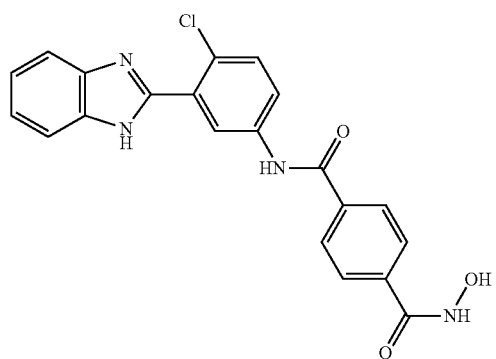 [SMILES: O=C(NO)c1ccc(C(=O)Nc2ccc(Cl)c(-c3nc4ccccc4[nH]3)c2)cc1]
92
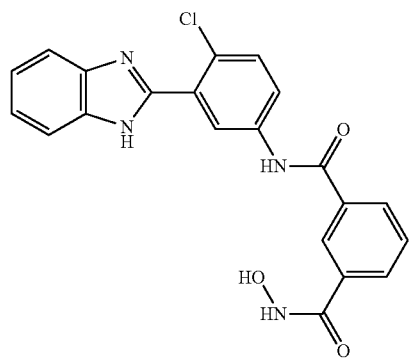 [SMILES: O=C(NO)c1cccc(C(=O)Nc2ccc(Cl)c(-c3nc4ccccc4[nH]3)c2)c1]
93
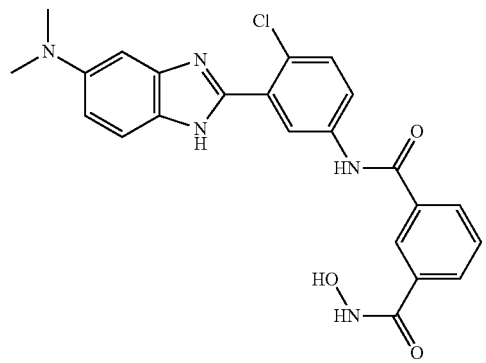 [SMILES: CN(C)c1ccc2[nH]c(-c3cc(NC(=O)c4cccc(C(=O)NO)c4)ccc3Cl)nc2c1]
94

-continued
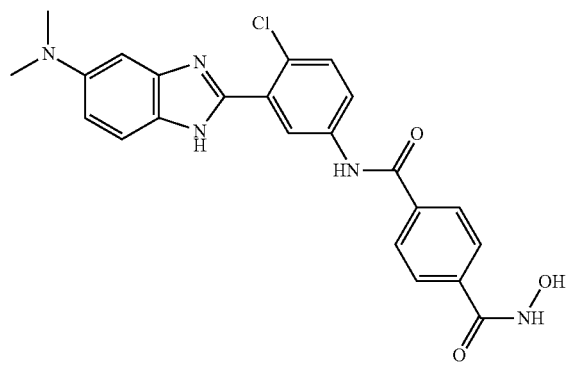 [SMILES: CN(C)c1ccc2[nH]c(-c3cc(NC(=O)c4ccc(C(=O)NO)cc4)ccc3Cl)nc2c1]
95
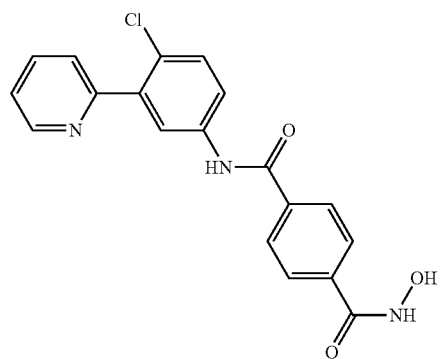 [SMILES: O=C(NO)c1ccc(C(=O)Nc2ccc(Cl)c(-c3ccccn3)c2)cc1]
96
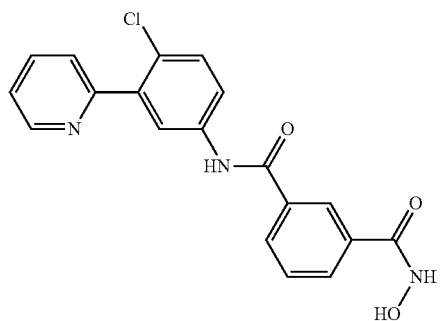 [SMILES: O=C(NO)c1cccc(C(=O)Nc2ccc(Cl)c(-c3ccccn3)c2)c1]
97
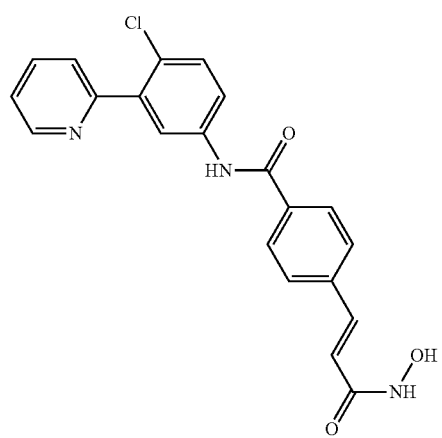 [SMILES: O=C(/C=C/c1ccc(C(=O)Nc2ccc(Cl)c(-c3ccccn3)c2)cc1)NO]
98

-continued
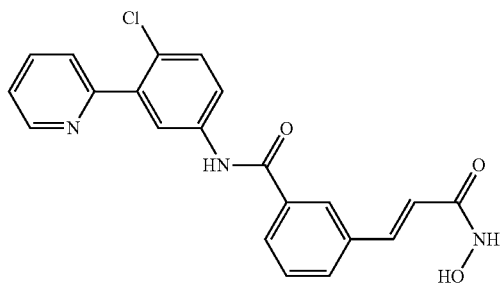 [SMILES: O=C(/C=C/c1cccc(C(=O)Nc2ccc(Cl)c(-c3ccccn3)c2)c1)NO]
99
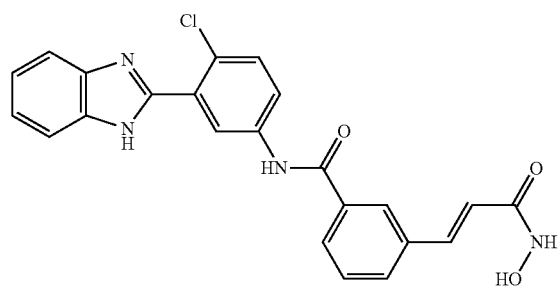 [SMILES: O=C(/C=C/c1cccc(C(=O)Nc2ccc(Cl)c(-c3nc4ccccc4[nH]3)c2)c1)NO]
100
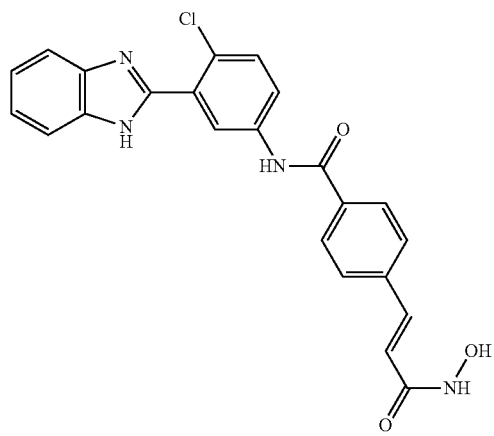 [SMILES: O=C(/C=C/c1ccc(C(=O)Nc2ccc(Cl)c(-c3nc4ccccc4[nH]3)c2)cc1)NO]
101
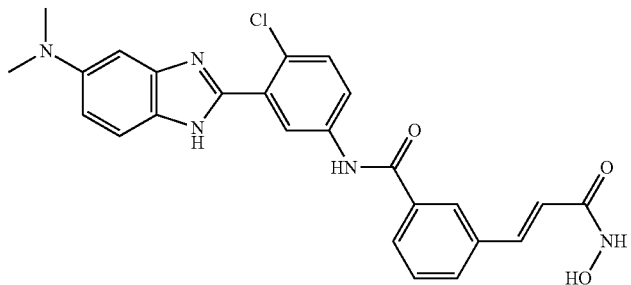 [SMILES: CN(C)c1ccc2[nH]c(-c3cc(NC(=O)c4cccc(/C=C/C(=O)NO)c4)ccc3Cl)nc2c1]
102

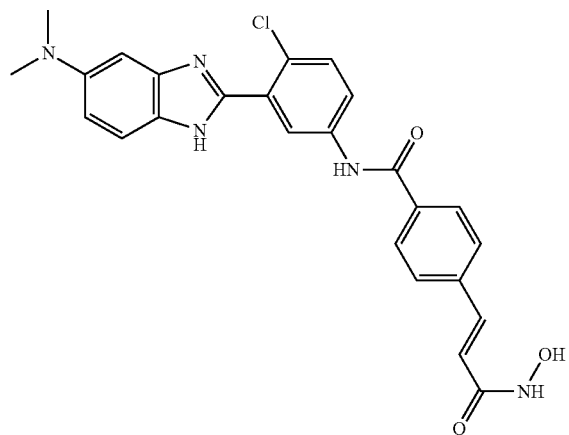 [SMILES: CN(C)c1ccc2[nH]c(-c3cc(NC(=O)c4ccc(/C=C/C(=O)NO)cc4)ccc3Cl)nc2c1]
103
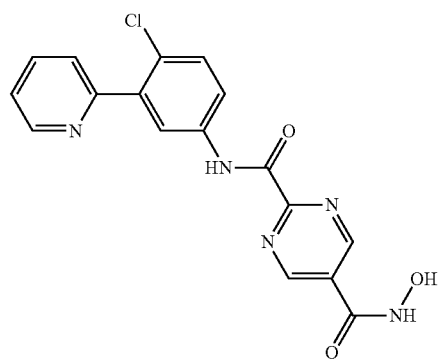 [SMILES: O=C(NO)c1cnc(C(=O)Nc2ccc(Cl)c(-c3ccccn3)c2)nc1]
104
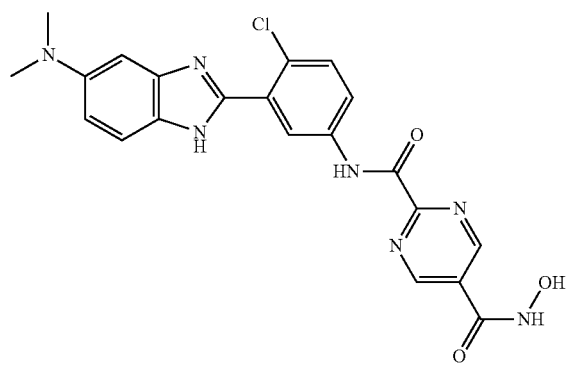
105
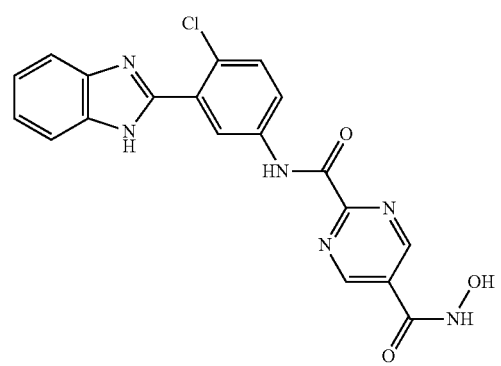 [SMILES: O=C(NO)c1cnc(C(=O)Nc2ccc(Cl)c(-c3nc4ccccc4[nH]3)c2)nc1]
106

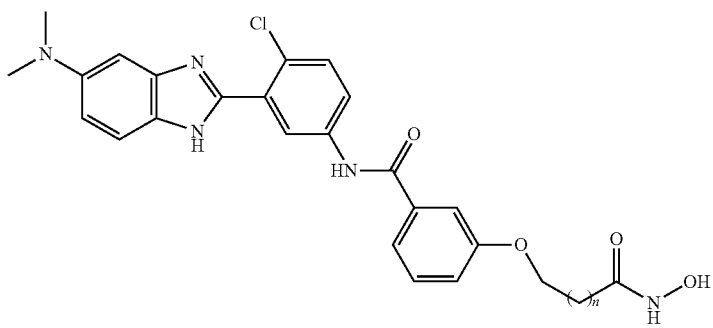
107: n = 1; 108: n = 2; 109: n = 3; 110: n = 4; 111: n = 5; 112: n = 6
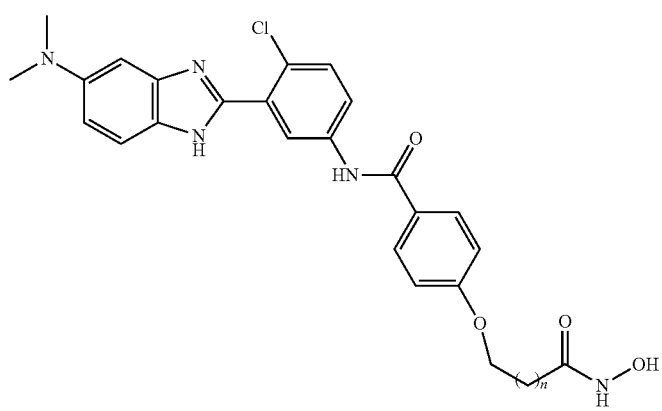
113: n = 1; 114: n = 2; 115: n = 3; 116: n = 4; 117: n = 5; 118: n = 6
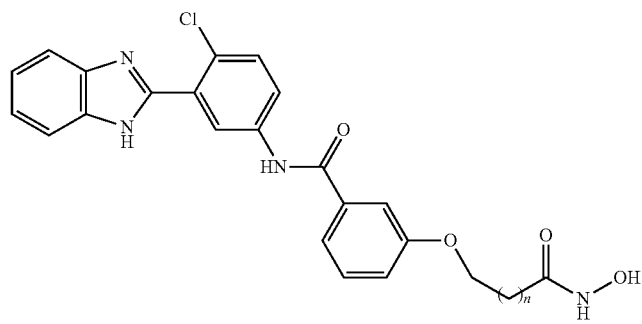
119: n = 1; 120: n = 2; 121: n = 3; 122: n = 4; 123: n = 5; 124: n = 6
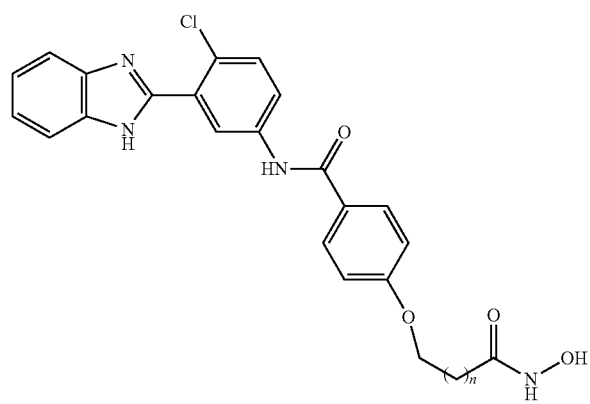
125: n = 1; 126: n = 2; 127: n = 3; 128: n = 4; 129: n = 5; 130: n = 6

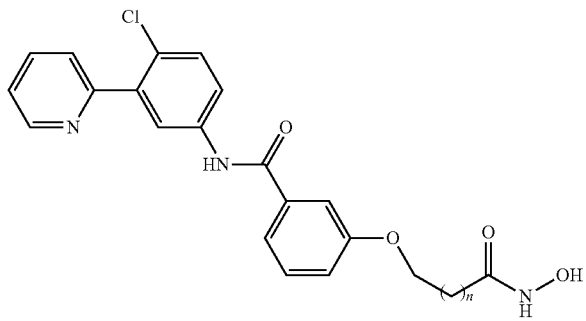
131: n = 1; 132: n = 2; 133: n = 3; 134: n = 4; 135: n = 5; 136: n = 6
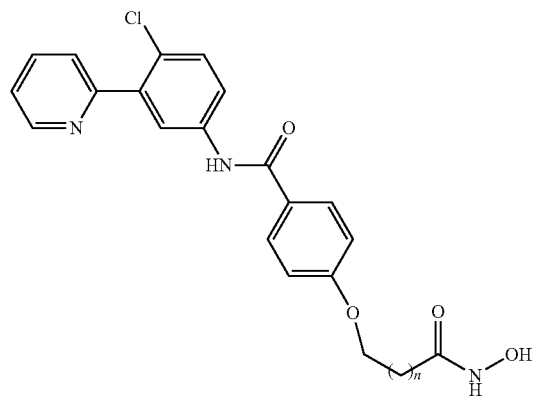
137: n = 1; 138: n = 2; 139: n = 3; 140: n = 4; 141: n = 5; 142: n = 6
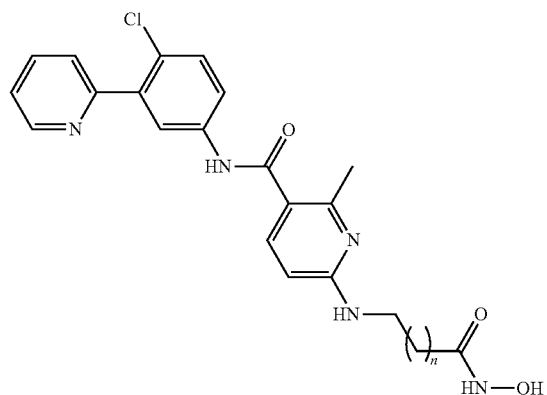
143: n = 1; 144: n = 2; 145: n = 3; 146: n = 4; 147: n = 5; 148: n = 6

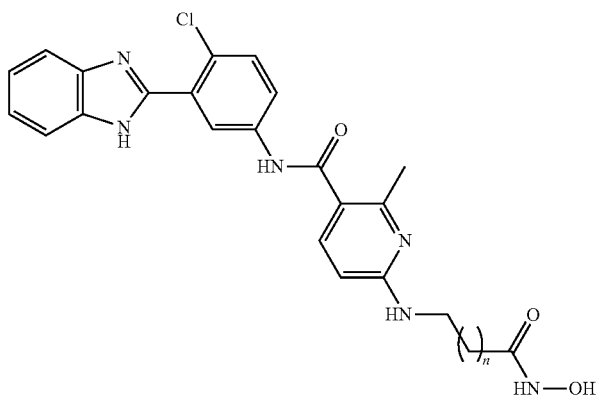
149: n = 1; 150: n = 2; 151 n = 3; 152: n = 4; 153: n = 5; 154: n = 6
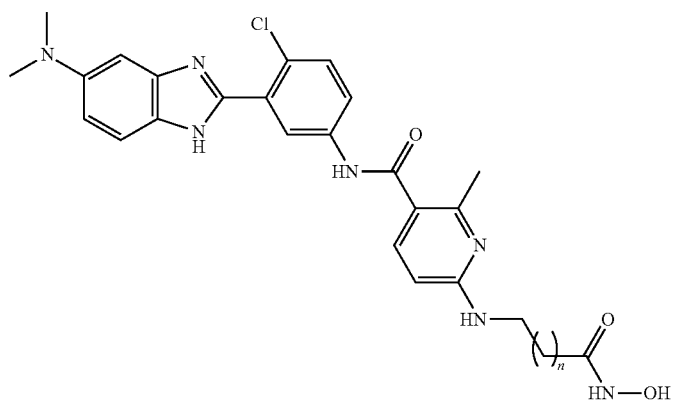
155: n = 1; 156: n = 2; 157 n = 3; 158: n = 4; 159: n = 5; 160: n = 6
161
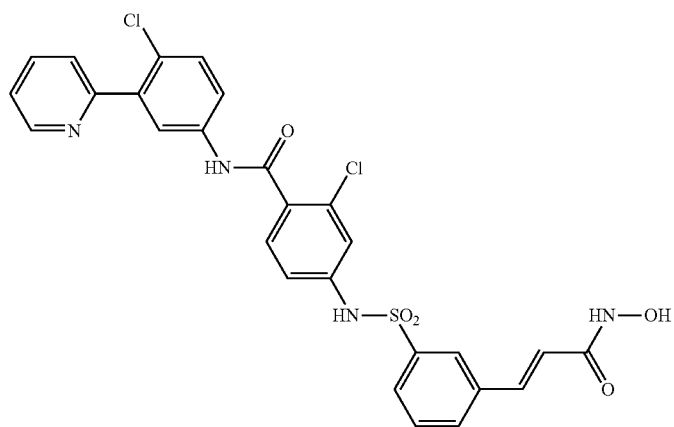 [SMILES: O=C(/C=C/c1cccc(S(=O)(=O)Nc2ccc(C(=O)Nc3ccc(Cl)c(-c4ccccn4)c3)c(Cl)c2)c1)NO]

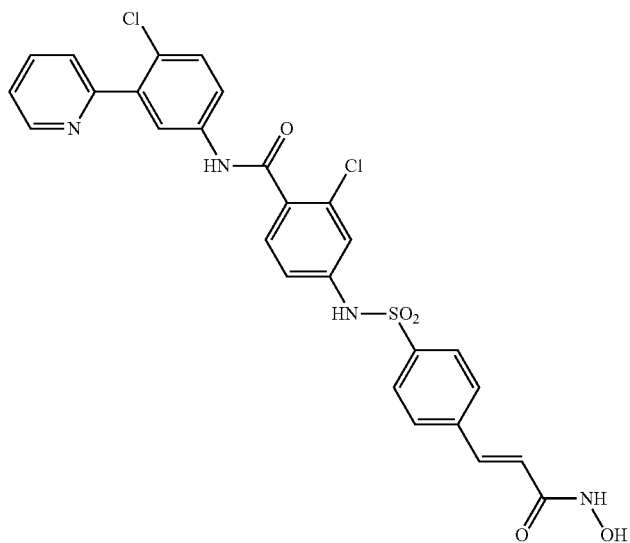 [SMILES: O=C(/C=C/c1ccc(S(=O)(=O)Nc2ccc(C(=O)Nc3ccc(Cl)c(-c4ccccn4)c3)c(Cl)c2)cc1)NO]
162
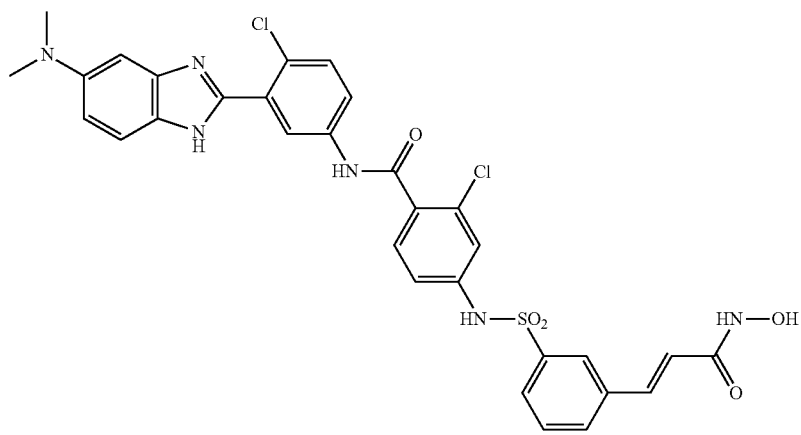 [SMILES: CN(C)c1ccc2[nH]c(-c3cc(NC(=O)c4ccc(NS(=O)(=O)c5cccc(/C=C/C(=O)NO)c5)cc4Cl)ccc3Cl)nc2c1]
163
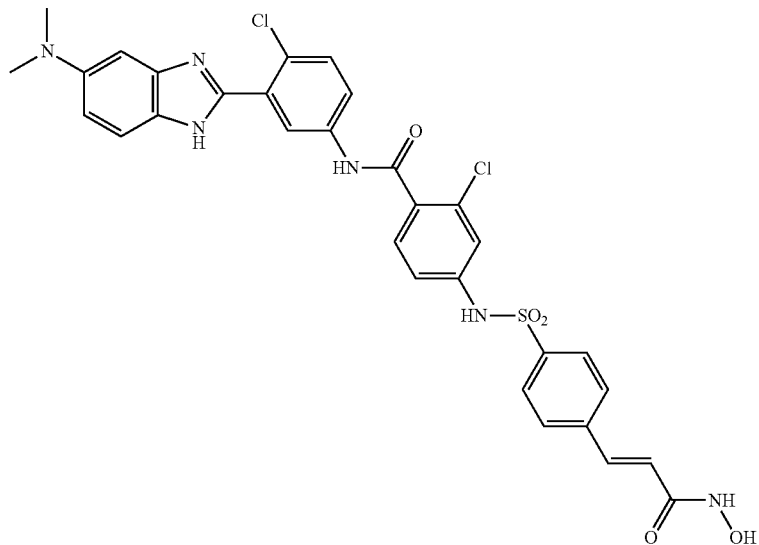 [SMILES: CN(C)c1ccc2[nH]c(-c3cc(NC(=O)c4ccc(NS(=O)(=O)c5ccc(/C=C/C(=O)NO)cc5)cc4Cl)ccc3Cl)nc2c1]
164

-continued
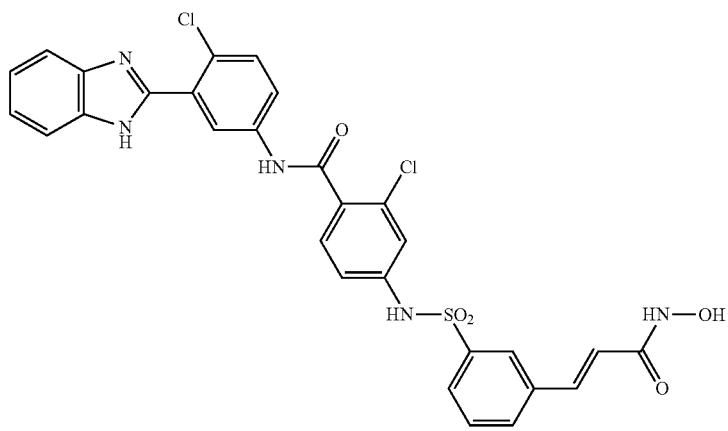 [SMILES: O=C(/C=C/c1cccc(S(=O)(=O)Nc2ccc(C(=O)Nc3ccc(Cl)c(-c4nc5ccccc5[nH]4)c3)c(Cl)c2)c1)NO]
165
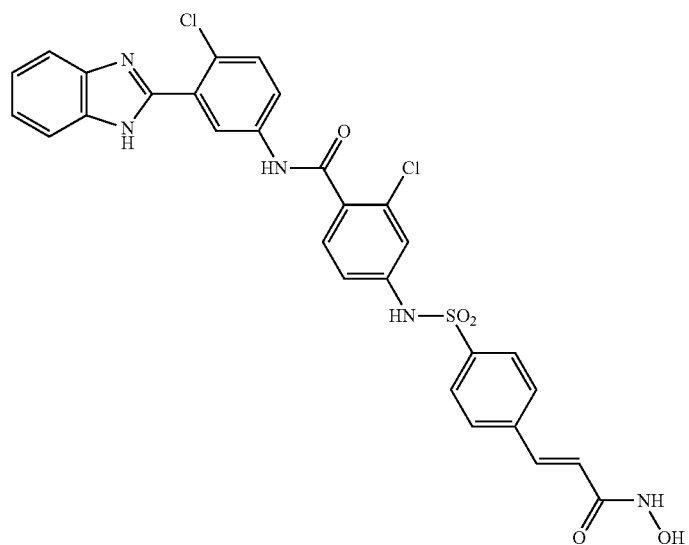 [SMILES: O=C(/C=C/c1ccc(S(=O)(=O)Nc2ccc(C(=O)Nc3ccc(Cl)c(-c4nc5ccccc5[nH]4)c3)c(Cl)c2)cc1)NO]
166
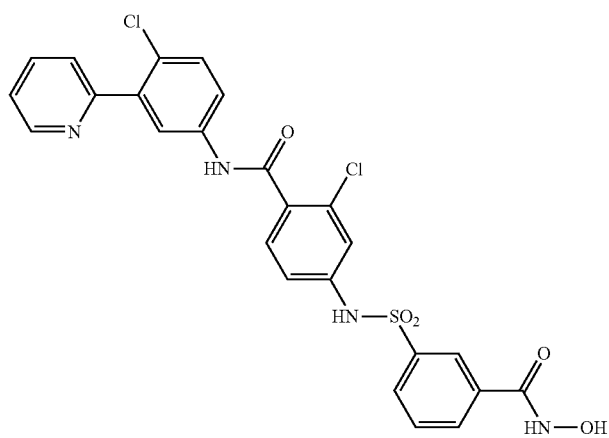 [SMILES: O=C(NO)c1cccc(S(=O)(=O)Nc2ccc(C(=O)Nc3ccc(Cl)c(-c4ccccn4)c3)c(Cl)c2)c1]
167

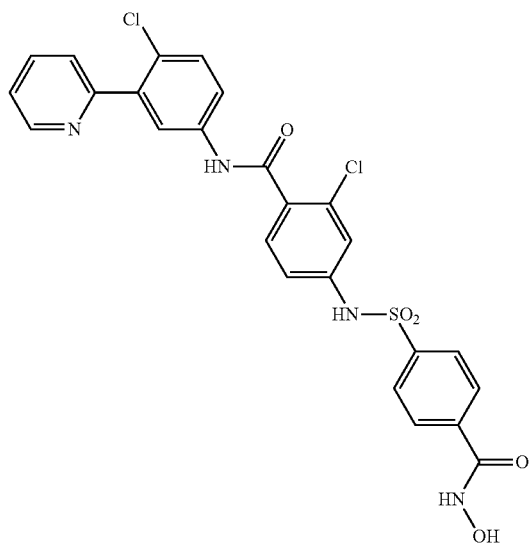 [SMILES: O=C(NO)c1ccc(S(=O)(=O)Nc2ccc(C(=O)Nc3ccc(Cl)c(-c4ccccn4)c3)c(Cl)c2)cc1]
168
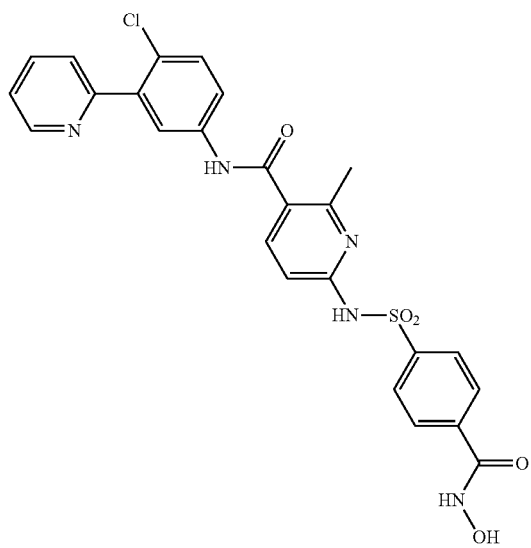 [SMILES: Cc1nc(NS(=O)(=O)c2ccc(C(=O)NO)cc2)ccc1C(=O)Nc1ccc(Cl)c(-c2ccccn2)c1]
169
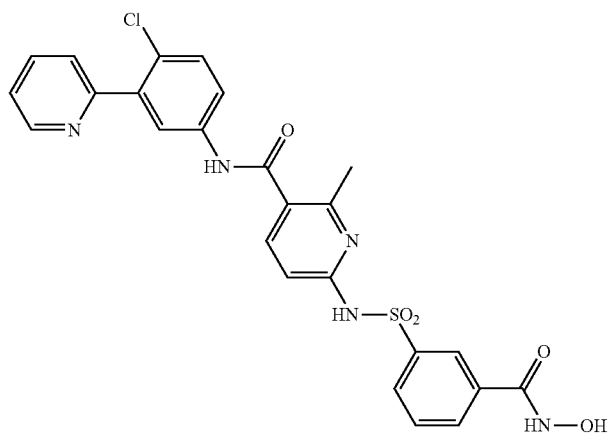 [SMILES: Cc1nc(NS(=O)(=O)c2cccc(C(=O)NO)c2)ccc1C(=O)Nc1ccc(Cl)c(-c2ccccn2)c1]
170

-continued
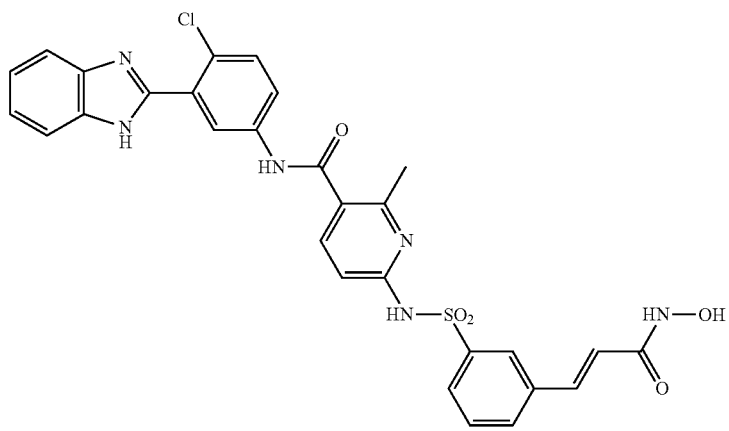 [SMILES: Cc1nc(NS(=O)(=O)c2cccc(/C=C/C(=O)NO)c2)ccc1C(=O)Nc1ccc(Cl)c(-c2nc3ccccc3[nH]2)c1]
171
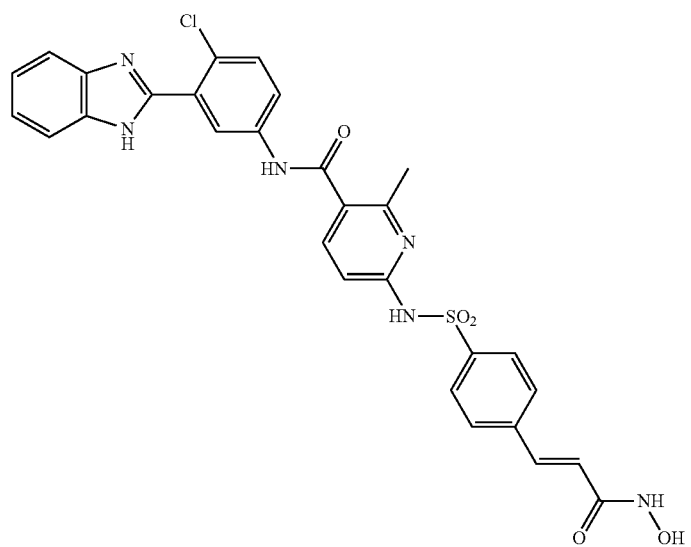 [SMILES: Cc1nc(NS(=O)(=O)c2ccc(/C=C/C(=O)NO)cc2)ccc1C(=O)Nc1ccc(Cl)c(-c2nc3ccccc3[nH]2)c1]
172
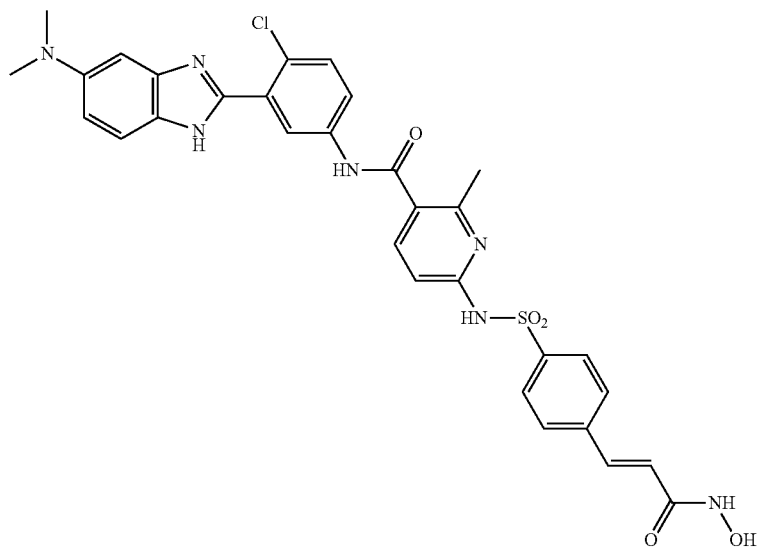 [SMILES: Cc1nc(NS(=O)(=O)c2ccc(/C=C/C(=O)NO)cc2)ccc1C(=O)Nc1ccc(Cl)c(-c2nc3cc(N(C)C)ccc3[nH]2)c1]
173

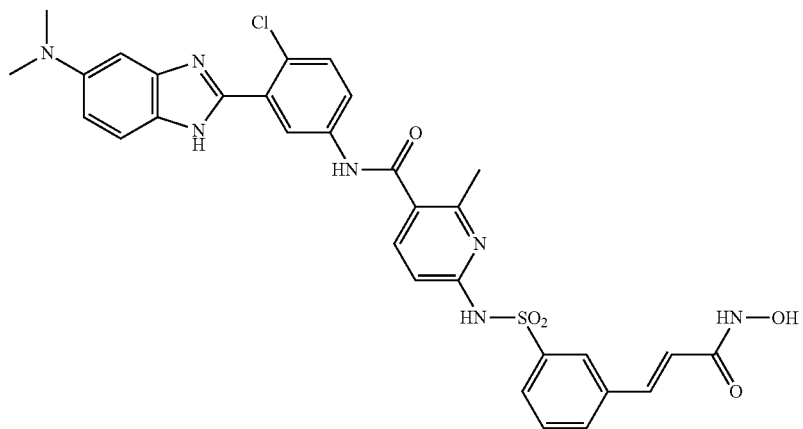 [SMILES: Cc1nc(NS(=O)(=O)c2cccc(/C=C/C(=O)NO)c2)ccc1C(=O)Nc1ccc(Cl)c(-c2nc3cc(N(C)C)ccc3[nH]2)c1]
174
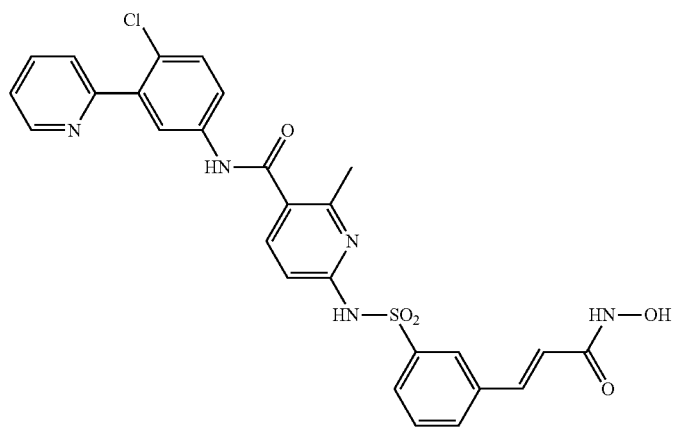 [SMILES: Cc1nc(NS(=O)(=O)c2cccc(/C=C/C(=O)NO)c2)ccc1C(=O)Nc1ccc(Cl)c(-c2ccccn2)c1]
175
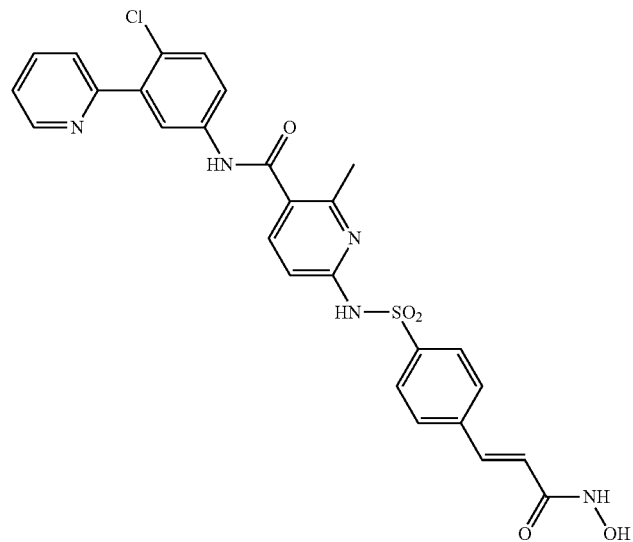
176

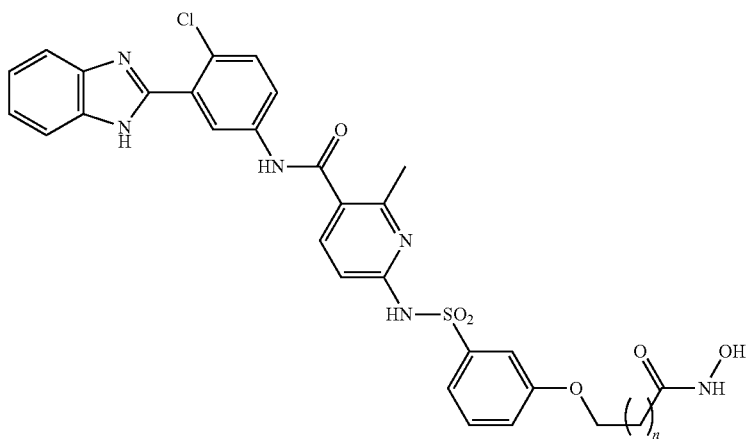
177: n = 1; 178: n = 2; 179: n = 3; 180: n = 4; 181: n = 5; 182: n = 6
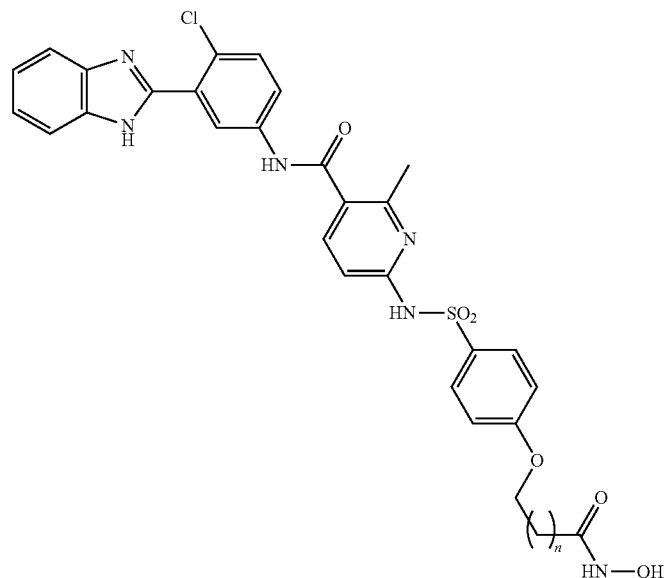
183: n = 1; 184: n = 2; 185: n = 3; 186: n = 4; 187: n = 5; 188: n = 6
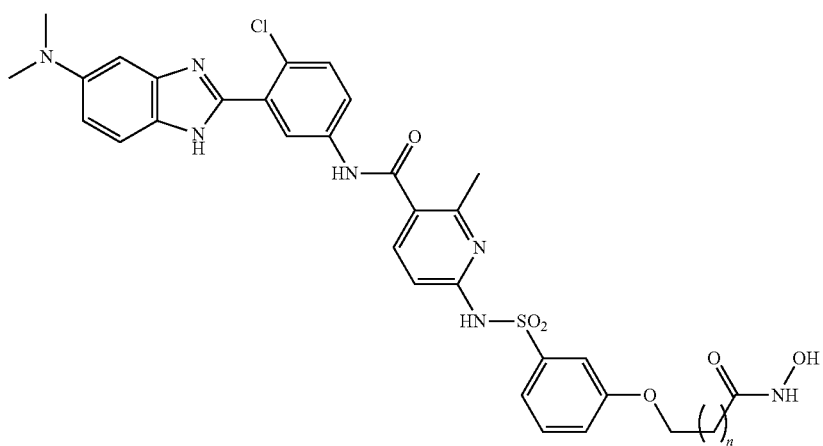
189: n = 1; 190: n = 2; 191: n = 3; 192: n = 4; 193: n = 5; 194: n = 6

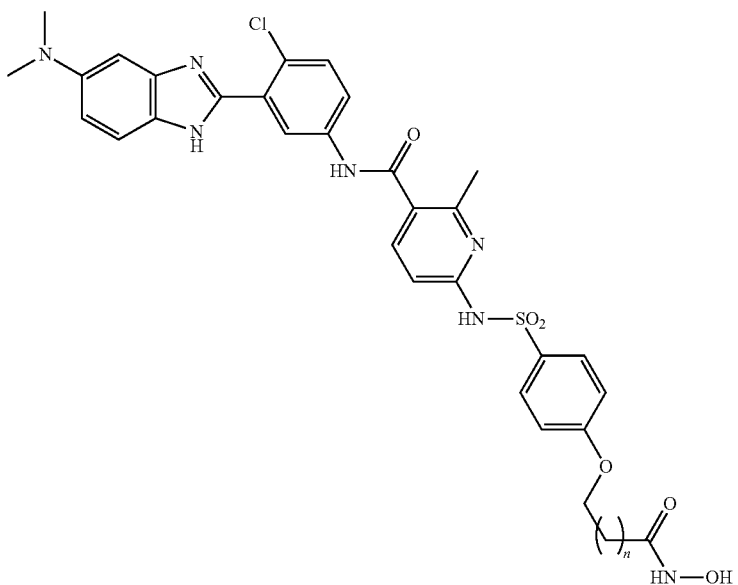
195: n = 1; 196: n = 2; 197: n = 3; 198: n = 4; 199: n = 5; 200: n = 6
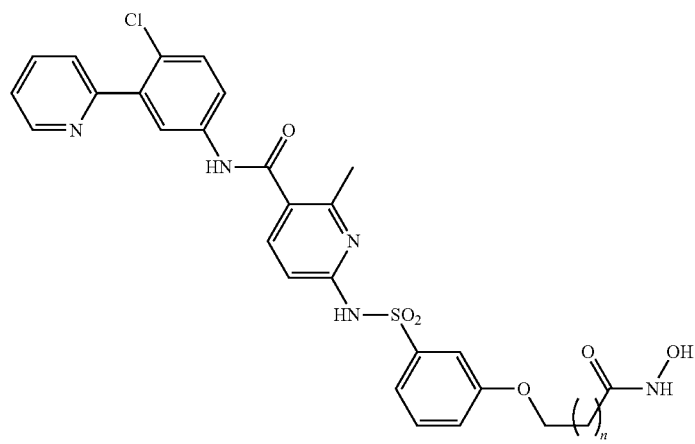
201: n = 1; 202: n = 2; 203: n = 3; 204: n = 4; 205: n = 5; 206: n = 6

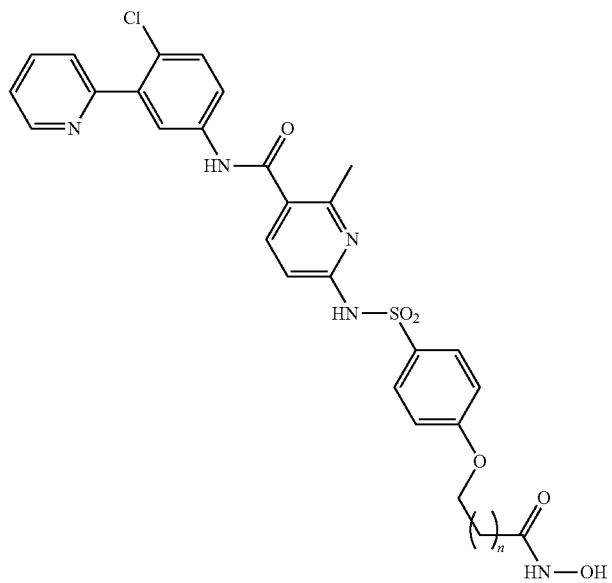
207: n = 1; 208: n = 2; 209: n = 3; 210: n = 4; 211: n = 5; 212: n = 6
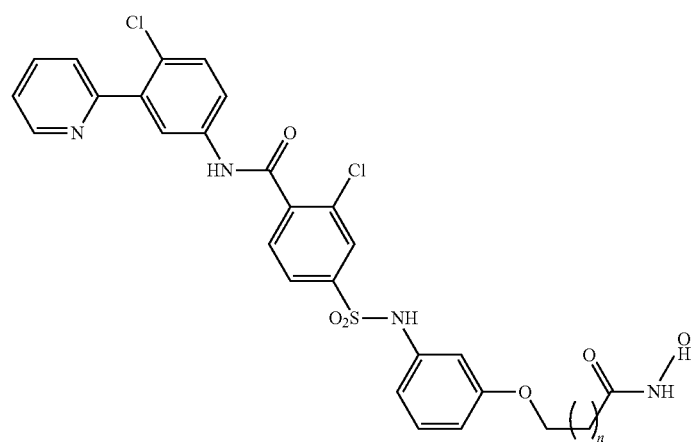
213: n = 1; 214: n = 2; 215: n = 3; 216: n = 4; 217: n = 5; 218: n = 6

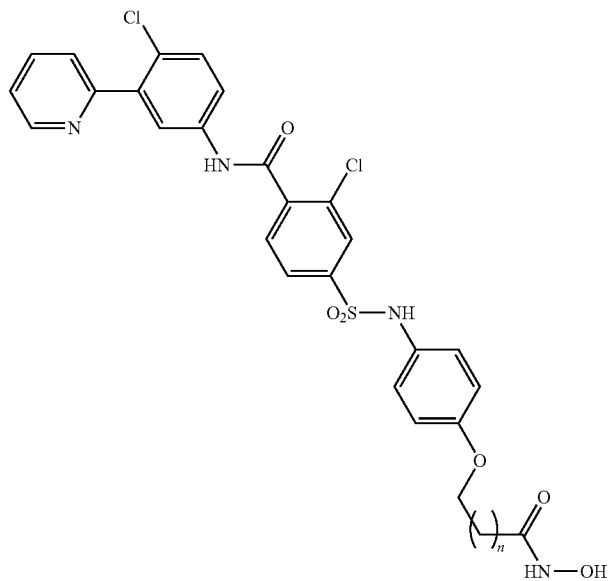
219: n = 1; 220: n = 2; 221: n = 3; 222: n = 4; 223: n = 5; 224: n = 6
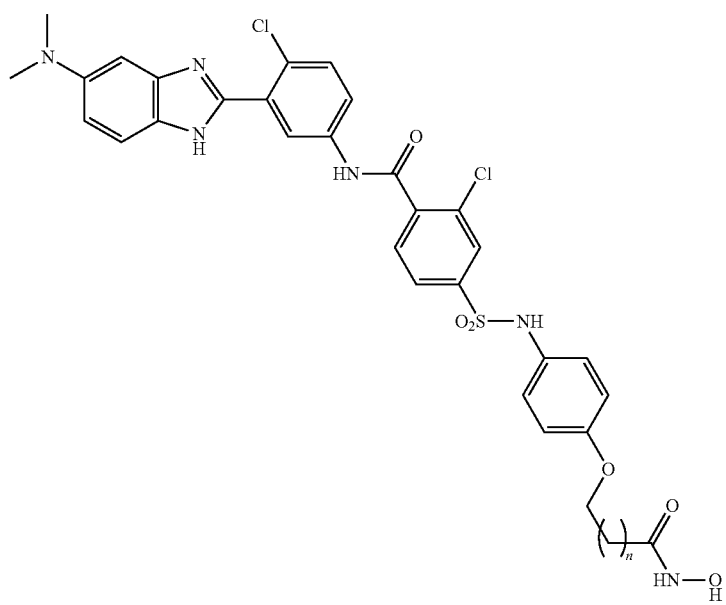
225: n = 1; 226: n = 2; 227: n = 3; 228: n = 4; 229: n = 5; 230: n = 6

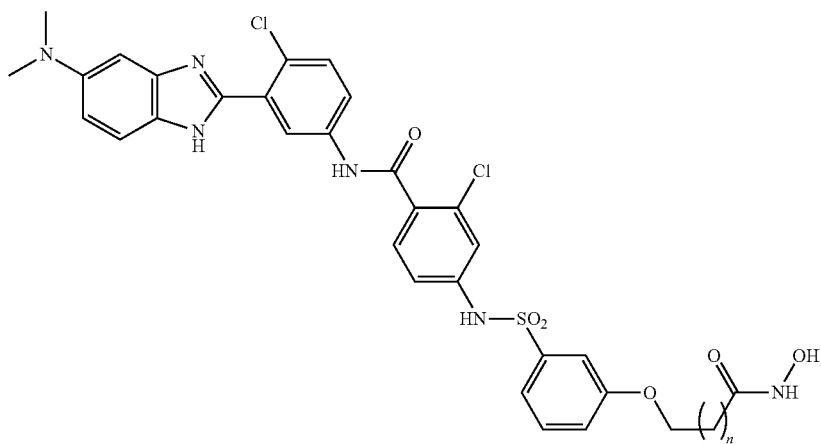
231: n = 1; 232: n = 2; 233: n = 3; 234: n = 4; 235: n = 5; 236: n = 6
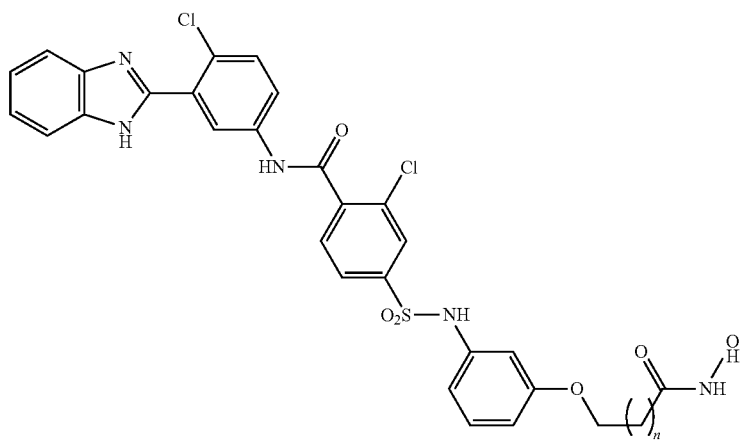
237: n = 1; 238: n = 2; 239: n = 3; 240: n = 4; 241: n = 5; 242: n = 6
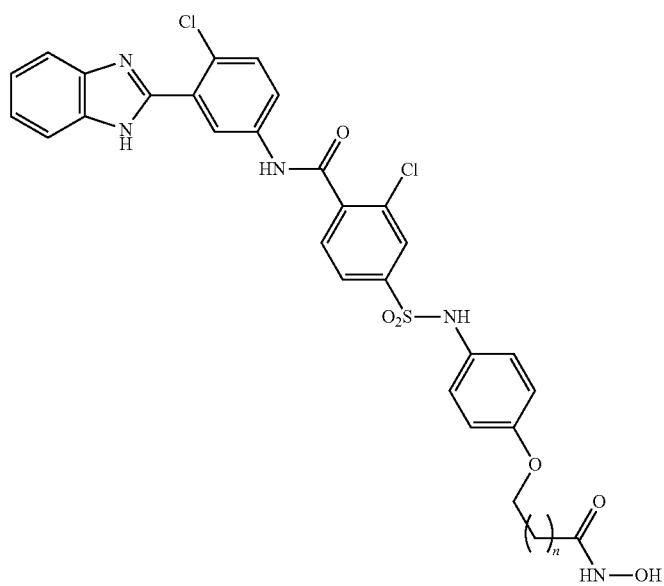
243: n = 1; 244: n = 2; 245: n = 3; 246: n = 4; 247: n = 5; 248: n = 6

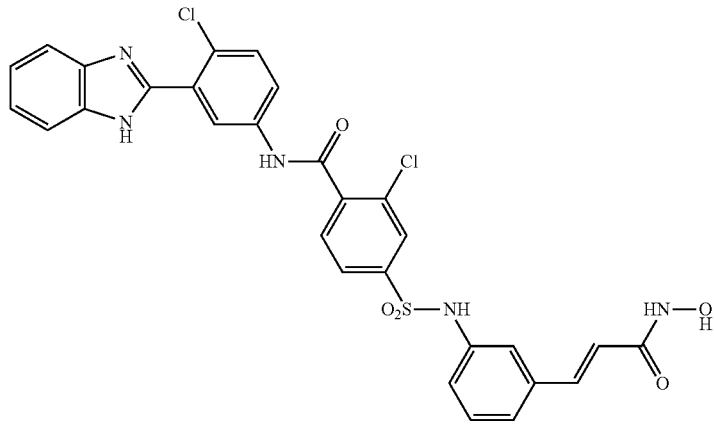 [SMILES: O=C(/C=C/c1cccc(NS(=O)(=O)c2ccc(C(=O)Nc3ccc(Cl)c(-c4nc5ccccc5[nH]4)c3)c(Cl)c2)c1)NO]
249
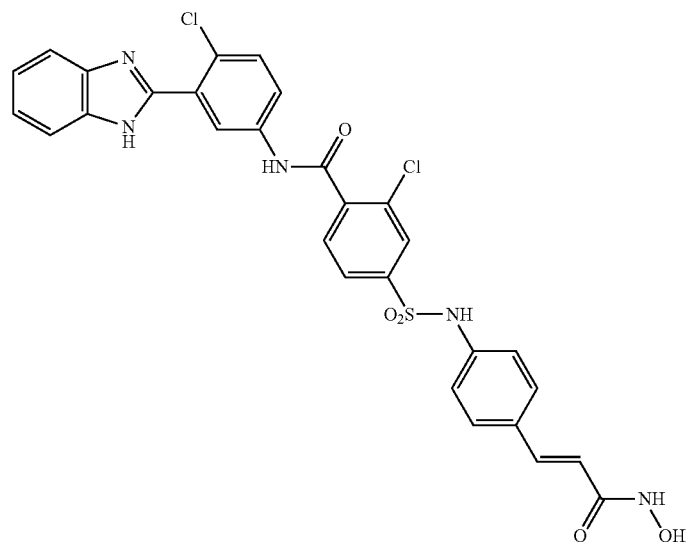
250
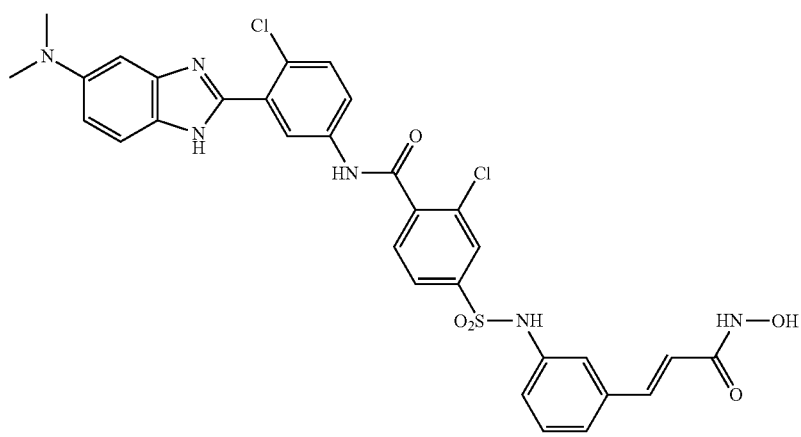
251

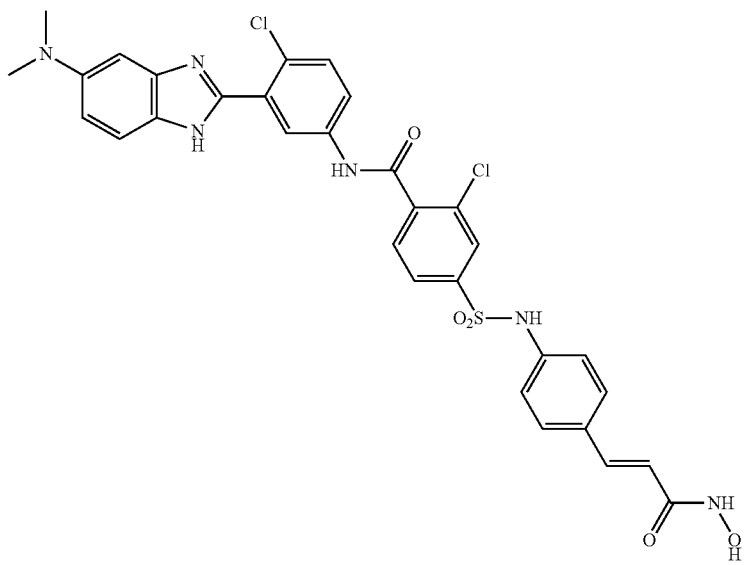 [SMILES: CN(C)c1ccc2[nH]c(-c3cc(NC(=O)c4ccc(S(=O)(=O)Nc5ccc(/C=C/C(=O)NO)cc5)cc4Cl)ccc3Cl)nc2c1]
252
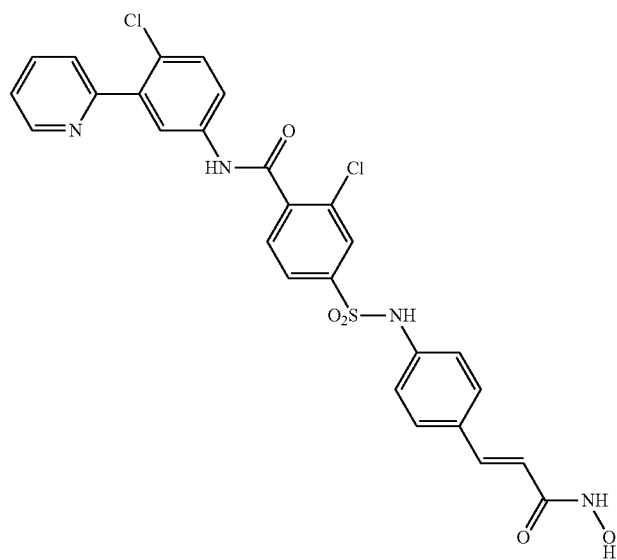 [SMILES: O=C(/C=C/c1ccc(NS(=O)(=O)c2ccc(C(=O)Nc3ccc(Cl)c(-c4ccccn4)c3)c(Cl)c2)cc1)NO]
253
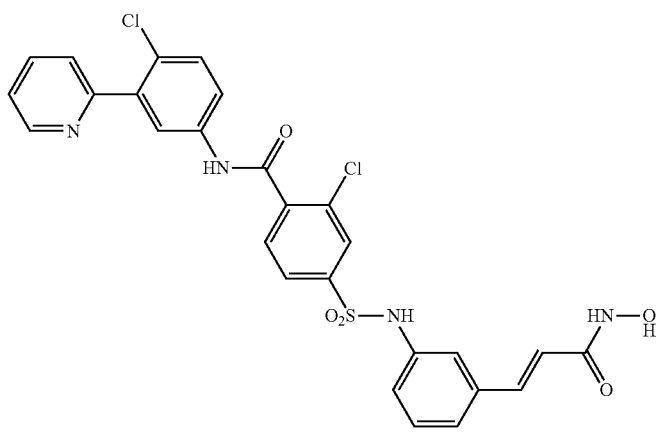 [SMILES: O=C(/C=C/c1cccc(NS(=O)(=O)c2ccc(C(=O)Nc3ccc(Cl)c(-c4ccccn4)c3)c(Cl)c2)c1)NO]
254

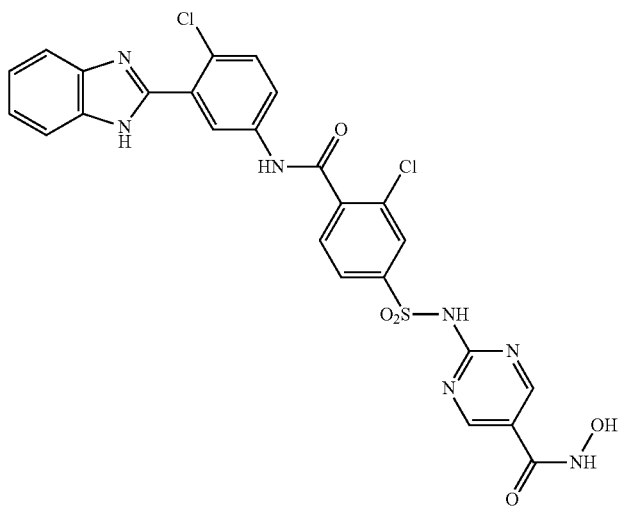 [SMILES: O=C(NO)c1cnc(NS(=O)(=O)c2ccc(C(=O)Nc3ccc(Cl)c(-c4nc5ccccc5[nH]4)c3)c(Cl)c2)nc1]
255
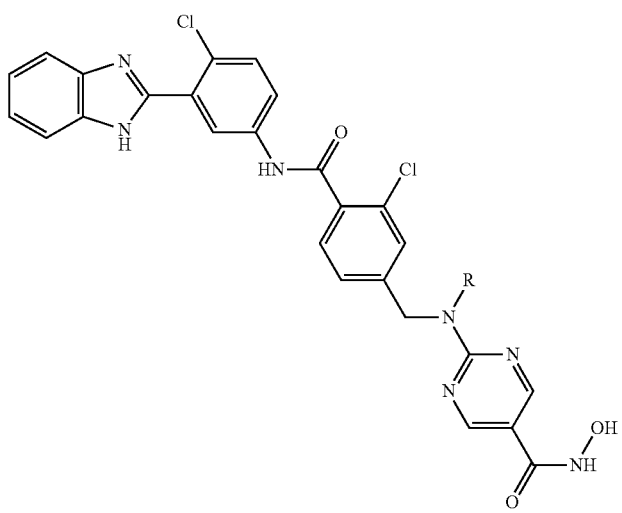
256: R = H; 257: R = Me
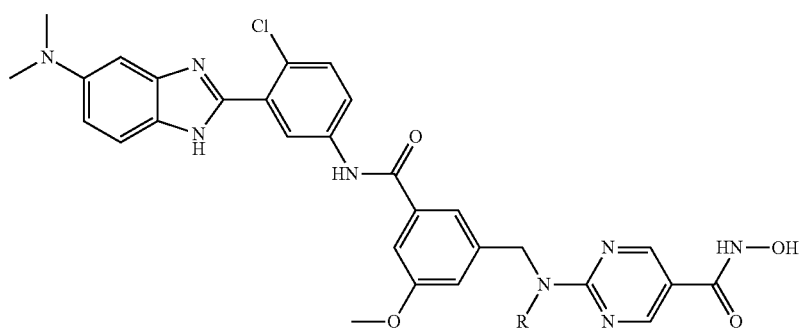
258: R = H; 259: R = Me -continued
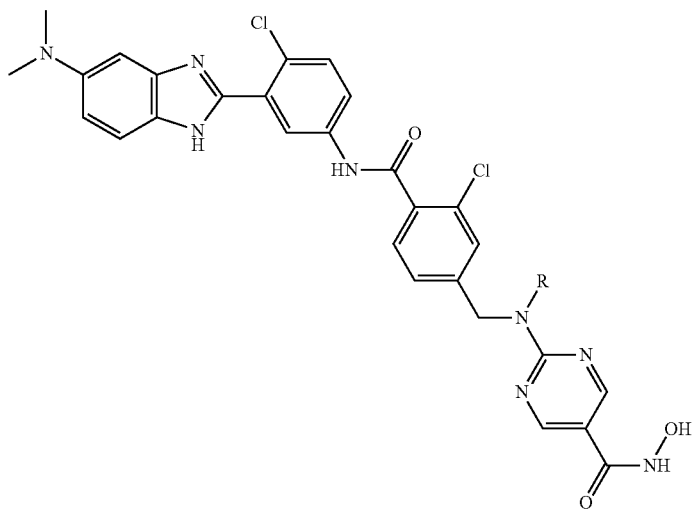
260: R = H; 261: R = Me
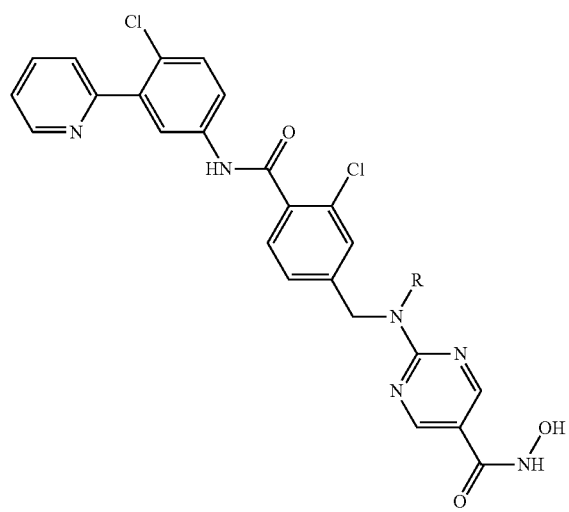
262: R = H; 263: R = Me
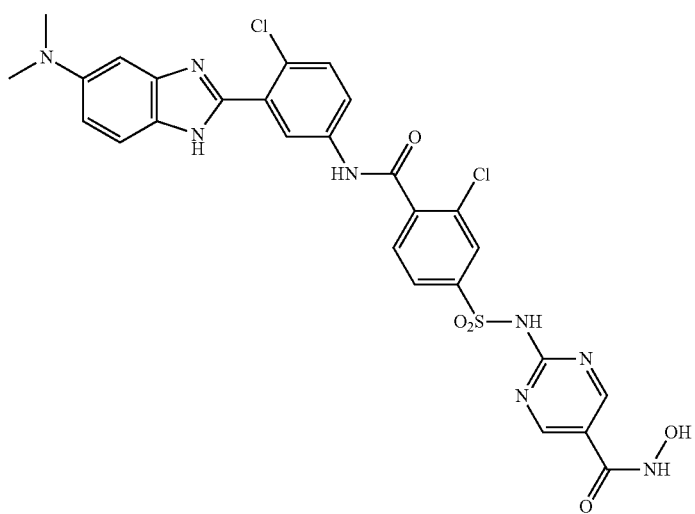 [SMILES: CN(C)c1ccc2[nH]c(-c3cc(NC(=O)c4ccc(S(=O)(=O)Nc5ncc(C(=O)NO)cn5)cc4Cl)ccc3Cl)nc2c1]
264

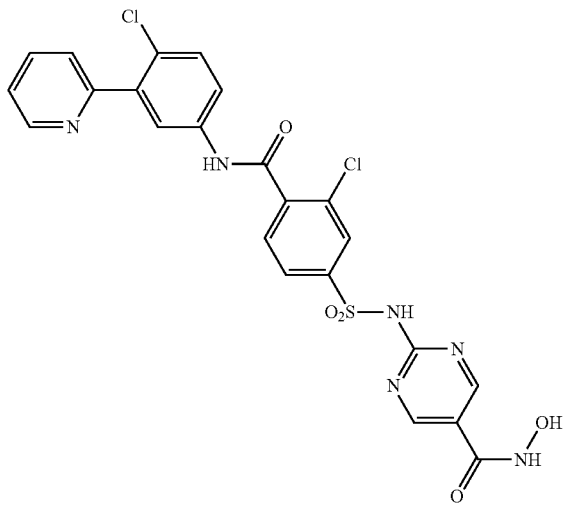 [SMILES: O=C(NO)c1cnc(NS(=O)(=O)c2ccc(C(=O)Nc3ccc(Cl)c(-c4ccccn4)c3)c(Cl)c2)nc1]

265

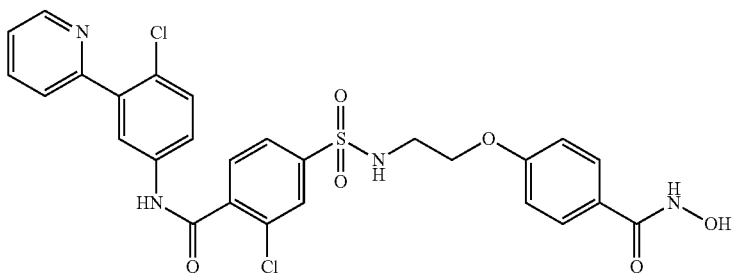 [SMILES: O=C(NO)c1ccc(OCCNS(=O)(=O)c2ccc(C(=O)Nc3ccc(Cl)c(-c4ccccn4)c3)c(Cl)c2)cc1]

266

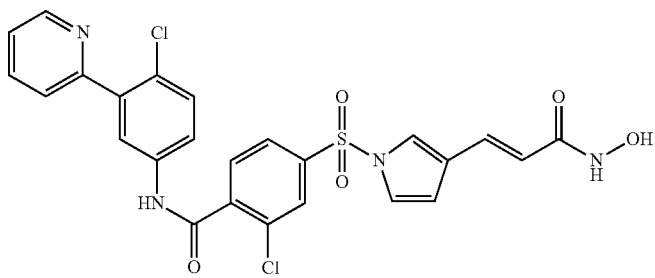 [SMILES: O=C(/C=C/c1ccn(S(=O)(=O)c2ccc(C(=O)Nc3ccc(Cl)c(-c4ccccn4)c3)c(Cl)c2)c1)NO]

267

The invention further provides methods for the prevention or treatment of hedgehog-related diseases or disorders, and in particular, diseases or disorders involving aberrant proliferation, differentiation or survival of cells. In one embodiment, the invention further provides for the use of one or more compounds of the invention in the manufacture of a medicament for halting or decreasing diseases involving aberrant proliferation, differentiation, or survival of cells. In preferred embodiments, the disease is cancer. In one embodiment, the invention relates to a method of treating cancer in a subject in need of treatment comprising administering to said subject a therapeutically effective amount of a compound of the invention. In another embodiment, the invention further provides methods for the prevention or treatment of non-cancer hedgehog-related diseases or disorders, such as psoriasis. The compounds of the invention can also be used to treat diseases or disorders associated with aberrant or uncontrolled angiogenesis, including macular degeneration, diabetic retinopathy, retinopathy of prematurity, rheumatoid arthritis and obesity. In addition, compounds of the invention may be used to down-regulate hair growth.

By virtue of the dual HDAC and Hedgehog inhibitory activities of the compounds of the present invention, the invention further provides a method for treating certain cancers which are resistant to the action of Hedgehog pathway signaling inhibitors alone. Such resistance may be characterized by one or more mutations in proteins involved in the Hedgehog signaling cascade above the level of Gli transcription activation. The present compounds having HDAC inhibiting activity may nonetheless be useful for treating cancers having increased hedgehog levels by inhibiting the deacetylation of the Gli1 and Gli2 transcription activators.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non small cell), breast cancer, pancreatic cancer, melanoma and other skin cancers, stomach cancer, brain tumors, tumors related to Gorlin's syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

In preferred embodiments, the cancer is associated with aberrant hedgehog signaling, for example, when Patched fails to, or inadequately, represses Smoothened (Ptc loss of function phenotype) and/or when Smoothened is active regardless of Patched repression (Smo gain-of function phenotype) and/or when the Hedgehog ligand is upregulated regardless of patched or smoothened mutational status. Examples of such cancer types include basal cell carcinoma, neuroectodermal tumors, such as medulloblastoma, meningioma, hemangioma, glioblastoma, pancreatic adenocarcinoma, squamous lung carcinoma, small cell lung cancer, non-small cell lung cancer, ovarian cancer, prostate cancer, liver cancer, chondrosarcoma, breast carcinoma, rhabdomyosarcoma, esophageal cancer, stomach cancer, biliary tract cancer, renal carcinoma and thyroid carcinoma. Furthermore, compounds of the invention may be useful in the treatment of hematologic tumors such as leukemias, lymphomas and myelomas as listed above.

Additional cancers that the compounds described herein may be useful in treating are, for example, colon carcinoma, familiary adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma.

In one aspect of the invention, the present invention provides for the use of one or more compounds of the invention in the manufacture of a medicament for the treatment of cancer.

In one embodiment, the present invention includes the use of one or more compounds of the invention in the manufacture of a medicament that prevents further aberrant proliferation, differentiation, or survival of cells. For example, compounds of the invention may be useful in preventing tumors from increasing in size or from reaching a metastatic state. The subject compounds may be administered to halt the progression or advancement of cancer or to induce tumor apoptosis or to inhibit tumor angiogenesis. In addition, the instant invention includes use of the subject compounds to prevent a recurrence of cancer.

This invention further embraces the treatment or prevention of cell proliferative disorders such as hyperplasias, dysplasias and pre-cancerous lesions. Dysplasia is the earliest form of pre-cancerous lesion recognizable in a biopsy by a pathologist. The subject compounds may be administered for the purpose of preventing said hyperplasias, dysplasias or pre-cancerous lesions from continuing to expand or from becoming cancerous. Examples of pre-cancerous lesions may occur in skin, esophageal tissue, breast and cervical intra-epithelial tissue.

"Combination therapy" includes the administration of the subject compounds in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, preferably compounds that are able to enhance the effect of the compounds of the invention. The compounds of the invention can be administered simultaneously (as a single preparation or separate preparation) or sequentially to the other drug therapy. In general, a combination therapy envisions administration of two or more drugs during a single cycle or course of therapy.

In one aspect of the invention, the subject compounds may be administered in combination with one or more separate agents that modulate protein kinases involved in various disease states or targets downstream thereof. Examples of such kinases may include, but are not limited to: serine/threonine specific kinases, receptor tyrosine specific kinases and non-receptor tyrosine specific kinases. Serine/threonine kinases include mitogen activated protein kinases (MAPK), meiosis specific kinase (MEK), RAF and aurora kinase. Examples of receptor kinase families include epidermal growth factor receptor (EGFR) (e.g., HER2/neu, HER3, HER4, ErbB, ErbB2, ErbB3, ErbB4, Xmrk, DER, Let23); fibroblast growth factor (FGF) receptor (e.g., FGF-R1, GFF-R2/BEK/CEK3, FGF-R3/CEK2, FGF-R4/TKF, KGF-R); hepatocyte growth/scatter factor receptor (HGFR) (e.g., MET, RON, SEA, SEX); insulin receptor (e.g., IGFI-R, PI3K, AKT, mTor); Eph (e.g., CEKS, CEK8, EBK, ECK, EEK, EHK-1, EHK-2, ELK, EPH, ERK, HEK, MDK2, MDK5, SEK); Axl (e.g., Mer/Nyk, Rse); RET; and platelet-derived growth factor receptor (PDGFR) (e.g., PDGFα-R, PDGFβ-R, CSF1-R/FMS, SCF-R/C-KIT, VEGF-R/FLT, NEK/FLK1, FLT3/FLK2/STK-1). Non-receptor tyrosine kinase families include, but are not limited to, BCR-ABL (e.g., p43$^{ab1}$, ARG); BTK (e.g., ITK/EMT, TEC); CSK, FAK, FPS, JAK, SRC, BMX, FER, CDK and SYK.

In another aspect of the invention, the subject compounds may be administered in combination with one or more separate agents that modulate non-kinase biological targets or processes. Such targets include histone deacetylases (HDAC), DNA methyltransferase (DNMT), heat shock proteins (e.g., HSP90), and proteosomes.

In a preferred embodiment, subject compounds may be combined with antineoplastic agents (e.g., small molecules, monoclonal antibodies, antisense RNA, and fusion proteins) that inhibit one or more biological targets such as Zolinza, Tarceva, Iressa, Tykerb, Gleevec, Sutent, Sprycel, Nexavar, CNF2024, RG108, BMS387032, Affinitak, Avastin, Herceptin, Erbitux, AG24322, PD325901, ZD6474, PD184322, Obatodax, ABT737 and AEE788. Such combinations may enhance therapeutic efficacy over efficacy achieved by any of the agents alone and may prevent or delay the appearance of resistant mutational variants. For example, the subject compounds may advantageously be used in combination with a BCL-ABL inhibitor such as Sprycel for the treatment of hematologic tumors such as leukemias, lymphomas and myelomas.

In certain preferred embodiments, the compounds of the invention are administered in combination with a chemotherapeutic agent. Chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as mustard gas derivatives (Mechlorethamine, cylophosphamide, chlorambucil, melphalan, ifosfamide), ethylenimines (thiotepa, hexamethylmelanine), Alkylsulfonates (Busulfan), Hydrazines and Triazines (Altretamine, Procarbazine, Dacarbazine and Temozolomide), Nitrosoureas (Carmustine, Lomustine and Streptozocin), Ifosfamide and metal salts (Carboplatin, Cisplatin, and Oxaliplatin); plant alkaloids such as Podophyllotoxins (Etoposide and Tenisopide), Taxanes (Paclitaxel and Docetaxel), *Vinca* alkaloids (Vincristine, Vinblastine, Vindesine and Vinorelbine), and Camptothecan analogs (Irinotecan and Topotecan); anti-tumor antibiotics such as Chromomycins (Dactinomycin and Plicamycin), Anthracyclines (Doxorubicin, Daunorubicin, Epirubicin, Mitoxantrone, Valrubicin and Idarubicin), and miscellaneous antibiotics such as Mitomycin, Actinomycin and Bleomycin; anti-metabolites such as folic acid antagonists (Methotrexate, Pemetrexed, Raltitrexed, Aminopterin), pyrimidine antagonists (5-Fluorouracil, Floxuridine, Cytarabine, Capecitabine, and Gemcitabine), purine antagonists (6-Mercaptopurine and 6-Thioguanine) and adenosine deaminase inhibitors (Cladribine, Fludarabine, Mercaptopurine, Clofarabine, Thioguanine, Nelarabine and Pentostatin); topoisomerase inhibitors such as topoisomerase I inhibitors (Ironotecan, topotecan) and topoisomerase II inhibitors (Amsacrine, etoposide, etoposide phosphate, teniposide); monoclonal antibodies (Alemtuzumab, Gemtuzumab ozogamicin, Rituximab, Trastuzumab, Ibritumomab Tioxetan, Cetuximab, Panitumumab, Tositumomab, Bevacizumab); and miscellaneous anti-neoplastics such as ribonucleotide reductase inhibitors (Hydroxyurea); adrenocortical steroid inhibitor (Mitotane); enzymes (Asparaginase and Pegaspargase); anti-microtubule agents (Estramustine); and retinoids (Bexarotene, Isotretinoin, Tretinoin (ATRA). For example, the subject compounds may advantageously be used in combination with a pyrimidine antagonist such as Gemcitabine for the treatment of solid tumors such as pancreatic cancers such as pancreatic adenocarcinoma.

In certain preferred embodiments, the compounds of the invention are administered in combination with a chemoprotective agent. Chemoprotective agents act to protect the body or minimize the side effects of chemotherapy. Examples of such agents include, but are not limited to, amfostine, mesna, and dexrazoxane.

In one aspect of the invention, the subject compounds are administered in combination with radiation therapy. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

It will be appreciated that compounds of the invention can be used in combination with an immunotherapeutic agent. One form of immunotherapy is the generation of an active systemic tumor-specific immune response of host origin by administering a vaccine composition at a site distant from the tumor. Various types of vaccines have been proposed, including isolated tumor-antigen vaccines and anti-idiotype vaccines. Another approach is to use tumor cells from the subject to be treated, or a derivative of such cells (reviewed by Schirrmacher et al. (1995) J. Cancer Res. Clin. Oncol., 121:487). In U.S. Pat. No. 5,484,596, Hanna Jr. et al. claim a method for treating a resectable carcinoma to prevent recurrence or metastases, comprising surgically removing the tumor, dispersing the cells with collagenase, irradiating the cells, and vaccinating the patient with at least three consecutive doses of about $10^7$ cells.

It will be appreciated that the compounds of the invention may advantageously be used in conjunction with one or more adjunctive therapeutic agents. Examples of suitable agents for adjunctive therapy include a $5HT_1$ agonist, such as a triptan (e.g. sumatriptan or naratriptan); an inhibitor of the phosphoinositol-3-kinase (PI3K) family; an inhibitor of the mammalian target of rapamycin (mTOR); an inhibitor of Bcr-Abl; an adenosine A1 agonist; an EP ligand; an NMDA modulator, such as a glycine antagonist; a sodium channel blocker (e.g. lamotrigine); a substance P antagonist (e.g. an NKi antagonist); a cannabinoid; acetaminophen or phenacetin; a 5-lipoxygenase inhibitor; a leukotriene receptor antagonist; a DMARD (e.g. methotrexate); gabapentin and related compounds; a tricyclic antidepressant (e.g. amitryptilline); a neuron stabilising antiepileptic drug; a monoaminergic uptake inhibitor (e.g. venlafaxine); a matrix metalloproteinase inhibitor; a nitric oxide synthase (NOS) inhibitor, such as an iNOS or an nNOS inhibitor; an inhibitor of the release, or action, of tumour necrosis factor alpha; an antibody therapy, such as a monoclonal antibody therapy; an antiviral agent, such as a nucleoside inhibitor (e.g. lamivudine) or an immune system modulator (e.g. interferon); an opioid analgesic; a local anaesthetic; a stimulant, including caffeine; an $H_2$-antagonist (e.g. ranitidine); a proton pump inhibitor (e.g. omeprazole); an antacid (e.g. aluminium or magnesium hydroxide; an antiflatulent (e.g. simethicone); a decongestant (e.g. phenylephrine, phenylpropanolamine, pseudoephedrine, oxymetazoline, epinephrine, naphazoline, xylometazoline, propylhexedrine, or levo-desoxyephedrine); an antitussive (e.g. codeine, hydrocodone, carmiphen, carbetapentane, or dextramethorphan); a diuretic; or a sedating or non-sedating antihistamine.

The compounds may also be used in the treatment of a disorder involving, relating to or, associated with dysregulation of histone deacetylase (HDAC). There are a number of disorders that have been implicated by or known to be mediated at least in part by HDAC activity, where HDAC activity is known to play a role in triggering disease onset, or whose symptoms are known or have been shown to be alleviated by HDAC inhibitors. Disorders of this type that would be expected to be amenable to treatment with the compounds of the invention include the following but not limited to: Anti-proliferative disorders (e.g. cancers); Neurodegenerative diseases including Huntington's Disease, Polyglutamine disease, Parkinson's Disease, Alzheimer's Disease, Seizures, Striatonigral degeneration, Progressive supranuclear palsy, Torsion dystonia, Spasmodic torticollis and dyskinesis, Familial tremor, Gilles de la Tourette syndrome, Diffuse Lewy body disease, Progressive supranuclear palsy, Pick's disease, intracerebral hemorrhage, Primary lateral sclerosis, Spinal muscular atrophy, Amyotrophic lateral sclerosis, Hypertrophic interstitial polyneuropathy, Retinitis pigmentosa, Hereditary optic atrophy, Hereditary spastic paraplegia, Progressive ataxia and Shy-Drager syndrome; Metabolic diseases including Type 2 diabetes; Degenerative Diseases of the Eye including Glaucoma, Age-related macular degeneration, Rubeotic glaucoma; Inflammatory diseases and/or Immune system disorders including Rheumatoid Arthritis (RA), Osteoarthritis, Juvenile chronic arthritis, Graft versus Host disease, Psoriasis, Asthma, Spondyloarthropathy, Crohn's Disease, inflammatory bowel disease Colitis Ulcerosa, Alcoholic hepatitis, Diabetes, Sjoegrens's syndrome, Multiple Sclerosis, Ankylosing spondylitis, Membranous glomerulopathy, Discogenic pain, Systemic Lupus Erythematosus; Disease involving angiogenesis including cancer, psoriasis, rheumatoid arthritis; Psychological disorders including bipolar disease, schizophrenia, mania, depression and dementia; Cardiovascular Diseases including the prevention and treatment of ischemia-related or reperfusion-related vascular and myocardial tissue damage, heart failure, restenosis and arteriosclerosis; Fibrotic diseases including liver fibrosis, cystic fibrosis and angiofibroma; Infectious diseases including Fungal infections, such as candidiasis or *Candida Albicans*, Bacterial infections, Viral infections, such as Herpes Simplex, poliovirus, rhinovirus and coxsackievirus, Protozoal infections, such as Malaria, *Leishmania* infection, *Trypanosoma brucei* infection, Toxoplasmosis and coccidlosis and Haematopoietic disorders including thalassemia, anemia and sickle cell anemia.

Compounds of the invention inhibit angiongenesis and are therefore useful in the treatment of diseases or conditions mediated by angiogenesis such as tumors, in particular solid tumors such as colon, lung, pancreatic, ovarian, breast and glioma. Furthermore, compounds of the invention are useful for treating macular degeneration, e.g., wet age-related macular degeneration. Compounds of the invention are also useful for treating inflammatory/immune diseases such as Crohn's disease, inflammatory bowel disease, Sjogren's syndrome, asthma, organ transplant rejection, systemic lupus erythematoses, psoriatic arthritis, psoriasis and multiple sclerosis. The compounds can also be used for the downregulation of hair growth or as a depilatory for cosmetic purposes or in the treatment of hirsutism.

The invention encompasses pharmaceutical compositions comprising pharmaceutically acceptable salts of the compounds of the invention as described above. The invention also encompasses solvates of the compounds of the invention and pharmaceutical compositions comprising such solvates, such as hydrates, methanolates or ethanolates. The term "solvate" refers to a solid, preferably crystalline, form of a compound which includes the presence of solvent molecules within the crystal lattice. A solvate of a compound comprising a given solvent is typically prepared by crystallization of the compound from that solvent. Solvates can include a variety of solvents, including water, methanol and ethanol. The term "hydrate" refers to a solvate in which the solvent is water, and includes, but is not limited to, hemihydrate, monohydrate, dihydrate, trihydrate and the like. The invention further encompasses pharmaceutical compositions comprising any solid or liquid physical form of the compound of the invention, including crystalline and crystalline solvate forms. For example, the compounds can be in a crystalline form, in amorphous form, and have any particle size. The particles may be micronized, or may be agglomerated, particulate granules, powders, oils, oily suspensions or any other -solid or liquid physical form.

The compounds of the invention, and derivatives, fragments, analogs, homologs, pharmaceutically acceptable salts or solvates thereof can be incorporated into pharmaceutical compositions suitable for administration, together with a pharmaceutically acceptable carrier or excipient. Such compositions typically comprise a therapeutically effective amount of any of the compounds above, and a pharmaceutically acceptable carrier. Preferably, the effective amount when treating cancer is an amount effective to selectively induce terminal differentiation of suitable neoplastic cells and less than an amount which causes toxicity in a patient.

Compounds of the invention may be administered by any suitable means, including, without limitation, parenteral, intravenous, intramuscular, subcutaneous, implantation, oral, sublingual, buccal, nasal, pulmonary, transdermal, topical, vaginal, rectal, and transmucosal administrations or the like. Topical administration can also involve the use of transdermal administration such as transdermal patches or iontophoresis devices. Pharmaceutical preparations include a solid, semisolid or liquid preparation (tablet, pellet, troche, capsule, suppository, cream, ointment, aerosol, powder, liquid, emulsion, suspension, syrup, injection etc.) containing a compound of the invention as an active ingredient, which is suitable for selected mode of administration. In one embodiment, the pharmaceutical compositions are administered orally, and are thus formulated in a form suitable for oral administration, i.e., as a solid or a liquid preparation. Suitable solid oral formulations include tablets, capsules, pills, granules, pellets, sachets and effervescent, powders, and the like. Suitable liquid oral formulations include solutions, suspensions, dispersions, emulsions, oils and the like. In one embodiment of the present invention, the composition is formulated in a capsule. In accordance with this embodiment, the compositions of the present invention comprise in addition to the active compound and the inert carrier or diluent, a hard gelatin capsule.

Any inert excipient that is commonly used as a carrier or diluent may be used in the formulations of the present invention, such as for example, a gum, a starch, a sugar, a cellulosic material, an acrylate, or mixtures thereof. A preferred diluent is microcrystalline cellulose. The compositions may further comprise a disintegrating agent (e.g., croscarmellose sodium) and a lubricant (e.g., magnesium stearate), and may additionally comprise one or more additives selected from a binder, a buffer, a protease inhibitor, a surfactant, a solubilizing agent, a plasticizer, an emulsifier, a stabilizing agent, a viscosity increasing agent, a sweetener, a film forming agent, or any combination thereof. Furthermore, the compositions of the present invention may be in the form of controlled release or immediate release formulations.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

In addition, the compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Daily administration may be repeated continuously for a period of several days to several years. Oral treatment may continue for between one week and the life of the patient. Preferably the administration may take place for five consecutive days after which time the patient can be evaluated to determine if further administration is required. The administration can be continuous or intermittent, e.g., treatment for a number of consecutive days followed by a rest period. The compounds of the present invention may be administered intravenously on the first day of treatment, with oral administration on the second day and all consecutive days thereafter.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions and the like as detailed above.

The amount of the compound administered to the patient is less than an amount that would cause toxicity in the patient. In certain embodiments, the amount of the compound that is administered to the patient is less than the amount that causes a concentration of the compound in the patient's plasma to equal or exceed the toxic level of the compound. Preferably, the concentration of the compound in the patient's plasma is maintained at about 10 nM. In one embodiment, the concentration of the compound in the patient's plasma is maintained at about 25 nM. In one embodiment, the concentration of the compound in the patient's plasma is maintained at about 50 nM. In one embodiment, the concentration of the compound in the patient's plasma is maintained at about 100 nM. In one embodiment, the concentration of the compound in the patient's plasma is maintained at about 500 nM. In one embodiment, the concentration of the compound in the patient's plasma is maintained at about 1000 nM. In one embodiment, the concentration of the compound in the patient's plasma is maintained at about 2500 nM. In one embodiment, the concentration of the compound in the patient's plasma is maintained at about 5000 nM. The optimal amount of the compound that should be administered to the patient in the practice of the present invention will depend on the particular compound used and the type of cancer being treated.

Definitions

Listed below are definitions of various terms used to describe this invention. These definitions apply to the terms as they are used throughout this specification and claims, unless otherwise limited in specific instances, either individually or as part of a larger group.

An "aliphatic group" or "aliphatic" is non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. An aliphatic group, when used as a linker, preferably contains between about 1 and about 24 atoms, more preferably between about 4 to about 24 atoms, more preferably between about 4-12 atoms, more typically between about 4 and about 8 atoms. An aliphatic group, when used as a substituent, preferably contains between about 1 and about 24 atoms, more preferably between about 1 to about 10 atoms, more preferably between about 1-8 atoms, more typically between about 1 and about 6 atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl groups described herein.

The term "substituted carbonyl" includes compounds and moieties which contain a carbon connected with a double bond to an oxygen atom, and tautomeric forms thereof. Examples of moieties that contain a substituted carbonyl include aldehydes, ketones, carboxylic acids, amides, esters, anhydrides, etc. The term "carbonyl moiety" refers to groups such as "alkylcarbonyl" groups wherein an alkyl group is covalently bound to a carbonyl group, "alkenylcarbonyl" groups wherein an alkenyl group is covalently bound to a carbonyl group, "alkynylcarbonyl" groups wherein an alkynyl group is covalently bound to a carbonyl group, "arylcarbonyl" groups wherein an aryl group is covalently attached to the carbonyl group. Furthermore, the term also refers to groups wherein one or more heteroatoms are covalently bonded to the carbonyl moiety. For example, the term includes moieties such as, for example, aminocarbonyl moieties, (wherein a nitrogen atom is bound to the carbon of the carbonyl group, e.g., an amide).

The term "acyl" refers to hydrogen, alkyl, partially saturated or fully saturated cycloalkyl, partially saturated or fully saturated heterocycle, aryl, and heteroaryl substituted carbonyl groups. For example, acyl includes groups such as ($C_1$-$C_6$)alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about eight carbon atoms. Examples of such radicals include methyl, ethyl, n-propyl, isopropyl, n-butyl, isobutyl, sec-butyl, tert-butyl, pentyl, iso-amyl, hexyl and the like.

The term "alkenyl" embraces linear or branched radicals having at least one carbon-carbon double bond of two to about twenty carbon atoms or, preferably, two to about twelve carbon atoms. More preferred alkenyl radicals are "lower alkenyl" radicals having two to about ten carbon atoms and more preferably about two to about eight carbon atoms. Examples of alkenyl radicals include ethenyl, allyl, propenyl, butenyl and 4-methylbutenyl. The terms "alkenyl", and "lower alkenyl", embrace radicals having "cis" and "trans" orientations, or alternatively, "E" and "Z" orientations.

The term "alkynyl" embraces linear or branched radicals having at least one carbon-carbon triple bond of two to about twenty carbon atoms or, preferably, two to about twelve carbon atoms. More preferred alkynyl radicals are "lower alkynyl" radicals having two to about ten carbon atoms and more preferably about two to about eight carbon atoms. Examples of alkynyl radicals include propargyl, 1-propynyl, 2-propynyl, 1-butyne, 2-butynyl and 1-pentynyl.

The term "cycloalkyl" embraces saturated carbocyclic radicals having three to about twelve carbon atoms. The term "cycloalkyl" embraces saturated carbocyclic radicals having three to about twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl.

The term "cycloalkenyl" embraces partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkoxy" embraces linear or branched oxy-containing radicals each having alkyl portions of one to about twenty carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" embraces alkyl radicals having one or more alkoxy radicals attached to the alkyl radical, that is, to form monoalkoxyalkyl and dialkoxyalkyl radicals.

The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl.

The terms "heterocyclyl", "heterocycle" "heterocyclic" or "heterocyclo" embrace saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" embraces unsaturated heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" embraces heterocyclo-substituted alkyl radicals. More preferred heterocycloalkyl radicals are "lower heterocycloalkyl" radicals having one to six carbon atoms in the heterocyclo radicals.

The term "alkylthio" embraces radicals containing a linear or branched alkyl radical, of one to about ten carbon atoms attached to a divalent sulfur atom. Preferred alkylthio radicals have alkyl radicals of one to about twenty carbon atoms or, preferably, one to about twelve carbon atoms. More preferred alkylthio radicals have alkyl radicals are "lower alkylthio" radicals having one to about ten carbon atoms. Most preferred are alkylthio radicals having lower alkyl radicals of one to about eight carbon atoms. Examples of such lower alkylthio radicals are methylthio, ethylthio, propylthio, butylthio and hexylthio.

The terms "aralkyl" or "arylalkyl" embrace aryl-substituted alkyl radicals such as benzyl, diphenylmethyl, triphenylmethyl, phenylethyl, and diphenylethyl.

The term "aryloxy" embraces aryl radicals attached through an oxygen atom to other radicals.

The terms "aralkoxy" or "arylalkoxy" embrace aralkyl radicals attached through an oxygen atom to other radicals.

The term "aminoalkyl" embraces alkyl radicals substituted with amino radicals. Preferred aminoalkyl radicals have alkyl radicals having about one to about twenty carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

The term "linker" means an organic moiety that connects two parts of a compound. Linkers typically comprise a direct bond or an atom such as oxygen or sulfur, a unit such as $NR_2$, $C(O)$, $C(O)NH$, $SO$, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, $N(R_2)$, $C(O)$, substituted or unsubstituted aryl, substituted or unsubstituted heteroaryl, substituted or unsubstituted heterocyclic; where $R_2$ is hydrogen, acyl, aliphatic or substituted aliphatic. In one embodiment, the linker B is between 1-24 atoms in length, preferably 4-24 atoms in length, preferably 4-18 atoms in length, more preferably 4-12 atoms in length, and most preferably about 4-10 atoms in length. In some embodiments, the linker is a C(O)NH(alkyl) chain or an alkoxy chain. It is to be understood that an asymmetric linker, such as alkylaryl, can connect two structurally distinct moieties in either of its two possible orientations.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkyl sulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

As used herein, the term "aberrant proliferation" refers to abnormal cell growth.

The phrase "adjunctive therapy" encompasses treatment of a subject with agents that reduce or avoid side effects associated with the combination therapy of the present invention, including, but not limited to, those agents, for example, that reduce the toxic effect of anticancer drugs, e.g., bone resorption inhibitors, cardioprotective agents; prevent or reduce the incidence of nausea and vomiting associated with chemotherapy, radiotherapy or operation; or reduce the incidence of infection associated with the administration of myelosuppressive anticancer drugs.

The term "angiogenesis," as used herein, refers to the formation of blood vessels. Specifically, angiogenesis is a multi-step process in which endothelial cells focally degrade and invade through their own basement membrane, migrate through interstitial stroma toward an angiogenic stimulus, proliferate proximal to the migrating tip, organize into blood vessels, and reattach to newly synthesized basement membrane (see Folkman et al., Adv. Cancer Res., Vol. 43, pp. 175-203 (1985)). Anti-angiogenic agents interfere with this process. Examples of agents that interfere with several of these steps include thrombospondin-1, angiostatin, endostatin, interferon alpha and compounds such as matrix metalloproteinase (MMP) inhibitors that block the actions of enzymes that clear and create paths for newly forming blood vessels to follow; compounds, such as .alpha.v.beta.3 inhibitors, that interfere with molecules that blood vessel cells use to bridge between a parent blood vessel and a tumor; agents, such as specific COX-2 inhibitors, that prevent the growth of cells that form new blood vessels; and protein-based compounds that simultaneously interfere with several of these targets.

The term "apoptosis" as used herein refers to programmed cell death as signaled by the nuclei in normally functioning human and animal cells when age or state of cell health and condition dictates. An "apoptosis inducing agent" triggers the process of programmed cell death.

The term "cancer" as used herein denotes a class of diseases or disorders characterized by uncontrolled division of cells and the ability of these cells to invade other tissues, either by direct growth into adjacent tissue through invasion or by implantation into distant sites by metastasis.

The term "compound" is defined herein to include pharmaceutically acceptable salts, solvates, hydrates, polymorphs, enantiomers, diastereoisomers, racemates and the like of the compounds having a formula as set forth herein.

The term "device" refers to any appliance, usually mechanical or electrical, designed to perform a particular function.

As used herein, the term "dysplasia" refers to abnormal cell growth, and typically refers to the earliest form of pre-cancerous lesion recognizable in a biopsy by a pathologist.

As used herein, the term "effective amount of the subject compounds," with respect to the subject method of treatment, refers to an amount of the subject compound which, when delivered as part of desired dose regimen, brings about, e.g. a change in the rate of cell proliferation and/or state of differentiation and/or rate of survival of a cell to clinically acceptable standards. This amount may further relieve to some extent one or more of the symptoms of a neoplasia disorder, including, but is not limited to: 1) reduction in the number of cancer cells; 2) reduction in tumor size; 3) inhibition (i.e., slowing to some extent, preferably stopping) of cancer cell infiltration into peripheral organs; 4) inhibition (i.e., slowing to some extent, preferably stopping) of tumor metastasis; 5) inhibition, to some extent, of tumor growth; 6) relieving or reducing to some extent one or more of the symptoms associated with the disorder; and/or 7) relieving or reducing the side effects associated with the administration of anticancer agents.

The term "hyperplasia," as used herein, refers to excessive cell division or growth.

The phrase an "immunotherapeutic agent" refers to agents used to transfer the immunity of an immune donor, e.g., another person or an animal, to a host by inoculation. The term embraces the use of serum or gamma globulin containing performed antibodies produced by another individual or an animal; nonspecific systemic stimulation; adjuvants; active specific immunotherapy; and adoptive immunotherapy. Adoptive immunotherapy refers to the treatment of a disease by therapy or agents that include host inoculation of sensitized lymphocytes, transfer factor, immune RNA, or antibodies in serum or gamma globulin.

The term "inhibition," in the context of neoplasia, tumor growth or tumor cell growth, may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, is referred to herein as prevention or chemoprevention.

The term "metastasis," as used herein, refers to the migration of cancer cells from the original tumor site through the blood and lymph vessels to produce cancers in other tissues. Metastasis also is the term used for a secondary cancer growing at a distant site.

The term "neoplasm," as used herein, refers to an abnormal mass of tissue that results from excessive cell division. Neoplasms may be benign (not cancerous), or malignant (cancerous) and may also be called a tumor. The term "neoplasia" is the pathological process that results in tumor formation.

As used herein, the term "pre-cancerous" refers to a condition that is not malignant, but is likely to become malignant if left untreated.

The term "proliferation" refers to cells undergoing mitosis.

The phrase "hedgehog related disease or disorder" refers to a disease or disorder characterized by inappropriate hedgehog signaling activity. Such inappropriate hedgehog signaling activity can occur when Patched fails to, or inadequately, represses Smoothened (Ptc loss of function phenotype) and/or when Smoothened is active regardless of Patched repression (Smo gain-of function phenotype).

The phrase a "radio therapeutic agent" refers to the use of electromagnetic or particulate radiation in the treatment of neoplasia.

The term "recurrence" as used herein refers to the return of cancer after a period of remission. This may be due to incomplete removal of cells from the initial cancer and may occur locally (the same site of initial cancer), regionally (in vicinity of initial cancer, possibly in the lymph nodes or tissue), and/or distally as a result of metastasis.

The term "treatment" refers to any process, action, application, therapy, or the like, wherein a mammal, including a human being, is subject to medical aid with the object of improving the mammal's condition, directly or indirectly.

The term "vaccine" includes agents that induce the patient's immune system to mount an immune response against the tumor by attacking cells that express tumor associated antigens (Teas).

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid or inorganic acid. Examples of pharmaceutically acceptable nontoxic acid addition salts include, but are not limited to, salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid lactobionic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the present invention.

"Prodrug", as used herein, means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed.), "Design and Application of Prodrugs, Textbook of Drug Design and Development, Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

As used herein, "pharmaceutically acceptable carrier" is intended to include any and all solvents, dispersion media, coatings, antibacterial and antifungal agents, isotonic and absorption delaying agents, and the like, compatible with pharmaceutical administration, such as sterile pyrogen-free water. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

As used herein, the term "pre-cancerous" refers to a condition that is not malignant, but is likely to become malignant if left untreated.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds described herein can contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers and/or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; cyclodextrins such as alpha-($\alpha$), beta-($\beta$) and gamma-($\gamma$) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intracisternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43650 by Montgomery, all of which are incorporated herein by reference). A discussion of pulmonary delivery of antibiotics is also found in U.S. Pat. No. 6,014,969, incorporated herein by reference.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Synthetic Methods

The compounds and processes of the present invention will be better understood in connection with the following synthetic schemes and examples that illustrate the methods by which the compounds of the invention may be prepared, which are intended as an illustration only and not limiting of the scope of the invention.

General Methods for the Synthesis of Key Intermediates

Scheme 1

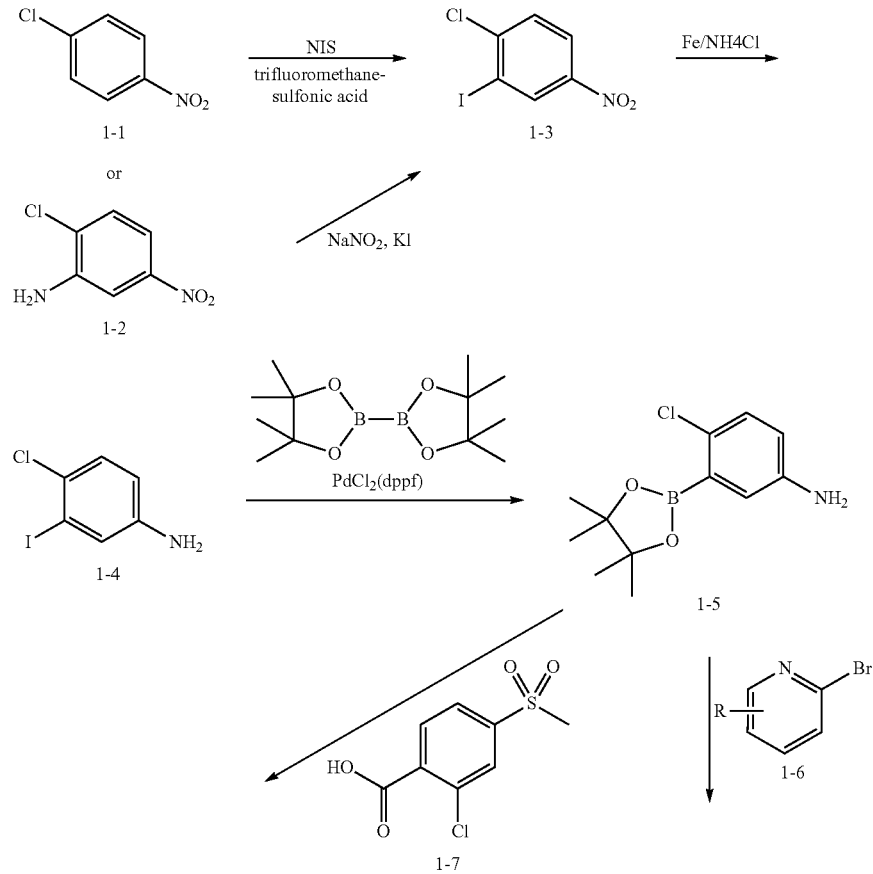

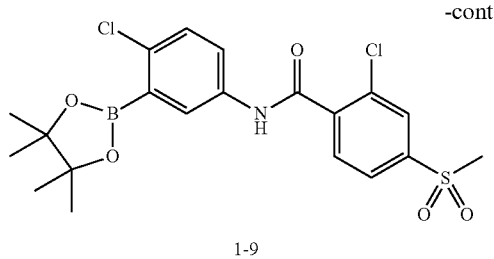
1-9
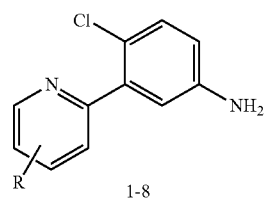
1-8
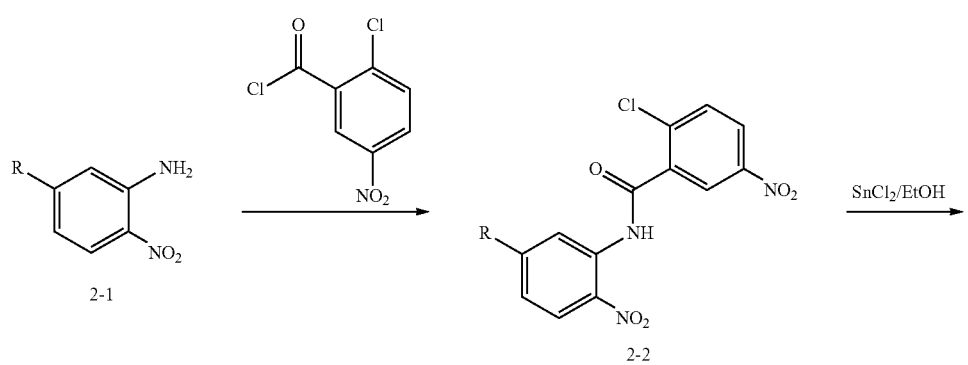
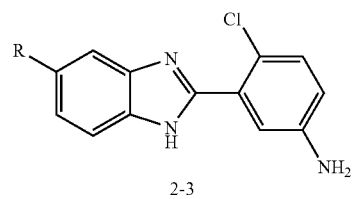
2-3
Scheme 2
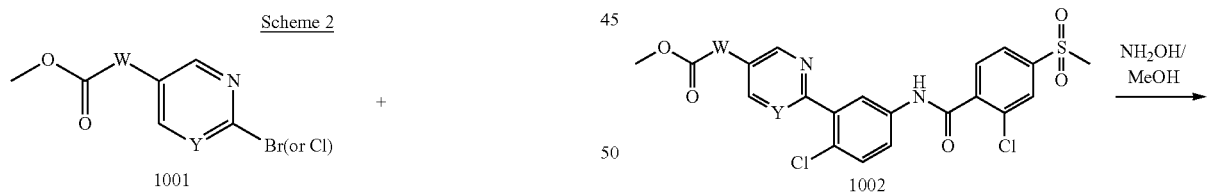
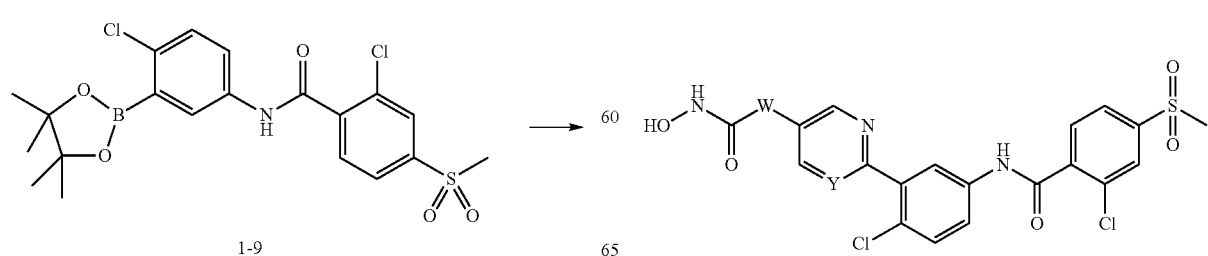

Scheme 3
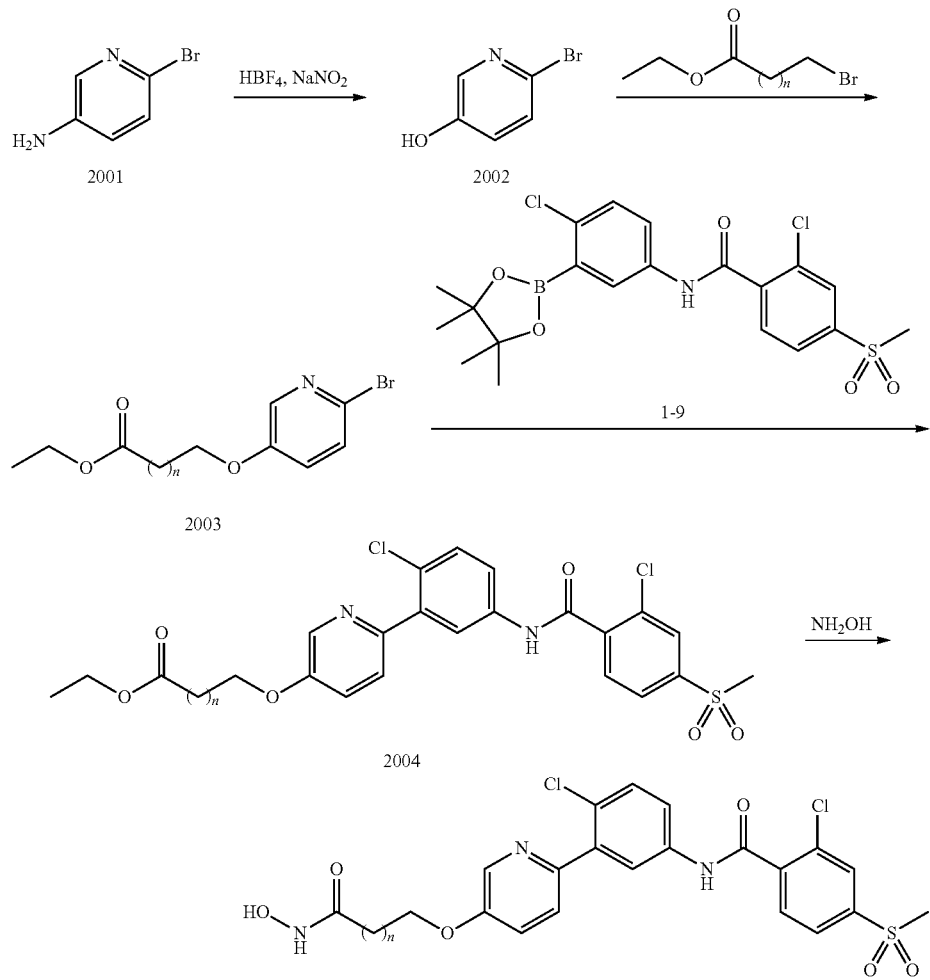
Scheme 4
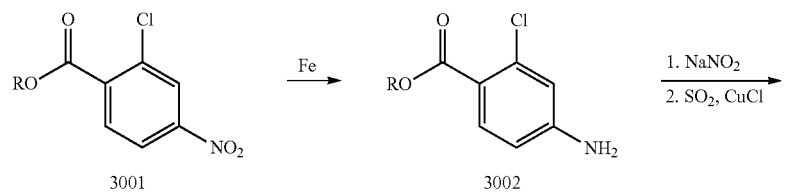
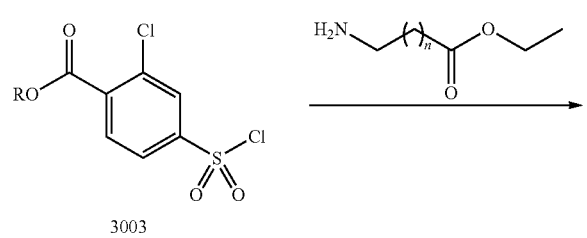

101 102
-continued
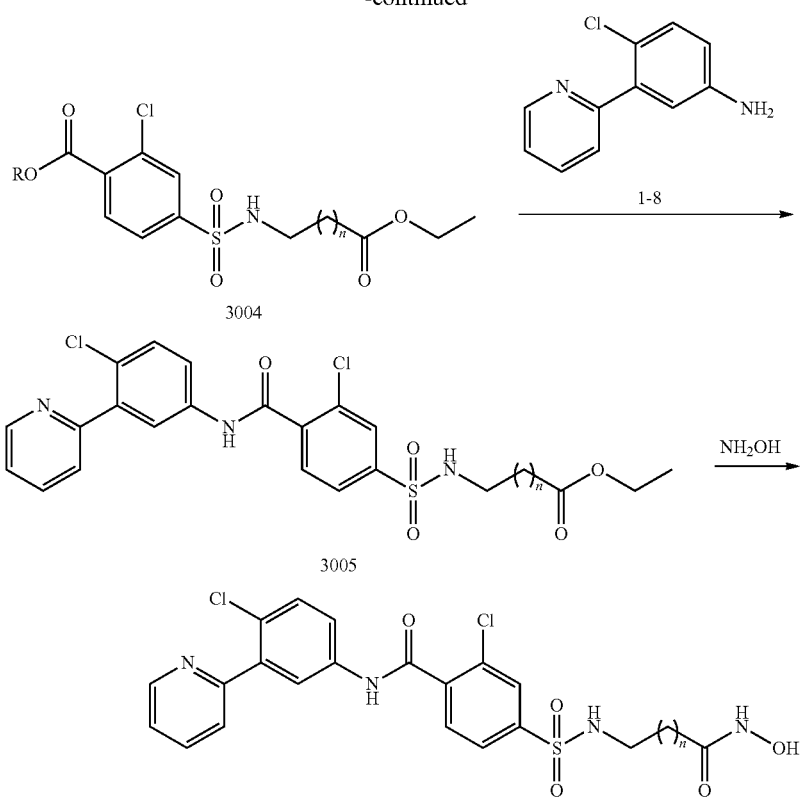
Scheme 5
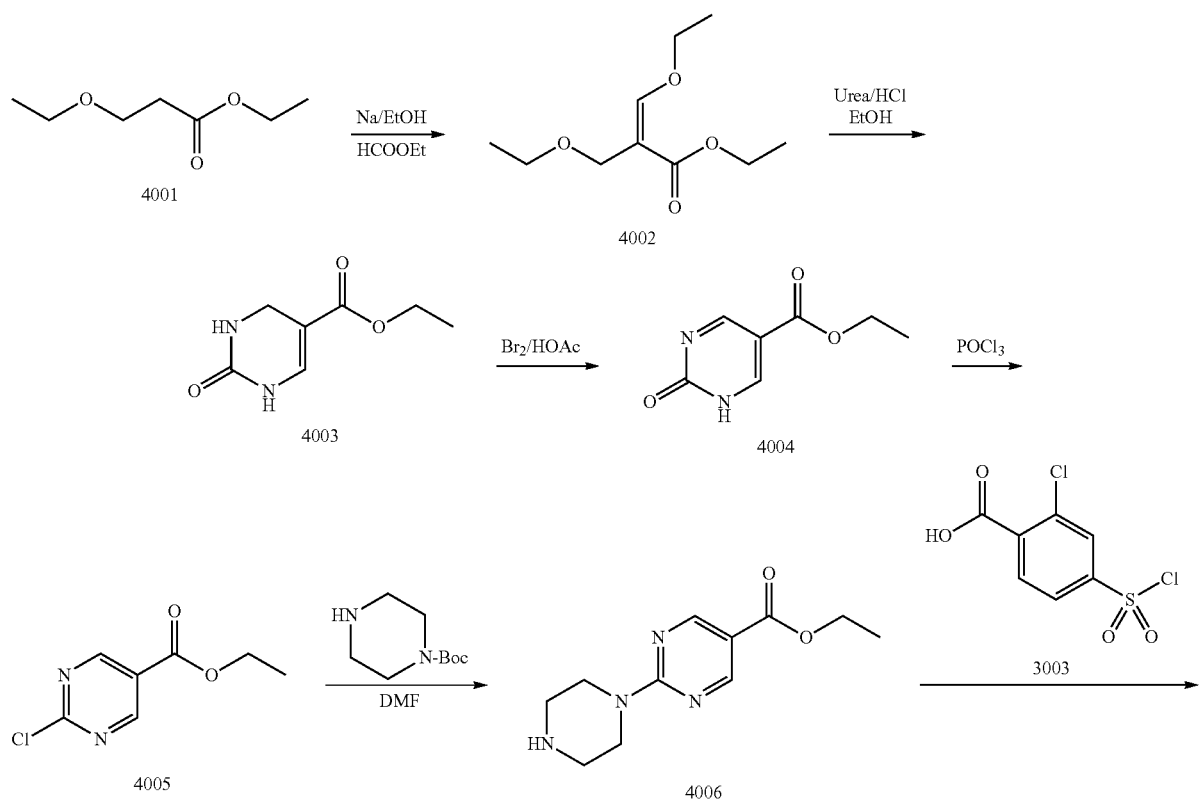

103
104
-continued
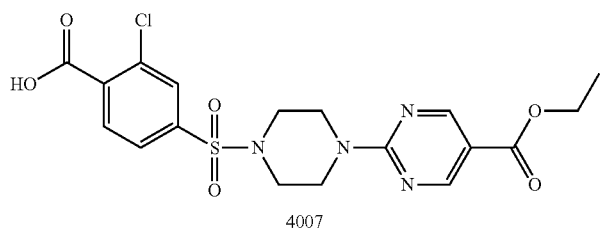
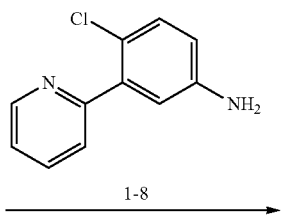
1-8 →
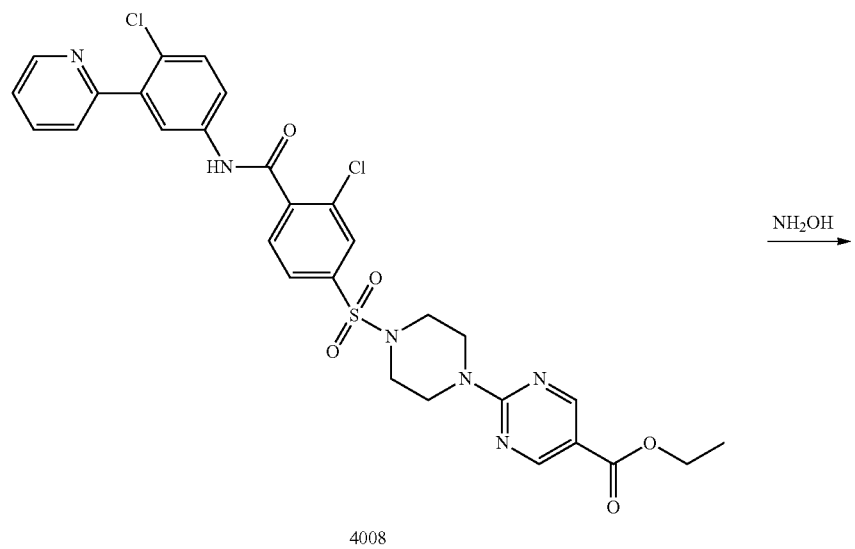
NH₂OH →
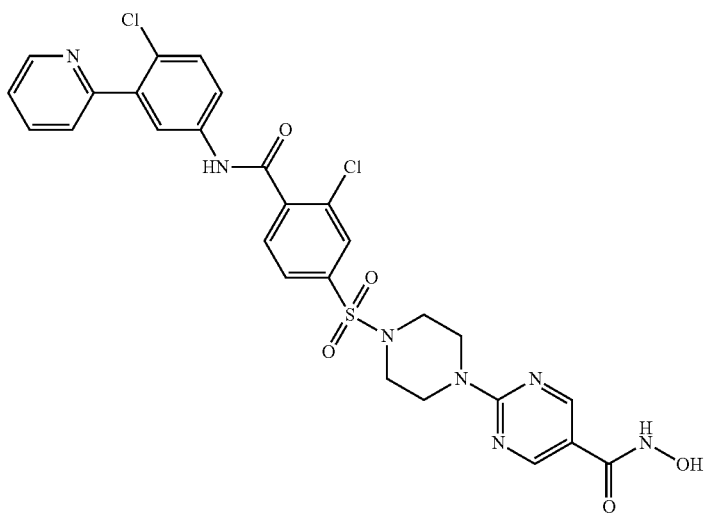

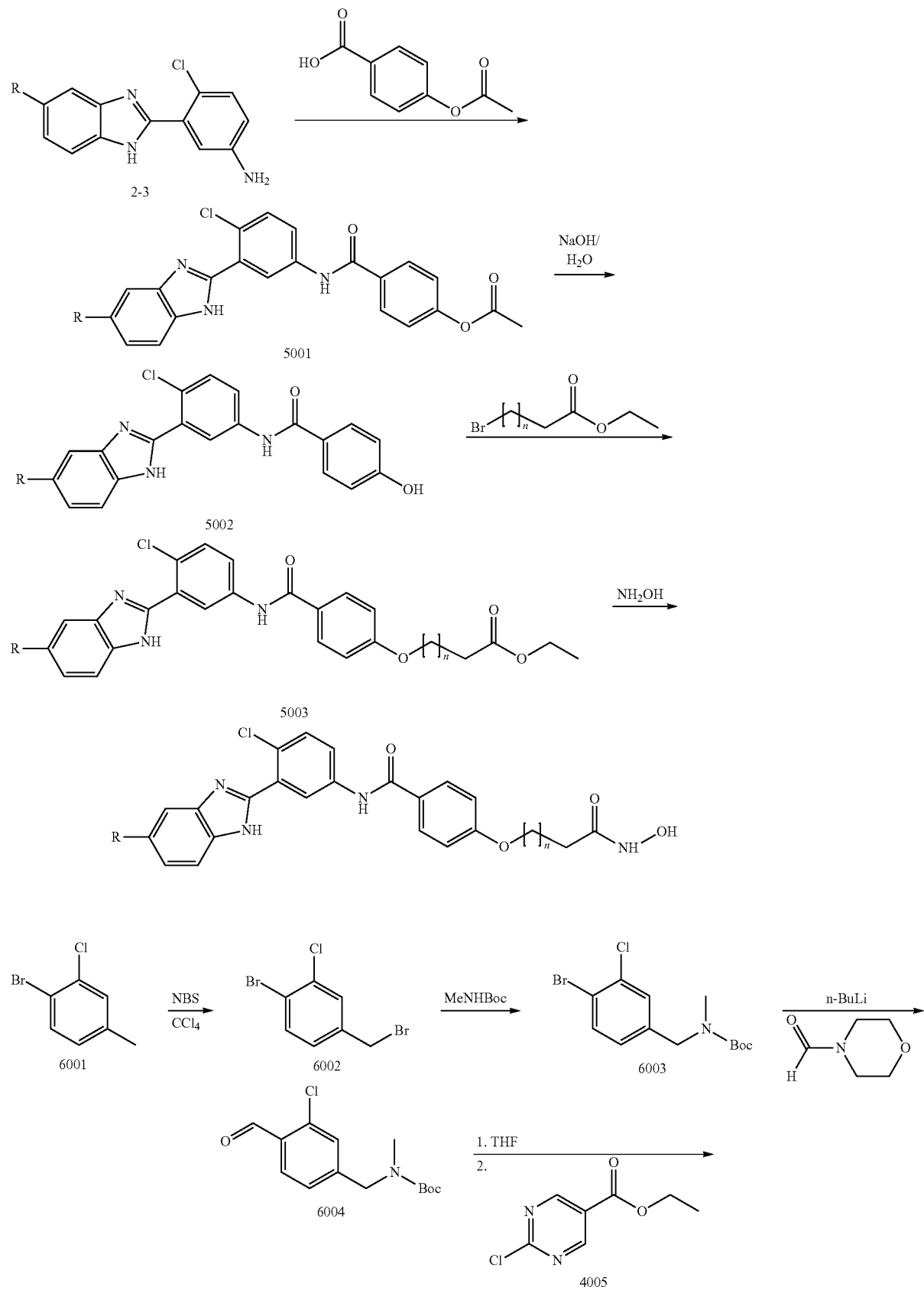

-continued
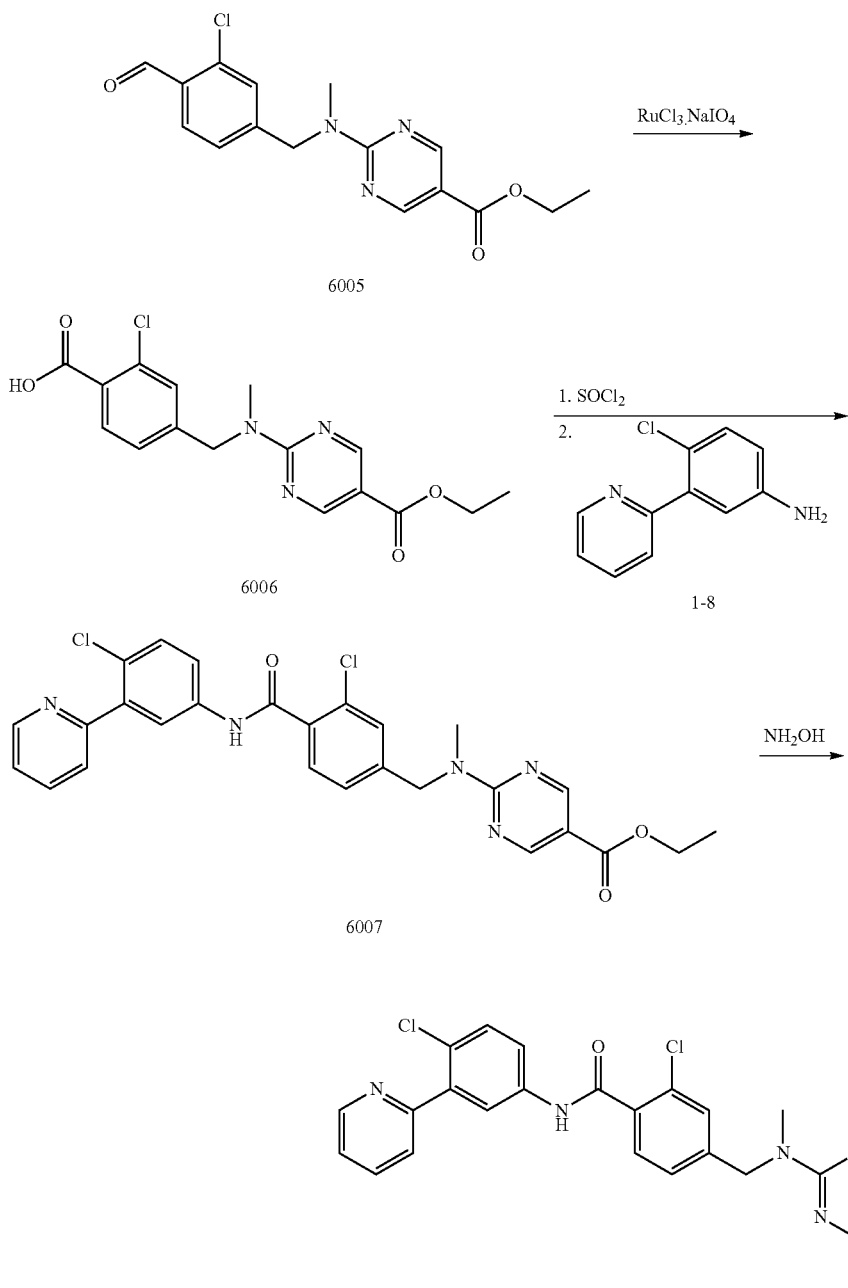
Scheme 8
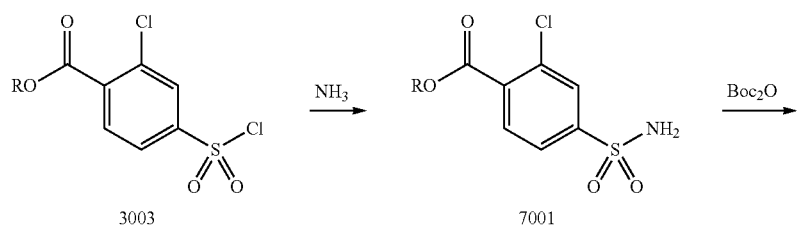

-continued
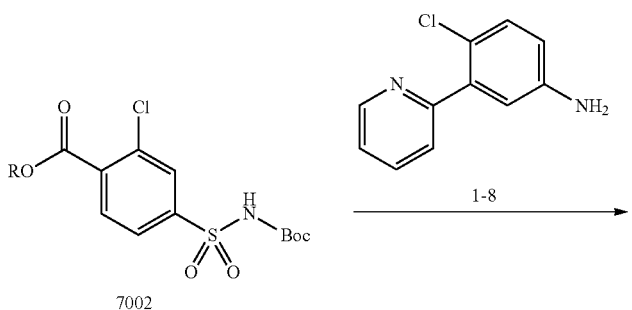
7002
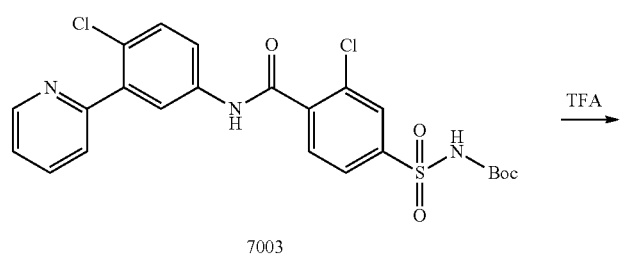
7003
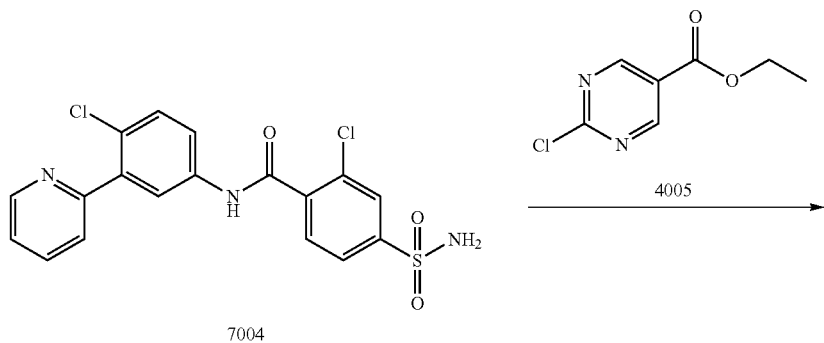
7004
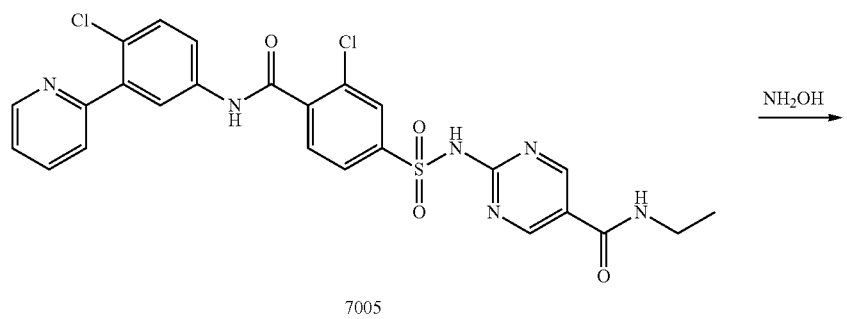
7005
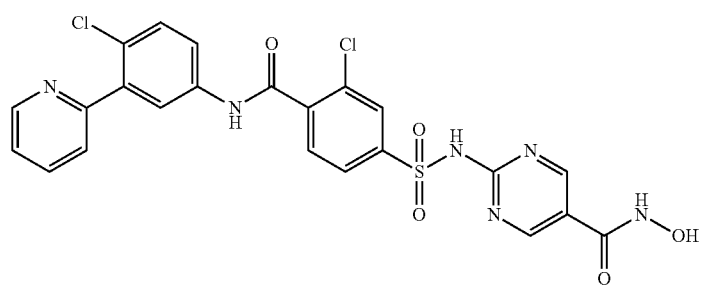

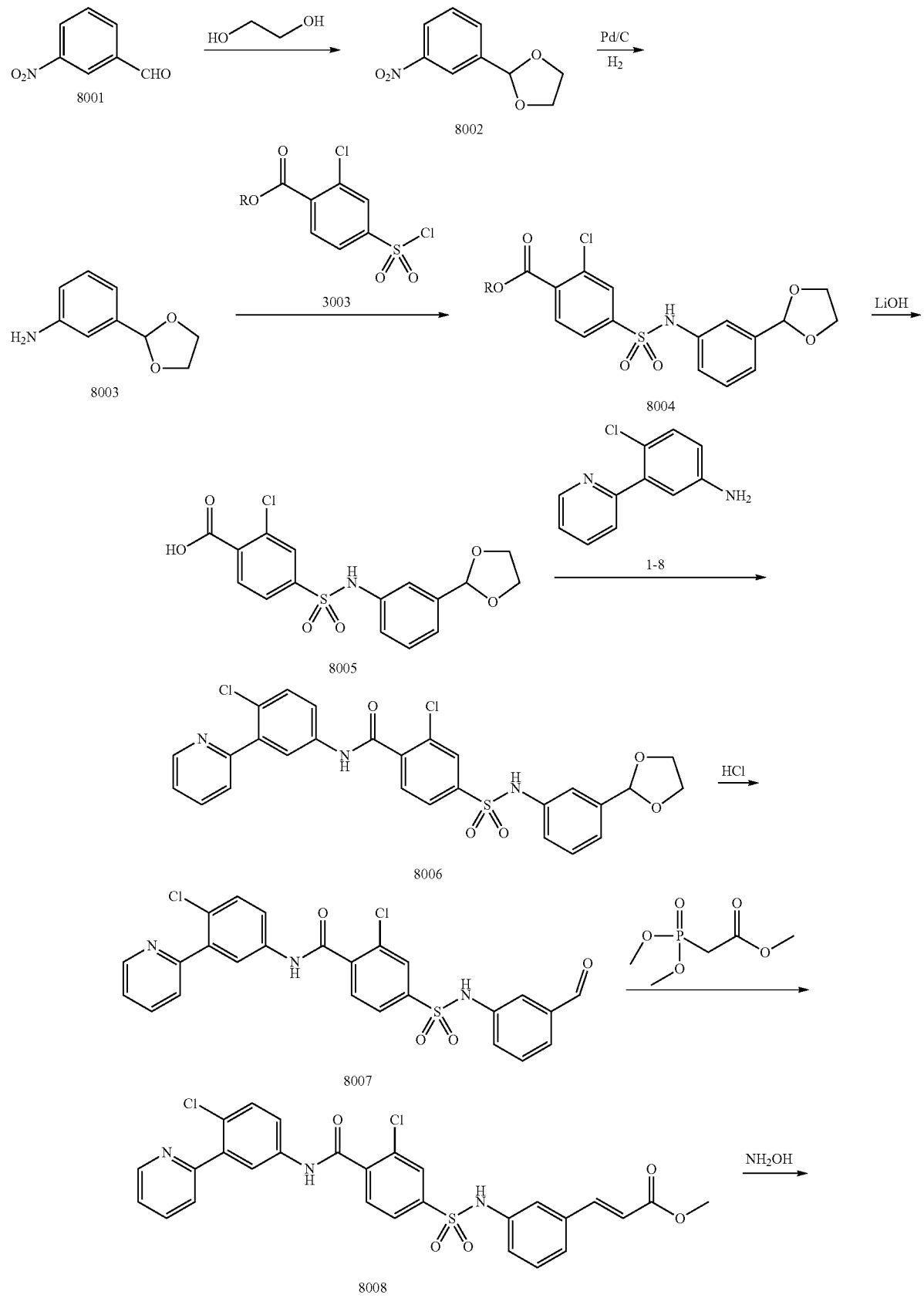

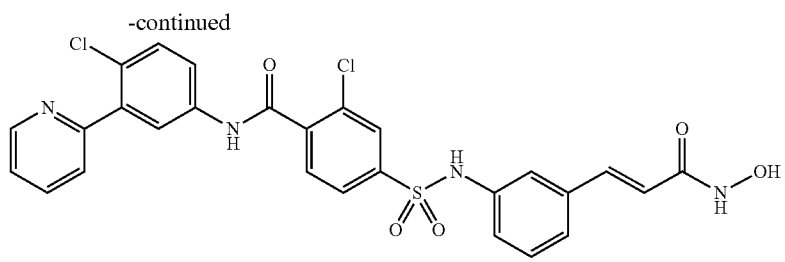
Scheme 10
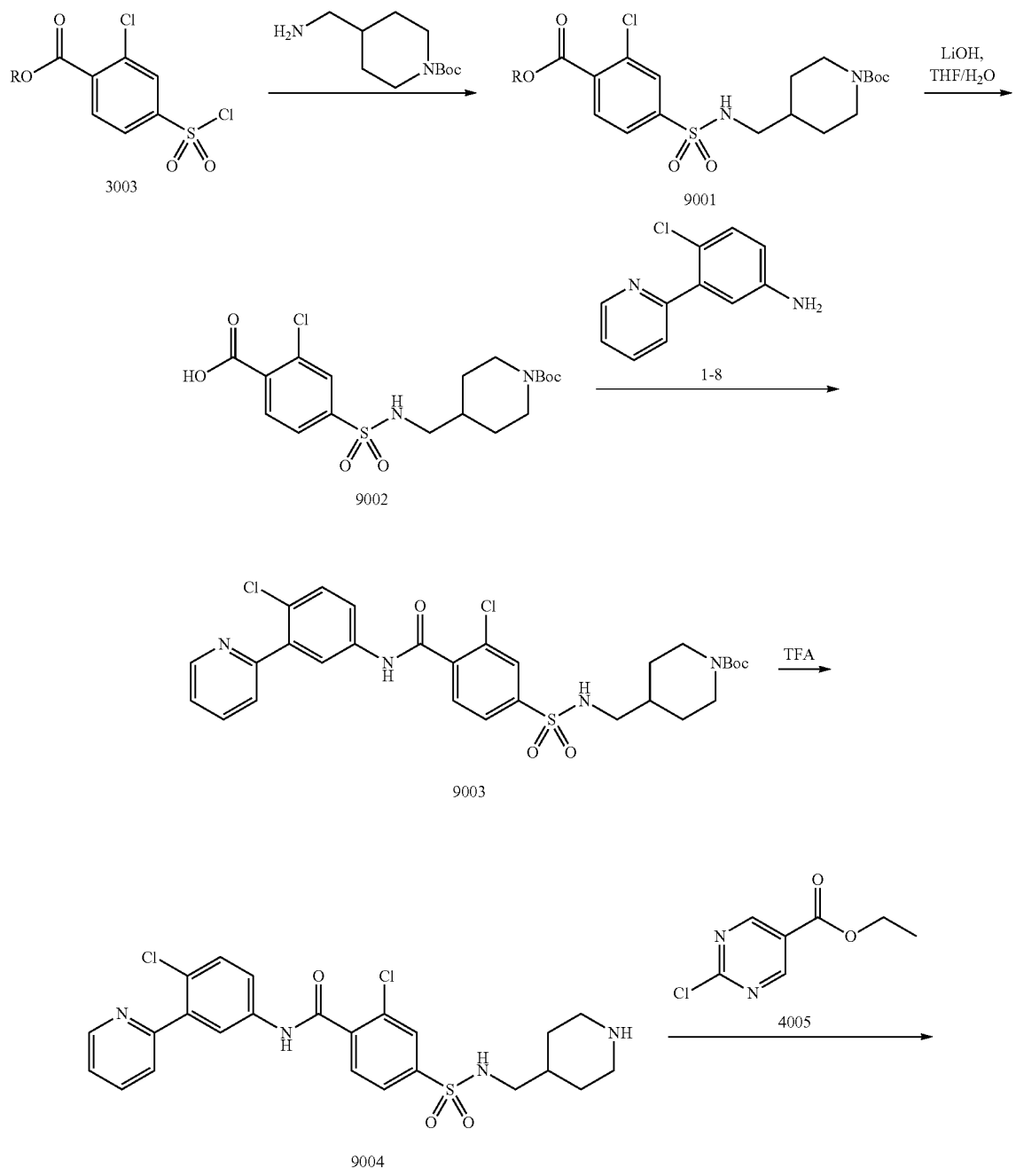

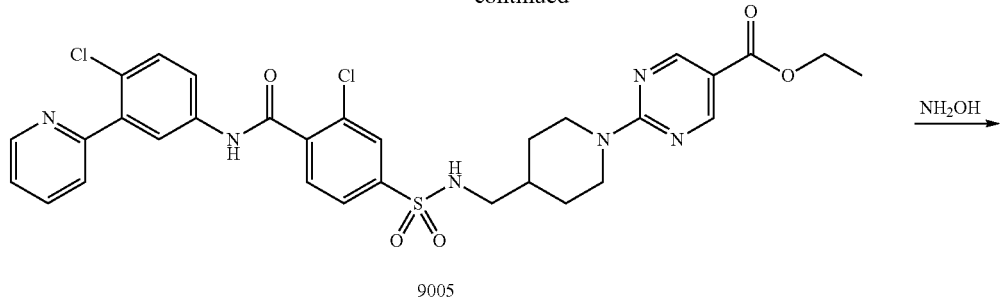
9005
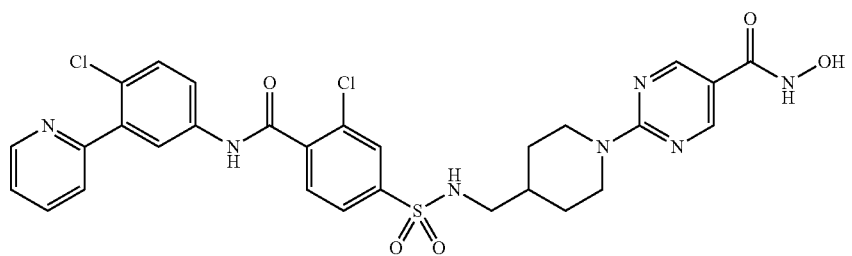 [SMILES: O=C(NO)c1cnc(N2CCC(CNS(=O)(=O)c3ccc(C(=O)Nc4ccc(Cl)c(-c5ccccn5)c4)c(Cl)c3)CC2)nc1]
NH₂OH →
Scheme 11
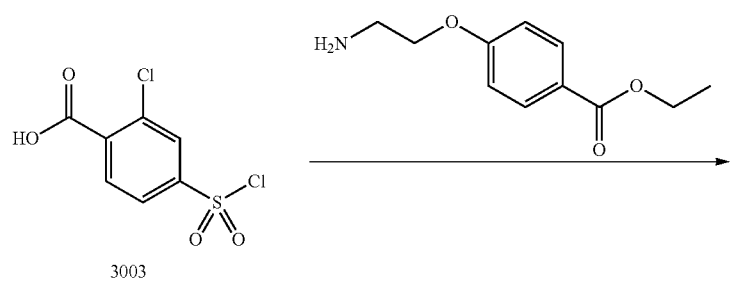
3003
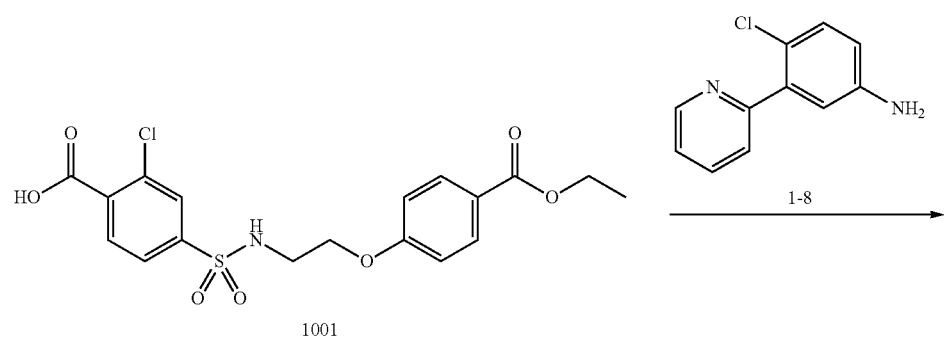
1001
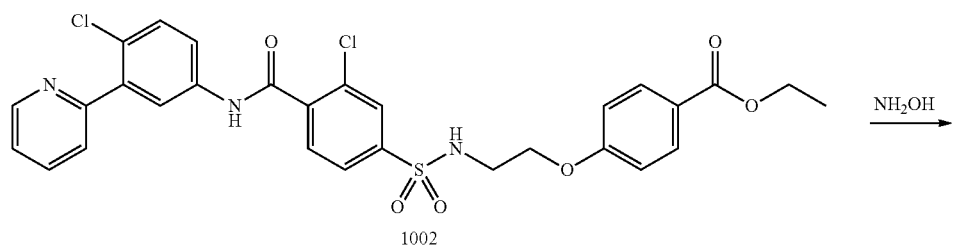
1002
NH₂OH →

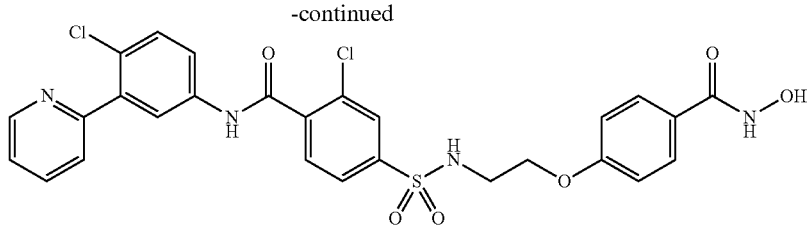
Scheme 12
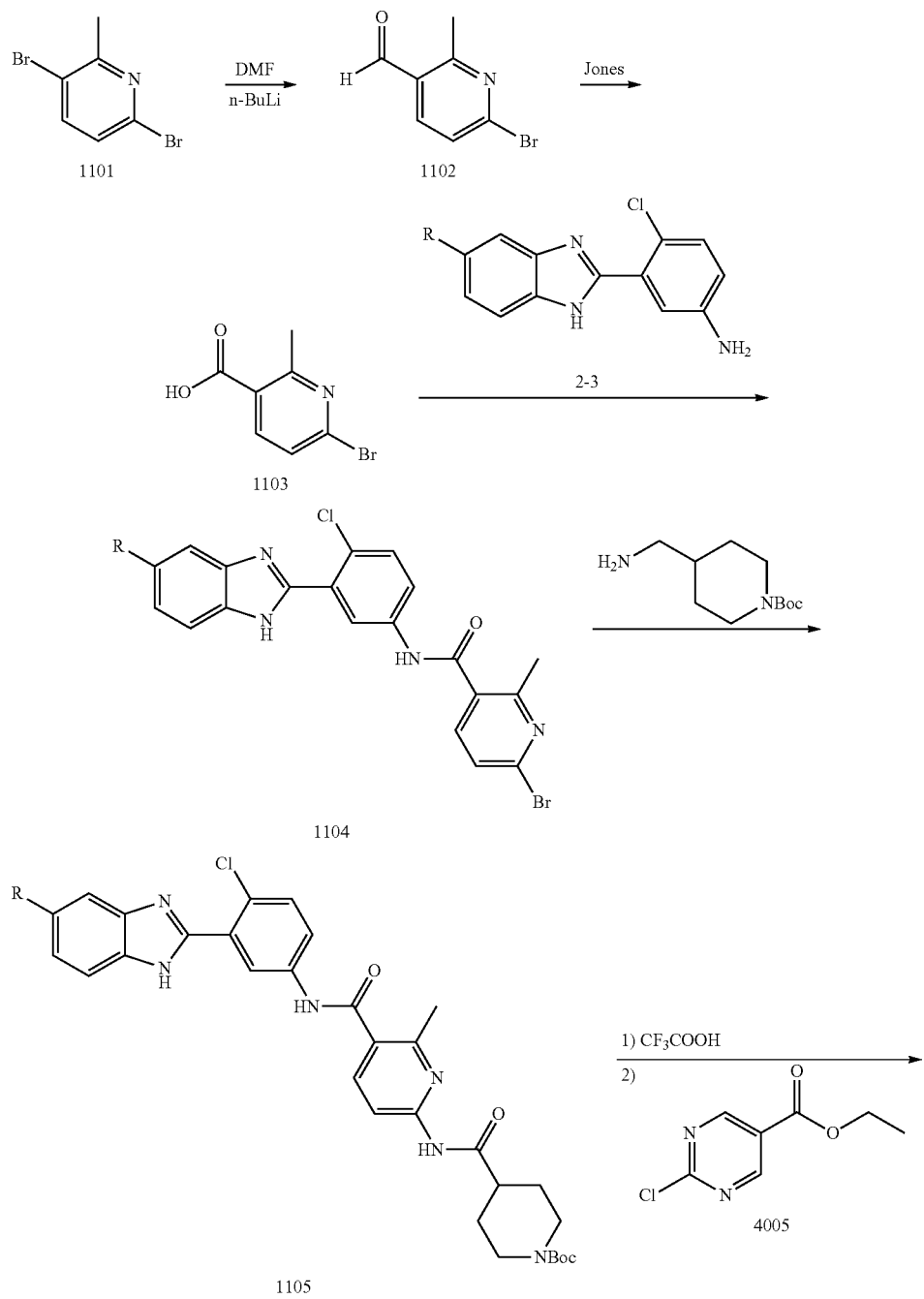

119
-continued
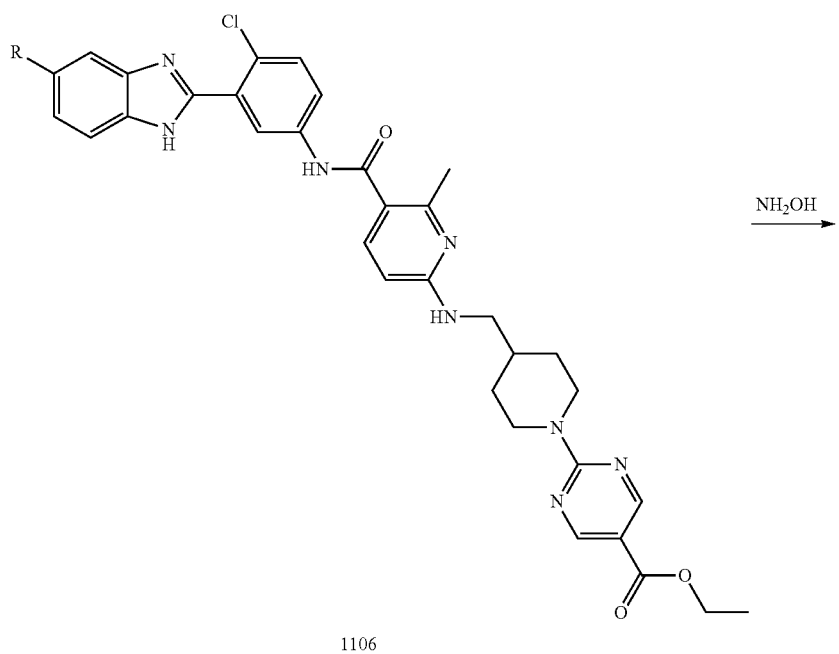
1106
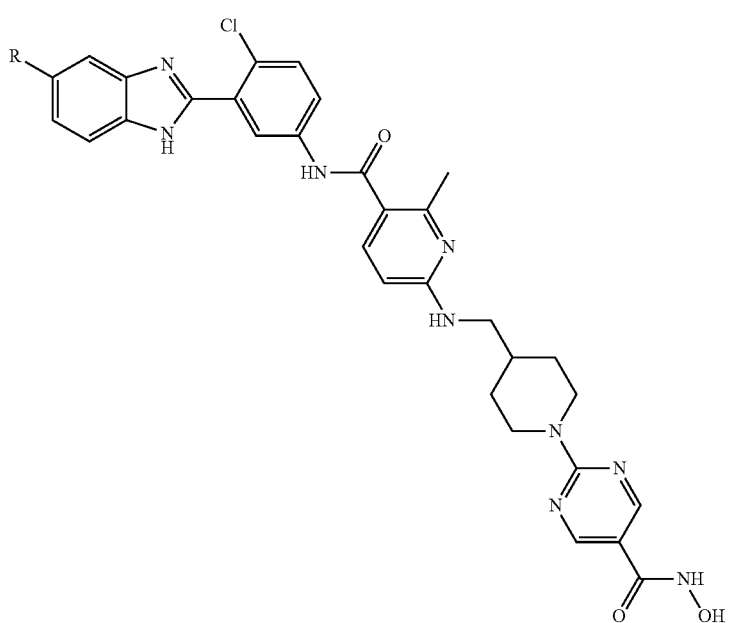
120
Scheme 13
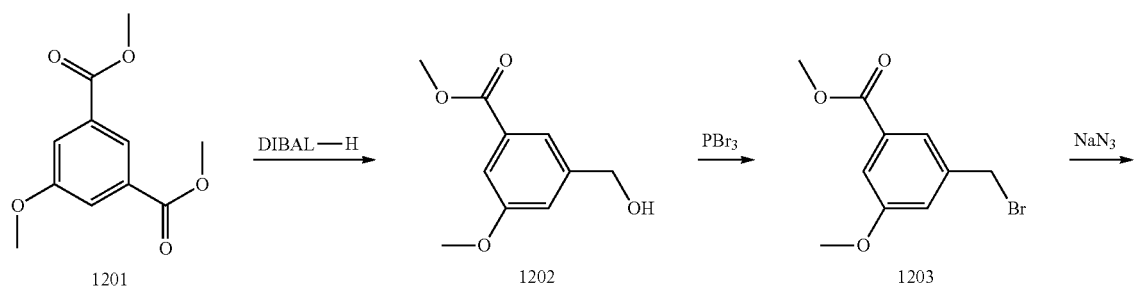

121
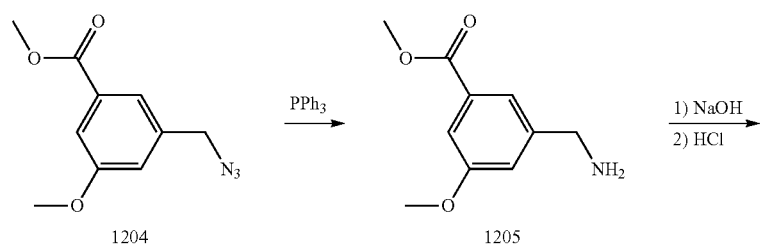
1204 1205
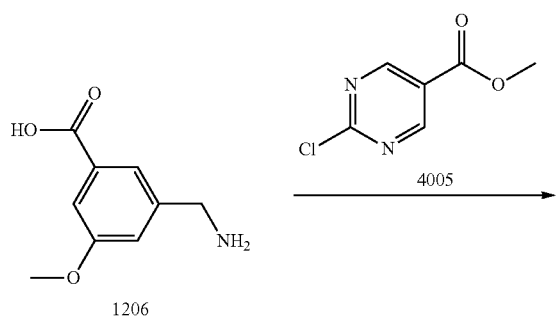
1206
122
-continued
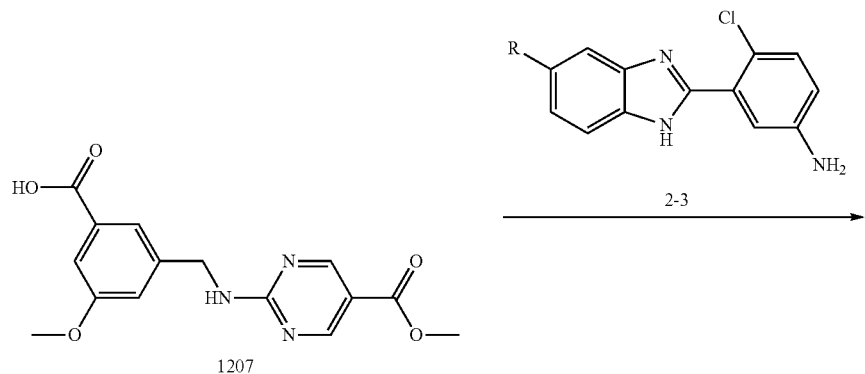
1207
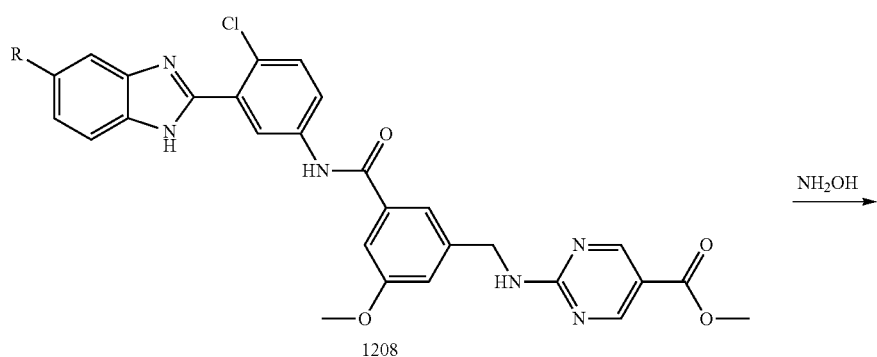
1208
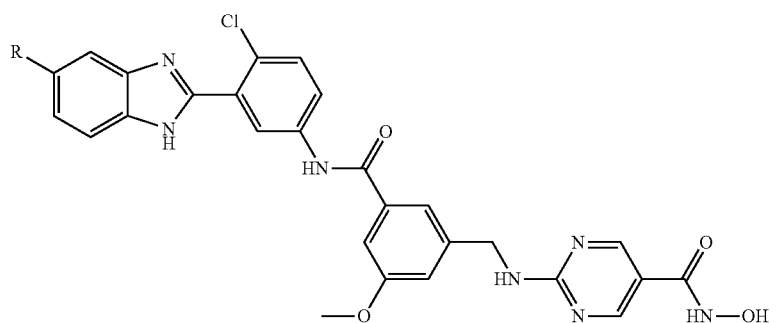

123 124
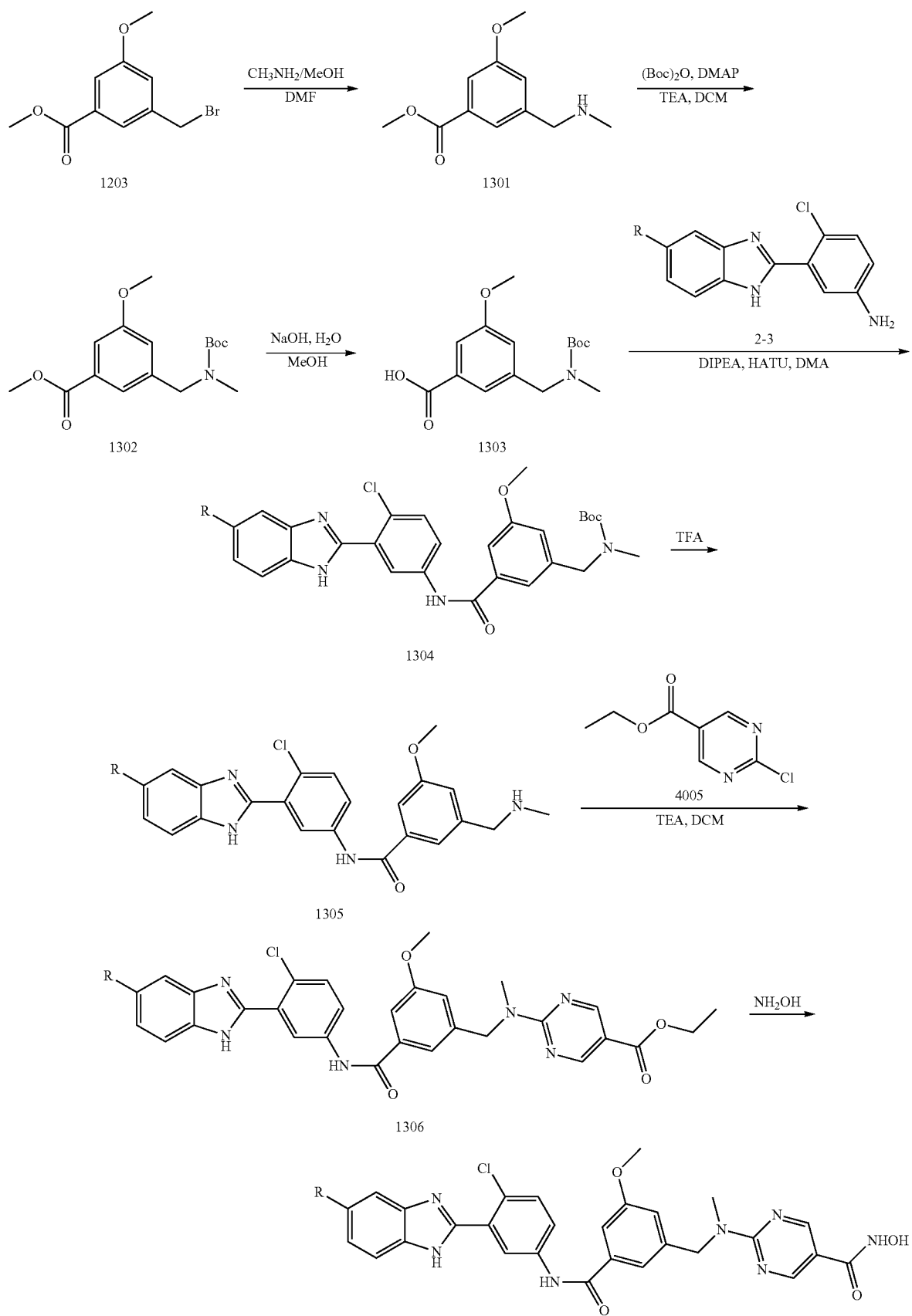

Synthesis of Intermediates

1) Preparation of 1-chloro-2-iodo-4-nitrobenzene (Compound 1-3)

2-Chloro-5-nitroaniline (40 g, 232.0 mmol) was added to a solution of concentrated sulfuric acid (32 mL) in water (320 mL) with mechanical stir. The solution was cooled to −5° C. and a solution of sodium nitrite (18.2 g, 0.26 mol) in water (69 mL) was added slowly. The mixture was stirred for 0.5 h in ice bath and then a solution of potassium iodide (69.3 g, 0.41 mol) in water (277 mL) was added dropwise while keeping the internal temperature below 5° C. The solution was stirred for 3 h at 0° C. followed by extraction with ethyl acetate. The combined organic layers were washed with saturated $Na_2S_2O_3$, dried over $Na_2SO_4$ and concentrated. The residue was recrystallized from $^iPrOH$/hexanes (300 mL/100 mL) to afford compound 1-3 as a light tan crystalline solid (38 g, 58% yield). $^1H$ NMR (400 MHz, $CDCl_3$): δ 7.61 (d, J=8.8 Hz, 1H), 8.16 (dd, J=8.8 Hz, 2.4 Hz, 1H), 8.70 (d, J=2.8 Hz, 1H).

2) Preparation of 4-chloro-3-iodoaniline (Compound 1-4)

A mixture of compound 1-3 (37 g, 0.13 mol), iron powder (29.3 g, 0.52 mol), and $NH_4Cl$ (7 g, 0.13 mol) in $EtOH/H_2O$ (200 mL/100 mL) was stirred at 75° C. for 3 h. The reaction mixture was filtered and concentrated to remove most of EtOH. The remaining mixture was extracted with ethyl acetate, washed with water and brine, dried over $Na_2SO_4$. The titled compound 1-4 was obtained as a yellow solid (32 g, 97% yield) after concentration. LCMS: m/z 254.0 $[M+1]^+$. $^1H$ NMR (400 MHz, $CDCl_3$): δ 3.65 (br, 2H), 6.58 (dd, J=8.8 Hz, 2.4 Hz, 1H), 7.15-7.17 (m, 2H).

3) Preparation of 4-chloro-3-(4,4,5,5,-tetramethyl-1,3,2-dioxaborolan-2-yl)aniline (Compound 1-5)

A mixture of compound 1-4 (10 g, 39.5 mmol), 4,4,4',4',5,5,5',5'-octamethyl-2,2'-bi (1,3,2-dioxaborolane) (20.0 g, 79.0 mmol), KOAc (11.6 g, 118.5 mmol), and $PdCl_2(dppf)$ (960 mg, 1 mmol) in 1,4-dioxane (60 mL) was stirred at 105° C. for 8 h under $N_2$. The reaction mixture was concentrated in vacuo, and the residue was purified by column chromatography (hexanes/dichloromethane: 3/1 to 1/1) to afford compound 1-5 as a light yellow solid (6.0 g, 60% yield). LCMS: m/z 295.1 $[M+42]^+$. $^1H$ NMR (400 MHz, $CDCl_3$): δ 1.36 (s, 12H), 3.61 (br, 2H), 6.65 (dd, J=8.8 Hz, 2.8 Hz, 1H), 7.00 (d, J=2.8 Hz, 1H), 7.11 (d, J=8.8 Hz, 1H).

4) Preparation of 4-chloro-3-(pyridine-2-yl)aniline (Compound 1-8)

A mixture of compound 1-5 (1.50 g, 5.9 mmol), 2-bromopyridine (1.87 g, 11.8 mmol), sodium bicarbonate (1.49 g, 17.8 mmol), $PdCl_2(Ph_3P)_2$ (100 mg, 0.09 mmol) in 1,4-dioxane/water (20 mL/10 mL) was heated at 110° C. overnight. After cooling to room temperature, the mixture was quenched with water and extracted with ethyl acetate. The combined organic layers were washed with water and brine, dried over anhydrous sodium sulfate and evaporated in vacuo. The crude product was purified by column chromatography (hexanes/ethyl acetate: 3/1) to afford compound 1-8 as a yellow solid (1.38 g, ~100%). LCMS: m/z 205.1 $[M+1]^+$. $^1H$ NMR (400 MHz, DMSO-$d_6$): δ 5.32 (s, 2H), 6.61 (dd, J=8.4 Hz, 2.8 Hz, 1H), 6.77 (d, J=2.8 Hz, 1H), 7.14 (d, J=8.4 Hz, 1H), 7.35-7.39 (m, 1H), 7.57 (d, J=8.0 Hz, 1H), 7.83-7.87 (m, 1H), 8.63-8.65 (m, 1H).

5) Preparation of 2-chloro-N-(4-chloro-3-(4,4,5,5-tetramethyl-1,3,2-dioxaborolan-2-yl)phenyl)-4-(methylsufonyl)benzamide (Compound 1-9)

A mixture of compound 1-5 (1 g, 3.9 mmol), 2-chloro-4-(methylsulfonyl)benzoic acid (1.1 g, 4.7 mmol) and N,N-Diisopropylethylamine (1 g, 7.8 mmol) and O-(Benzotriazol-1-yl)-N,N,N',N'-tetramethyluroniumtetrafluoroborate (2.6 g, 7.8 mmol) in dichloromethane (20 mL) was stirred at room temperature overnight. The reaction mixture was quenched with water, filtered. The solid was collected and dried in vacuo to afford compound 1-9 as a white solid (1.2 g, 65% yield). LCMS: m/z 470.1 $[M+1]^+$. $^1H$ NMR: (400 MHz, DMSO-$d_6$): δ 1.32 (s, 12H), 3.35 (s, 3H), 7.43 (d, J=8.8 Hz, 1H), 7.81 (dd, J=8.8 Hz, 2.8 Hz, 1H), 7.89 (d, J=8.0 Hz, 1H), 7.98-8.01 (m, 2H), 8.12 (d, J=1.6 Hz, 1H), 10.82 (s, 1H).

6) Preparation of 2-chloro-5-nitro-N-(2-nitrophenyl)benzamide (Compound 2-2)

To a solution of 2-nitroaniline (5.0 g, 0.036 mol) in $CH_3CN$ (50 mL) was added a solution of 2-chloro-5-nitrobenzoyl chloride (8.0 g, 0.037 mol) in $CH_3CN$ (10 mL) dropwise while keeping the internal temperature below 25° C. under $N_2$. When addition was complete the reaction mixture was heated at 75° C. for 1 h. The mixture was cooled to 0° C. and filtered. The solid was rinsed with cold $CH_3CN$ to afford 2-2 as a light yellow solid (5.3 g, 50%).

7) Preparation of 3-(1H-benzo[d]imidazol-2-yl)-4-chloroaniline (Compound 2-3)

Compound 2-2 (5.3 g, 0.017 mol) was taken into EtOH (100 mL) and heated to 40° C. When the internal temperature reached 40° C., $1^{st}$ aliquot $SnCl_2$/HCl (3 vol respectively, divided into 3 portions) was added. The reaction mixture was heated to 60° C. and the $2^{nd}$ aliquot of $SnCl_2$/HCl was added. The reaction mixture was heated to 80° C. and the $3^{rd}$ aliquot $SnCl_2$/HCl was added and continued to reflux 2 h. The reaction mixture was cooled to 0° C. and NaOH (1N aqueous solution) was added below 10° C. to adjust pH to 12-13. The mixture was diluted with EA and water. The organic layer was washed with brine and concentrated. The crude product was purified by column chromatography eluted with dichloromethane/methanol (60:1) to afford compound 2-3 as a yellow solid (2.7 g, 68% yield). LCMS: m/z 244.1$[M+1]^+$. $^1H$ NMR (400 MHz, DMSO-d6): δ 5.48 (s, 2H), 6.71 (d, J=8.8 Hz, 1H), 7.13 (s, 1H), 7.21-7.24 (m, 3H), 7.57 (br, 1H), 7.64 (br, 1H), 12.52 (s, 1H).

Example 1: Preparation of (E)-2-chloro-N-(4-chloro-3-(5-(3-(hydroxyamino)-3-oxoprop-1-enyl)pyridin-2-yl)phenyl)-4-(methylsulfonyl)benzamide (Compound 1)

Step 1a. (E)-Methyl 3-(6-bromopyridin-3-yl)acrylate (Compound 1001-1)

A mixture of 6-bromonicotinaldehyde (500 mg, 2.7 mmol) and methyl (triphenylphosphoranylidene) (1 g, 3.2 mmol) in dichloromethane (10 mL) was stirred at room temperature for 1 h. The mixture was concentrated in vacuo and filtered. The solid was washed with hexanes to afford crude compound 1001-1 as a white solid (1.5 g).

Step 1b. (E)-Methyl-3-(6-(2-chloro-5-(2-chloro-4-(methylsulfonyl)benzamido)phenyl) pyridin-3-yl) acrylate (1002-1)

A mixture of 1001 (121 mg, 0.5 mmol), 1-9 (200 mg, 0.4 mmol), Pd(PPh$_3$)$_2$Cl$_2$ (30 mg) in 1,4-dioxane (6 mL) and aq NaHCO$_3$ (2 mL) was stirred at 110° C. for 3 h under N$_2$. After cooling to room temperature, the reaction mixture was quenched with water, extracted with ethyl acetate. The combined organic layers were washed with water and brine, dried over anhydrous sodium sulfate, evaporated in vacuo. The crude product was purified by column chromatography (methanol/dichloromethane: 1/20) to afford compound 1002 as a pale yellow solid (160 mg, 74% yield). $^1$H NMR (400 MHz, CDCl$_3$): δ 3.09 (s, 3H), 3.85 (s, 3H), 6.57 (d, J=16.0 Hz, 1H), 7.44-7.48 (m, 1H), 7.52-7.55 (m, 1H), 7.62-7.67 (m, 1H), 7.73 (d, J=16.0 Hz, 1H), 7.80 (d, J=8.0 Hz, 1H), 7.81-7.86 (m, 2H), 7.89 (s, 1H), 7.89-7.95 (m, 2H), 8.03 (d, J=1.2 Hz, 1H), 8.14 (s, 1H), 8.80 (d, J=2.0 Hz, 1H).

Step 1c. (E)-2-Chloro-N-(4-chloro-3-(5-(3-(hydroxyamino)-3-oxoprop-1-enyl)pyridin-2-yl)phenyl)-4-(methylsulfonyl)benzamide (Compound 1)

A mixture of NH$_2$OH.HCl (80 g, 1.15 mol) in MeOH (400 mL) was heated at 60-65° C. while stirring to form a clear solution. After additional 1 h at reflux, it was cooled to 0-10° C. To the reaction mixture a pre-formed solution of KOH (96 g, purity >85%) in MeOH (237 mL) (prepared by adding KOH in portion to methanol at 0-10° C.) was added dropwise while maintaining internal temperature <10° C. The resulting mixture was continued to stir at 0-10° C. for 30 min. The suspension was poured into pressure equalizing addition funnel (1 L) pre-packed with anhydrous Na$_2$SO$_4$ (700 g) and let it sit for 0.5 h. The clear filtrate was collected as NH$_2$OH methanolic solution.

A mixture of 1002 (150 mg, 0.3 mmol) in NH$_2$OH methanolic solution (5 mL, 1.79M) was stirred at room temperature for 3~4 h. The reaction mixture was adjusted pH to 6-7 with 1.2 M HCl and concentrated. The residue was triturated with water and filtered, dried in vacuo to afford compound 1 as an off white solid (90 mg, 60% yield). M.p: 185~187° C. LCMS: m/z 506.1[M+1]$^+$. $^1$H NMR (400 MHz, DMSO-d$_6$): δ 3.35 (s, 3H), 6.65 (d, J=16.0 Hz, 1H), 7.55-7.61 (m, 2H), 7.74-7.78 (m, 2H), 7.91 (d, J=8.0 Hz, 1H), 8.01 (d, J=8.4 Hz, 1H), 8.06 (d, J=2.0 Hz, 1H), 8.11-8.13 (m, 2H), 8.90 (s, 1H), 10.90 (br, 1H), 10.96 (s, 1H).

Example 2: Preparation of 6-(2-Chloro-5-(2-chloro-4-(methylsulfonyl) benzamido)phenyl)-N-hydroxynicotinamide (Compound 5)

Step 2a. Methyl 6-bromonicotinate (Compound 1001-5)

To a solution of 6-bromonicotinic acid (500 mg, 2.5 mmol) in dichloromethane (10 mL) and THF (5 mL) was added oxalyl chloride (1.4 mL, 0.016 mol) followed by addition of one drop of DMF. The mixture was stirred at room temperature for 1 h. After removal of solvent, the residue was dissolved in anhydrous methanol (5 mL) and continued to stir for 10 min. The reaction mixture was quenched with ice water and filtered to afford 1001-5 as a pale yellow solid (212 mg, 40%). LCMS: m/z 213.1 [M+1]$^+$. $^1$H NMR (400 MHz, CDCl$_3$): δ 3.96 (s, 3H), 7.42 (d, J=8.4 Hz, 1H), 8.25 (dd, J=8.0 Hz, 2.0 Hz, 1H), 9.00 (d, J=2.0 Hz, 1H).

Step 2b. Methyl 6-(2-chloro-5-(2-chloro-4-(methylsulfonyl)benzamido)phenyl) nicotinate (Compound 1002-5)

A mixture of compound 1001-5 (200 mg, 0.9 mmol), 1-9 (367 mg, 0.8 mmol) and Pd(PPh$_3$)$_4$ (21 mg, 0.018 mmol) in saturated NaHCO$_3$ (2 mL) and 1,4-dioxane (6 mL) was stirred at 100° C. for 3 h. To the reaction mixture was added NaOH (37 mg, 0.9 mmol) and stirred for 0.5 h. The reaction mixture was adjusted pH to 6 with 1.2M HCl and extracted with ethyl acetate. The organic layer was washed with water and brine, dried over anhydrous sodium sulfate. The methyl ester was hydrolyzed during this reaction condition, and the obtained crude acid product (365 mg) (LCMS: m/z 465.1 [M+1]$^+$) was used for the next step without further purification. The mixture of the crude acid product (365 mg, 0.8 mmol) in MeOH (15 mL) and H$_2$SO$_4$ (0.25 mL) was stirred at 85° C. for 1 h. The reaction mixture was concentrated. The residue was partitioned between water and ethyl acetate. The organic layers were washed with water and brine, dried over anhydrous sodium sulfate and concentrated. The residue was purified by column chromatography (dichloromethane/methanol: 20/1) to afford 1002-5 as a white solid (176 mg, 39% yield via two steps). LCMS: m/z 479.1 [M+1]$^+$. $^1$H NMR (400 MHz, CDCl$_3$): δ 3.07 (s, 3H), 3.99 (s, 3H), 7.52 (d, J=8.8 Hz, 1H), 7.81-7.86 (m, 4H), 7.88 (dd, J=8.8 Hz, 2.8 Hz, 1H), 7.97 (d, J=1.2 Hz, 1H), 8.37 (dd, J=8.4 Hz, 2.4 Hz, 1H), 8.62 (s, 1H), 9.17 (d, J=1.2 Hz, 1H).

Step 2c. 6-(2-Chloro-5-(2-chloro-4-(methylsulfonyl) benzamido)phenyl)-N-hydroxynicotinamide (Compound 5)

A mixture of 1002-5 (176 mg, 0.4 mmol) in NH$_2$OH methanolic solution (5 mL, 1.79 M) was stirred at room temperature for 1 h. The reaction mixture was adjusted pH to 6~7 with 1.2 M HCl. The reaction mixture was filtered, washed with water, dried in vacuo to afford compound 5 as an off-white solid (120 mg 70% yield). M.p.: 190~193° C. LCMS: m/z 480.2 [M+1]$^+$. HNMR: (400 MHz, DMSO-d$_6$): δ 3.35 (s, 3H), δ 7.61 (d, J=8.4 Hz, 1H), 7.76 (dd, J=8.8 Hz, 2.4 Hz, 1H), 7.82 (d, J=8.0 Hz, 1H), 7.91 (d, J=8.0 Hz, 1H), 8.01 (dd, J=8.0 Hz, 1.6 Hz, 1H), 8.05 (d, J=2.4 Hz, 1H), 8.13 (d, J=1.6 Hz, 1H), 8.22 (dd, J=8.0 Hz, 2.0 Hz, 1H), 9.02 (d, J=1.6 Hz, 1H), 9.28 (s, 1H), 10.96 (s, 1H), 11.48 (s, 1H).

Example 3: Preparation of 2-[2-Chloro-5-(2-chloro-4-methanesulfonyl-benzoylamino)-phenyl]-pyrimidine-5-carboxylic acid hydroxyamide (Compound 7)

Step 3a. 2-Chloro-pyrimidine-5-carboxylic acid methyl ester (Compound 1001-7)

A mixture of NaH (27 g, 60% in mineral oil, 0.675 mol) in anhydrous 1,2-dimethoxyethane (300 mL) was heated to 40-50° C. Methyl 3,3-dimethoxy propionate (100 g, 0.675 mol) was added dropwise. The resulting mixture was stirred for 0.5 h and anhydrous methyl formate (81 g, 1.35 mol) was added dropwise at 40-50° C. The resulting mixture was stirred at 40-50° C. (inner temperature) for 2 h before it was cooled to 0° C. The reaction mixture was allowed to warm to 25° C. slowly and stirred overnight. Et$_2$O (150 mL) was added and stirred for 30 min. The resulting suspension was filtered. The solid was washed with Et$_2$O (100 mL), collected and dried to afford sodium (Z)-2-(dimethoxymethyl)-3-methoxy-3-oxoprop-1-en-1-olate as an off-white solid (82 g, 61%). LCMS: m/z 130.8 [M+1]$^+$. $^1$HNMR (400 MHz, CD$_3$OD): δ 3.36 (s, 6H), 3.60 (s, 3H), 5.34 (s, 1H), 8.92 (s, 1H).

To a mixture of guanidine hydrochloride (42.2 g, 0.44 mol) in DMF (300 mL) was added above off-white solid (80 g, 0.40 mol). The resulting mixture was heated at 100° C. for 1 h. The reaction mixture was filtered before cooled. The filter cake was washed with 50 mL of DMF and the combined filtrate was concentrated to leave a residue which was suspended in cold EtOH and washed with cold EtOH (50 mL) to afford the intermediate 2-amino-pyrimidine-5-carboxylic acid methyl ester as a yellow solid (38 g, 61.5%). LCMS: m/z 154.2 [M+1]$^+$, 195.1[M+42]$^+$. $^1$HNMR (400 MHz, CD$_3$OD): δ 3.88 (s, 3H), 8.77 (s, 2H).

The above intermediate (7 g, 0.046 mol) was added to a mixture of concentrated hydrochloric acid (15.2 mL) and CH$_2$Cl$_2$ (60 mL). After cooling, ZnCl$_2$ (18.6 g, 0.138 mol) was added at 15-20° C. The mixture was stirred at 15-20° C. for 0.5 h and cooled to 5-10° C. NaNO$_2$ (9.5 g, 0.138 mol) was added portion wise while keeping the internal temperature 5-10° C. The reaction was continued for ~2 h. The reaction mixture was poured into ice-water (50 mL). The organic layer was separated and the aqueous phase was extracted with CH$_2$Cl$_2$ (30 mL×2). The combined organic extracts were concentrated to afford crude product (4.2 g). The crude compound was suspended in hexane (20 mL), heated at 60° C. for 30 minutes and filtered. The filtrate was concentrated to afford the titled compound 1001-7 (3.5 g, 44.4%) as an off-white solid. LCMS: m/z 214.1[M+42]$^+$. $^1$HNMR (400 MHz, CDCl$_3$): δ 4.00 (s, 3H), 9.15 (s, 2H).

Step 3b. 2-[2-Chloro-5-(2-chloro-4-methanesulfonyl-benzoylamino)-phenyl]-pyrimidine-5-carboxylic acid methyl ester (Compound 1002-7)

A mixture of 1001-7 (200 mg, 1.1 mmol), 1-9 (756 mg, 1.6 mmol) and Pd(PPh$_3$)$_4$ (60 mg, 0.05 mmol) in saturated NaHCO$_3$ (2 mL) and DMSO (6 mL) was stirred at 100° C. for 3 h. After cooling to room temperature, NaOH (43 mg, 1.1 mmol) was added to reaction solution and stirred for 0.5 h. The reaction mixture was extracted with ethyl acetate. The aqueous layer was adjusted pH to 6 with 1.2 M HCl and extracted with ethyl acetate. The combined organic layers were washed with water and brine, dried over Na$_2$SO$_4$, concentrated to afford crude acid (300 mg) without further purification.

The mixture of the crude acid (300 mg) in MeOH (15 mL) and H$_2$SO$_4$ (0.25 mL) was stirred at 85° C. for 1 h. After removal of solvent, the residue was partitioned between water and ethyl acetate. The combined organic layers were washed with water and brine, dried over Na$_2$SO$_4$. The crude product was purified by column chromatography (hexanes/ethyl acetate: 1/1) to afford compound 1002-7 as a white solid (160 mg, 78% yield via two steps). LCMS: m/z 480.2[M+1]$^+$. $^1$H NMR: (400 MHz, CDCl$_3$): δ 3.36 (s, 3H), 3.96 (s, 3H), 7.65 (d, J=8.8 Hz, 1H), 7.81 (dd, J=8.8 Hz, J=2.4 Hz, 1H), 7.93 (d, J=8.0 Hz, 1H), 8.02 (dd, J=8.0 Hz, 1.6 Hz, 1H), 8.14 (d, J=1.2 Hz, 1H), 8.30 (d, J=2.4 Hz, 1H), 9.40 (s, 2H), 11.02 (s, 1H).

Step 3c. 2-[2-Chloro-5-(2-chloro-4-methanesulfonyl-benzoylamino)-phenyl]-pyrimidine-5-carboxylic acid hydroxyamide (Compound 7)

A mixture of compound 1002-7 (160 mg, 0.3 mmol) in NH$_2$OH methanolic solution (5 mL, 1.79 M) was stirred at room temperature for 1 h. The reaction mixture was adjusted pH to 6~7 with 1.2 M HCl and concentrated. The residue was triturated with water and filtered. The crude product was purified by prep-HPLC to afford compound 7 as an off-white solid (28 mg, 18% yield). M.p.: 170~172° C. LCMS: m/z 481.1 [M+1]$^+$. $^1$H NMR: (400 MHz, DMSO-d$_6$): δ 3.35 (s, 3H), 7.63 (d, J=8.8 Hz, 1H), 7.79 (dd, J=8.8 Hz, 2.4 Hz, 1H), 7.93 (d, J=8.0 Hz, 1H), 8.01 (dd, J=8.0 Hz, 1.6 Hz, 1H), 8.14 (d, J=1.6 Hz, 1H), 8.26 (d, J=2.4 Hz, 1H), 9.23 (s, 2H), 11.01 (s, 1H).

Example 4: 2-Chloro-N-{4-chloro-3-[5-(6-hydroxycarbamoyl-hexyloxy)-pyridin-2-yl]-phenyl}-4-methanesulfonyl-benzamide (Compound 23)

Step 4a. 6-Bromo-pyridin-3-ol (Compound 2002)

3-Amino-6-bromopyridine (1 g, 5.8 mmol) was dissolved in HBF$_4$ (3.6 mL, 40% aq) and water (3 mL). To the cooled brownish solution under an ice-bath was added dropwise NaNO$_2$ (441 mg, 6.4 mmol) solution in water (3 mL). The resulting mixture was stirred for 1 h at this temperature. After addition of water (3 mL), the mixture was stirred at 100° C. for 3.5 h. The reaction mixture was neutralized by aqueous NaHCO$_3$ (5%) and extracted with ethyl acetate. The combined organic layers were washed with water and brine, dried over anhydrous Na$_2$SO$_4$ and evaporated in vacuo. The residue was purified by column chromatography (hexanes/ethyl acetate: 9/1) to afford compound 2002 as a white solid (270 mg, 27% yield). LCMS: m/z 174.0 [M+1]$^+$. $^1$H NMR (400 MHz, CDCl$_3$): δ 6.65 (br, 1H), 7.13 (dd, J=8.4 Hz, 3.2 Hz, 1H), 7.36 (d, J=8.4 Hz, 1H), 8.03 (d, J=3.2 Hz, 1H).

Step 4b. 7-(Pyridin-3-yloxy)-heptanoic acid ethyl ester (Compound 2003-23)

A mixture of 2002 (270 mg, 1.5 mmol), ethyl 7-bromoheptanoate (736 mg, 3.1 mmol) and K$_2$CO$_3$ (430 mg, 3.1 mmol) in DMF (10 mL) was stirred at 75° C. for 1 h. The solution was partitioned between water and ethyl acetate. The combined organic layers were washed with water and brine, dried over anhydrous Na$_2$SO$_4$ and evaporated in vacuo. The residue was purified by column chromatography (hexanes/ethyl acetate: 20/1) to afford compound 2003-23 as a white solid (440 mg, 86% yield). LCMS: m/z 330.1 [M+1]$^+$. $^1$H NMR: (400 MHz, CDCl$_3$): δ 1.25 (t, J=7.2 Hz, 3H), 1.36-1.52 (m, 4H), 1.62-1.68 (m, 2H), 1.76-1.83 (m, 2H), 2.31 (t, J=7.2 Hz, 2H), 3.97 (t, J=6.4 Hz, 2H), 4.13 (q, J=7.2 Hz, 2H), 7.08 (dd, J=8.8 Hz, 3.2 Hz, 1H), 7.35 (d, J=8.8 Hz, 1H), 8.04 (d, J=2.8 Hz, 1H).

Step 4c. 7-{6-[2-Chloro-5-(2-chloro-4-methanesulfonyl-benzoylamino)-phenyl]-pyridin-3-yloxy}-heptanoic acid ethyl ester (Compound 2004-23)

A mixture of 2003-23 (168 mg, 0.51 mmol), 1-9 (200 mg, 0.43 mmol) and Pd(PPh$_3$)$_4$ (24.6 mg, 0.03 mmol) in saturated NaHCO$_3$ (2 mL) and 1,4-dioxane (6 mL) was stirred at 100° C. for 3 h. The solution was partitioned between water and ethyl acetate. The combined organic layers were washed with water and brine, dried over anhydrous Na$_2$SO$_4$ and evaporated in vacuo. The residue was purified by column chromatography (dichloromethane/methanol: 100/1) to afford 2004-23 as a white solid (130 mg, 43% yield). LCMS: m/z 593.2 [M+1]$^+$. $^1$H NMR (400 MHz, CDCl$_3$): δ 1.26 (t, J=7.2 Hz, 3H), 1.37-1.54 (m, 4H), 1.63-1.71 (m, 2H), 1.78-1.85 (m, 2H), 2.32 (t, J=7.2 Hz, 2H), 3.00 (s, 3H), 3.98 (t, J=6.4 Hz, 2H), 4.12 (q, J=7.2 Hz, 2H), 7.19 (dd, J=8.8 Hz, 2.8 Hz, 1H), 7.58 (d, J=1.2 Hz, 1H), 7.61 (d, J=1.2 Hz, 1H), 7.63 (d, J=1.6 Hz, 1H), 7.69 (dd, J=8.0 Hz, 1.6 Hz, 1H), 7.73 (d, J=2.4 Hz, 1H), 7.86 (d, J=1.6 Hz, 1H), 8.02 (dd, J=8.8 Hz, 2.8 Hz, 1H), 8.05 (d, J=2.8 Hz, 1H), 9.88 (s, 1H).

Step 4d. 2-Chloro-N-{4-chloro-3-[5-(6-hydroxycarbamoyl-hexyloxy)-pyridin-2-yl]-phenyl}-4-methanesulfonyl-benzamide (Compound 23)

A mixture of 2004-23 (130 mg, 0.22 mmol) in NH$_2$OH methanolic solution (5 mL, 1.79 M) was stirred at room temperature for 1 h. The reaction mixture was adjusted pH to 6-7 with 1.2 M HCl. The resulting mixture was filtered. The collected solid was purified by prep-HPLC to afford compound 23 as a white solid (27 mg, 21% yield). M.p.: 140-145° C. LCMS: m/z 580.2 [M+1]$^+$. $^1$H NMR (400 MHz, DMSO-d$_6$): δ 1.29-1.35 (m, 2H), 1.40-1.47 (m, 2H), 1.49-1.56 (m, 2H), 1.72-1.78 (m, 2H), 1.96 (t, J=7.2 Hz, 2H), 3.35 (s, 3H), 4.10 (t, J=6.4 Hz, 2H), 7.50 (dd, J=8.8 Hz, 2.8 Hz, 1H), 7.55 (d, J=8.8 Hz, 1H), 7.64 (d, J=8.8 Hz, 1H), 7.70 (dd, J=8.8 Hz, 2.8 Hz, 1H), 7.91 (d, J=8.0 Hz, 1H), 7.99-8.02 (m, 1H), 8.13 (d, J=1.6 Hz, 1H), 8.40 (d, J=2.8 Hz, 1H), 8.66 (s, 1H), 10.34 (s, 1H), 10.90 (s, 1H).

Example 5: 2-Chloro-N-(4-chloro-3-(pyridin-2-yl)phenyl)-4-(N-(7-(hydroxyamino)-7-oxoheptyl)sulfamoyl)benzamide (Compound 59)

Step 5a. 4-Amino-2-chlorobenzoic acid (Compound 3002)

A mixture of 2-chloro-4-nitrobenzoic acid (5.0 g, 24.8 mmol), iron powder (8.0 g, 142.9 mmol) and NH$_4$Cl (7.6 g, 142.9 mmol) in EtOH/water (50/50 mL) was heated at reflux for 2 h. The hot mixture was filtered through Celite and washed with ethyl acetate. The mixture was separated and extracted with ethyl acetate. The combined organic layers were washed with water and brine, dried over anhydrous sodium sulfate. The crude product was purified by column chromatography (hexanes/ethyl acetate: 5/1, 3/1, 1/1) to afford compound 3002 as a white solid (1.0 g, 24% yield). $^1$H NMR (400 MHz, DMSO-d$_6$): δ 6.04 (s, 2H), 6.49 (dd, J=8.4 Hz, 2.0 Hz, 1H), 6.61 (d, J=2.0 Hz, 1H), 6.63 (d, J=8.8 Hz, 1H), 12.21 (br, 1H).

Step 5b. 2-Chloro-4-(chlorosulfonyl)benzoic acid (Compound 3003)

To a solution of 3002 (1.00 g, 5.4 mmol) in HOAc (20 mL) was added conc. HCl (5 mL) at 0° C. After 15 min, NaNO$_2$ aqueous solution (1.10 g, 16.2 mmol in water 4.5 mL) was added dropwise at -5~-10° C. and continued to stir at this temperature for 45 min.

The above reaction mixture was added dropwise to cuprous chloride (0.14 g, 1.4 mmol) and saturated sulfur dioxide in acetic acid (40 mL) at 0° C. After addition was complete the resulting mixture was warmed to 10° C. and stirred for 30 min. The reaction mixture was quenched with ice water and extracted with ethyl acetate. The combined organic layers were washed with water and brine, dried over anhydrous sodium sulfate. The crude product was purified by column chromatography (dichloromethane/methanol: 100/2, 100/5, 100/10) to afford compound 3003 as an off-white solid (500 mg, 34% yield).

Step 5c. 2-Chloro-4-(N-(7-ethoxy-7-oxoheptyl)sulfamoyl)benzoic acid (Compound 3004-59)

To a mixture of ethyl 7-aminoheptanoate hydrochloride (777 mg, 3.7 mmol) and N, N-diisopropylethylamine (4.0 g, 31.2 mmol) in dichloromethane (80 mL) was added compound 3003 (1.0 g, 3.9 mmol). The resulting mixture was stirred at room temperature overnight. The reaction mixture was adjusted pH to 6~7 with 2M HCl and extracted with ethyl acetate. The combined organic layers were washed with water and brine, dried over anhydrous sodium sulfate. The crude product was purified by column chromatography (dichloromethane/methanol: 100/2, 100/5, 100/10) to afford compound 3004-59 as a white solid (520 mg, 44% yield). LCMS: m/z 392.1 [M+1]$^+$. $^1$H NMR (400 MHz, CDCl$_3$): δ 1.25-1.33 (m, 7H), 1.44-1.62 (m, 4H), 2.28 (t, J=7.2 Hz, 2H), 2.98-3.02 (m, 2H), 4.13 (q, J=7.2 Hz, 2H), 5.07 (t, J=5.6 Hz, 1H), 7.82 (d, J=8.0 Hz, 1H), 7.97 (s, 1H), 8.08 (d, J=8.0 Hz, 1H).

Step 5d. Ethyl 7-(3-chloro-4-(4-chloro-3-(pyridin-2-yl)phenylcarbamoyl)phenyl sulfonamido)heptanoate (3005-59)

A mixture of 3004-59 (520 mg, 1.3 mmol), oxalyl chloride (1.59 g, 12.5 mmol) and DMF (0.05 mL) in dichloromethane was stirred at room temperature for 2 h. After evaporation, the residue was dissolved in dichloromethane, compound 1-8 (244 mg, 1.2 mmol) and N, N-diisopropylethylamine (325 mg, 2.5 mmol) were added. The reaction mixture was stirred at room temperature overnight. The reaction mixture was quenched with water and extracted with dichloromethane. The combined organic layers were washed with water and brine, dried over anhydrous sodium sulfate. The crude product was purified by column chromatography (hexanes/ethyl acetate: 5/1, 3/1, 1/1) to afford compound 3005-59 as a white solid (250 mg, 33% yield). LCMS: m/z 578.2 [M+1]$^+$. $^1$H NMR (400 MHz, DMSO-d$_6$): δ 1.13-1.22 (m, 7H), 1.38-1.49 (m, 4H), 2.22-2.27 (m, 2H), 2.76 (t, J=6.8 Hz, 2H), 4.03 (q, J=6.8 Hz, 2H), 7.44-7.47 (m, 1H), 7.59 (dd, J=8.4 Hz, 3.2 Hz, 1H), 7.69 (d, J=7.6 Hz, 1H), 7.74-7.79 (m, 1H), 7.85 (s, 2H), 7.91-7.95 (m, 3H), 8.02 (d, J=2.0 Hz, 1H), 8.71 (d, J=4.8 Hz, 1H), 10.93 (s, 1H).

Step 5e. 2-Chloro-N-(4-chloro-3-(pyridin-2-yl)phenyl)-4-(N-(7-(hydroxyamino)-7-oxoheptyl)sulfamoyl)benzamide (Compound 59)

A mixture of 3005-59 (150 mg, 0.2 mmol) in NH$_2$OH methanolic solution (10 mL, 1.79 M) was stirred at room temperature for 2.5 h. TLC showed reaction complete. The reaction mixture was adjusted pH to 5~6 with 2 M HCl, concentrated. The residue was triturated with water and filtered, purified by prep-HPLC to afford compound 59 as a white solid (46 mg, 32%). M.p.: 158.7~159.3° C. LCMS: m/z 565.2 [M+1]$^+$. $^1$H NMR (400 MHz, DMSO-d$_6$): δ 1.14-1.23 (m, 2H), 1.36-1.46 (m, 4H), 1.91 (t, J=7.2 Hz, 2H), 2.77 (q, J=6.4 Hz, 2H), 3.40-3.47 (m, 2H), 7.44-7.47 (m, 1H), 7.58 (d, J=8.8H, 1H), 7.69 (d, J=7.6 Hz, 1H), 7.75 (dd, J=8.4 Hz, 2.4 Hz, 1H), 7.83-7.85 (m, 3H), 7.91-7.95 (m, 2H), 8.02 (d, J=2.4 Hz, 1H), 8.71 (d, J=4.8 Hz, 1H), 10.32 (s, 1H), 10.89 (s, 1H).

Example 6: 2-{4-[2-Chloro-4-(4-chloro-3-pyridin-2-yl-phenylcarbamoyl)-benzenesulfonyl]-piperazin-1-yl}-pyrimidine-5-carboxylic acid hydroxyamide (Compound 86)

Step 6a. (Z)-ethyl-2-(ethoxymethyl)-3-methoxyacrylate (Compound 4002)

Sodium (27.6 g, 1.2 mol) was added to hexane (400 mL) and ethanol (27 g, 1.17 mol) was added dropwise at room temperature. The mixture was stirred at room temperature for 1 h. Then ethyl 3-ethoxypropanoate (88.0 g, 602 mmol) was added dropwise at 0° C. followed by ethyl formate (90 g, 1.22 mol). The reaction mixture was stirred at 0° C. for 2 h. and dimethyl sulfate (160 g, 1.27 mol) was added dropwise at the same temperature. The resulting mixture was heated at 50° C. overnight, filtered, and washed with hexane (300-500 mL). To the combined filtrate was added triethylammonium chloride (80 g, 0.58 mol) and sodium hydroxide (14.00 g, 0.35 mol). The mixture was stirred at room temperature for 4 h and filtered. The filtrate was washed with water, dried over $Na_2SO_4$ and concentrated. The residue was purified by distillation to give the desired compound 4002 (63.5 g, 56%) as a colorless oil. LCMS: m/z 211 $[M+23]^+$. $^1$H NMR (400 MHz, $CDCl_3$): δ 1.20 (t, J=7.2 Hz, 3H), 1.28 (t, J=7.2 Hz, 3H), 3.50 (q, J=7.2 Hz, 2H), 3.88 (s, 3H), 4.20 (m, 4H), 7.45 (s, 1H).

Step 6b. Ethyl 2-oxo-1,2,3,4-tetrahydropyrimidine-5-carboxylate (Compound 4003)

A mixture of compound 4002 (63.5 g, 337 mmol), urea (18.7 g, 312 mmol) and concentrated hydrochloric acid (16 mL) in ethanol (300 mL) was heated at reflux overnight. After evaporating the most of ethanol (~250 mL), the resulting suspension was filtered, washed with small amount of ethanol, and dried to give compound 4003 (23.5 g, 44%) as a white solid. LCMS: m/z 171 $[M+1]^+$. $^1$H NMR (400 MHz, $CDCl_3$): δ 1.27 (t, J=7.2 Hz, 3H), 4.19 (m, 4H), 5.28 (s, 1H), 7.21 (d, J=5.6 Hz, 1H), 7.40 (s, 1H).

Step 6c. Ethyl 2-oxo-1,2-dihydropyrimidine-5-carboxylate (Compound 4004)

To a solution of compound 4003 (23.5 g, 138 mmol) in acetic acid (300 mL) was added bromine (22.7 g, 142 mmol). The mixture was heated at reflux for 3 h and concentrated in vacuum to afford the hydrobromide salt of crude compound 4004 as a yellow solid. The product was used directly in next step without further purification. LCMS: m/z 169 $[M+1]^+$. $^1$H NMR (400 MHz, $CDCl_3$): δ 1.27 (t, J=7.2 Hz, 3H), 4.28 (q, J=7.2 Hz, 2H), 8.85 (s, 2H), 12.19 (br, s, 2H).

Step 6d. Ethyl 2-chloropyrimidine-5-carboxylate (Compound 4005)

A mixture of crude compound 4004 and phosphoryl trichloride (300 mL) was heated at reflux for 3 h, cooled to room temperature and concentrated. The residue was cooled to room temperature and dissolved in ethyl acetate (500 mL). The EtOAc solution was treated with ice water (300 mL) carefully, washed with ice-water and brine, dried over $Na_2SO_4$, evaporated, and purified by column chromatography (eluted with EtOAc/Hexane: 10%) to afford compound 4005 (14 g, 54%, two steps) as a white solid. LCMS: m/z 187 $[M+1]^+$. $^1$H NMR (300 MHz, $CDCl_3$): δ 1.42 (t, J=7.5 Hz, 3H), 4.48 (q, J=7.5 Hz, 2H), 9.15 (s, 2H).

Step 6e. Ethyl 2-(piperazin-1-yl)pyrimidine-5-carboxylate (Compound 4006)

A mixture of tert-butyl piperazine-1-carboxylate (1.1 g, 5.9 mmol) and 4005 (1 g, 5.4 mmol), $Et_3N$ (1.1 g, 10.8 mmol) in $CH_2Cl_2$ (10 mL) was stirred at room temperature for 2 h. The reaction mixture was washed with $H_2O$. The organic layer was concentrated. The residue was purified by chromatography eluting with Hexane/EtOAc=250:10, then 250:20 to afford the compound ethyl 2-(4-(tert-butoxycarbonyl)piperazin-1-yl)pyrimidine-5-carboxylate (900 mg, 45.4%) as a white solid. $^1$H NMR (400 MHz, $CDCl_3$): δ 1.37 (t, 3H, J=6.8 Hz), 1.49 (s, 9H), 3.51 (t, 4H, J=4.8 Hz), 3.92 (t, 4H, J=5.2 Hz), 4.35 (q, 2H, J=7.2 Hz), 8.85 (s, 2H).

A mixture of above product (500 mg, 1.49 mmol) and HCl/dioxane (10 mL) was stirred at room temperature for 2 h. The reaction mixture was concentrated. The residue was partitioned between EtOAc and saturated aq. $NaHCO_3$. The organic layer was washed with brine, dried over $Na_2SO_4$ and concentrated to afford the titled compound 4006 (370 mg, 88.2%) as a white solid. $^1$H NMR (400 MHz, $CDCl_3$): δ 1.39 (t, 3H, J=6.8 Hz), 2.96 (t, 4H, J=4.8 Hz), 3.95 (t, 4H, J=5.2 Hz), 4.36 (q, 2H, J=7.2 Hz), 8.86 (s, 2H).

Step 6f. 2-[4-(4-Carboxy-3-chloro-benzenesulfonyl)-piperazin-1-yl]-pyrimidine-5-carboxylic acid methyl ester (Compound 4007)

To a mixture of 4006 (1.04 g, 4.7 mmol) and DIPEA (4.0 g, 31.2 mmol) in dicholoromethane (80 mL) was added compound 3003 (1.0 g, 3.9 mmol). The mixture solution was stirred at room temperature overnight. The reaction mixture was adjusted pH to 6~7 with 2M HCl and extracted with ethyl acetate. The combined organic layers were washed with water and brine, dried over anhydrous sodium sulfate, evaporated in vacuo. The crude product was purified by column chromatography (methane/dichloromethane: 1/20) to afford compound 4007 as a white solid (520 mg, 30% yield). LCMS: m/z 455.2 $[M+1]^+$. $^1$H NMR (400 MHz, DMSO-$d_6$): δ 1.27 (t, J=7.2 Hz, 3H), 3.08 (br, 4H), 3.96 (br, 4H), 4.25 (q, J=7.2 Hz, 2H), 7.72 (dd, J=8.0 Hz, 1.6 Hz, 1H), 7.78 (d, J=1.2 Hz, 1H), 7.87 (d, J=8.0 Hz, 1H), 8.76 (s, 2H).

Step 6 g. 2-{4-[2-Chloro-4-(4-chloro-3-pyridin-2-yl-phenylcarbamoyl)-benzenesulfonyl]-piperazin-1-yl}-pyrimidine-5-carboxylic acid methyl ester (Compound 4008)

A mixture of 4007 (500 mg, 1.1 mmol), oxalyl chloride (1.59 g, 12.5 mmol) and DMF (0.05 mL) in dichloromethane (10 mL) was stirred at room temperature for 2 h. The reaction mixture was concentrated and the residue was dissolved in dichloromethane (15 mL). Compound 1-8 (278 mg, 1.2 mmol) and DIPEA (325 mg, 2.5 mmol) were added. The resulting mixture was stirred at room temperature overnight. The reaction mixture was quenched with water and extracted with dichloromethane. The combined organic layers were washed with water and brine, dried over anhydrous sodium sulfate and evaporated in vacuo. The crude product was purified by column chromatography (methanol/dichloromethane: 1/20) to afford compound 4008 as a white solid (180 mg, 25% yield). LCMS: m/z 641.2$[M+1]^+$. 1H NMR (400 MHz, DMSO-d$_6$): δ 1.28 (t, J=7.2 Hz, 3H), 3.11 (br, 4H), 3.99 (br, 4H), 4.26 (q, J=7.2 Hz, 2H), 7.43-7.46 (m, 1H), 7.58 (d, J=8.8 Hz, 1H), 7.69 (d, J=8.0 Hz, 1H), 7.72 (dd, J=8.8 Hz, 2.8 Hz, 1H), 7.83 (dd, J=8.0 Hz, 1.2 Hz, 1H), 7.88-7.91 (m, 2H), 7.93 (dd, J=8.0 Hz, 2.0 Hz, 1H), 7.99 (d, J=2.8 Hz, 1H), 8.71 (d, J=4.4 Hz, 1H), 8.78 (s, 2H), 10.84 (s, 1H).

Step 6 h. 2-{4-[2-Chloro-4-(4-chloro-3-pyridin-2-yl-phenylcarbamoyl)-benzenesulfonyl]-piperazin-1-yl}-pyrimidine-5-carboxylic acid hydroxyamide (Compound 86)

A mixture of 4008 (180 mg, 0.3 mmol) and NH$_2$OH (15 mL, 1.79M) methanolic solution was stirred at room temperature for 2.5 h. The reaction mixture was adjusted pH to 5~6 with 2M HCl and evaporated. The resulting mixture was filtered. The crude product was purified by prep-HPLC to afford compound 86 as a white solid (50 mg, 26% yield). M.p.: 158.7-159.3° C. LCMS: m/z 628.2 [M+1]$^+$. $^1$H NMR (400 MHz, DMSO-d$_6$): δ 3.09 (br, 4H), 3.93 (br, 4H), 7.43-7.46 (m, 1H), 7.58 (d, J=8.4 Hz, 1H), 7.69-7.73 (m, 2H), 7.83 (dd, J=8.0 Hz, 1.2 Hz, 1H), 7.87-7.90 (m, 2H), 7.93 (dd, J=7.6 Hz, 1.6 Hz, 1H), 7.99 (d, J=2.4 Hz, 1H), 8.66 (s, 2H), 8.70 (d, J=4.0 Hz, 1H), 9.02 (s, 1H), 10.84 (s, 1H), 11.09 (s, 1H).

Example 7: N-(4-Chloro-3-(5-(dimethylamino)-1H-benzo[d]imidazol-2-yl)phenyl)-3-(7-(hydroxyamino)-7-oxoheptyloxy)benzamide (Compound 111)

Step 7a. 3-(4-Chloro-3-(5-(dimethylamino)-1H-benzo[d]imidazol-2-yl)phenylcarbamoyl)phenyl acetate (Compound 5001-111)

3-Acetoxybenzoic acid (2.6 g, 0.015 mol) was added to a mixture of compound 2-3 (3.5 g, 0.012 mol), HATU (6.9 g, 0.018 mol) and Et$_3$N (2.5 mL, 0.018 mol) in dichloromethane (30 mL). The reaction mixture was stirred at room temperature overnight. The mixture was quenched with water and extracted with dichloromethane. The combined organic layers were washed with water and brine, dried over anhydrous Na$_2$SO$_4$. The crude product was purified by column chromatography (hexanes/ethyl acetate: 1/1) to afford compound 5001-111 as a white solid (2.6 g, 49% yield). LCMS: m/z 449.2 [M+1]$^+$.

Step 7b. N-(4-Chloro-3-(5-(dimethylamino)-1H-benzo[d]imidazol-2-yl)phenyl)-3-hydroxybenzamide (Compound 5002-111)

To a solution of compound 5001-111 (1.0 g, 0.002 mol) in MeOH (15 mL) was added a solution of NaOH (0.89 g, 0.02 mol) in H$_2$O (15 mL). The reaction mixture was heated at reflux overnight. After cooling at ice bath, the mixture was adjusted pH to 7~8 with 1M HCl and extracted with ethyl acetate. The combined organic layers were washed with water and brine, dried over anhydrous Na$_2$SO$_4$, evaporated in vacuo to afford crude compound 5002-111 as a yellow solid (0.81 g, 100% yield). LCMS: m/z 407.2 [M+1]$^+$.

Step 7c. Ethyl-7-(3-(4-chloro-3-(5-(dimethylamino)-1H-benzo[d]imidazol-2-yl)phenylcarbamoyl)phenoxy)heptanoate (Compound 5003-111)

To a mixture of compound 5002-111 (1.40 g, 0.0034 mol), ethyl 7-hydroxyheptanoate (0.89 g, 0.0052 mol) and PPh$_3$ (1.8 g, 0.0069 mol) in anhydrous THF (20 mL) was added DIAD (1.39 g, 0.0069 mol) at 0° C. under nitrogen atmosphere. The resulting solution was heated at 65° C. overnight. After cooling to room temperature, the reaction mixture was concentrated in vacuo. The crude product was purified by column chromatography (dichloromethane/ethyl acetate: 1:1) to afford compound 5003-111 as a white solid (0.9 g, 47% yield). LCMS: m/z 563.3 [M+1]$^+$.

Step 7d. N-(4-Chloro-3-(5-(dimethylamino)-1H-benzo[d]imidazol-2-yl)phenyl)-3-(7-(hydroxyamino)-7-oxoheptyloxy)benzamide (Compound 111)

Compound 5003-111 (120 mg, 0.21 mmol) was taken into NH$_2$OH methanolic solution (10 mL, 1.79 M). The mixture stirred at room temperature for 40 min. The reaction mixture was adjusted pH to 8-9 with acetic acid and concentrated in vacuo. The residue was purified by prep-HPLC to afford compound 111 as a white solid (30 mg, 26% yield). M.p: 140~142° C. LCMS: m/z 550.3 [M+1]$^+$. $^1$HNMR (400 MHz, DMSO-d$_6$): δ 1.28-1.35 (m, 2H), 1.40-1.56 (m, 4H), 1.72-1.76 (m, 2H), 1.96 (t, J=3.2 Hz, 2H), 2.93 (s, 6H), 4.05 (t, J=6.4 Hz, 2H), 6.84 (d, J=8.4 Hz, 2H), 7.16-7.18 (m, 1H), 7.43-7.61 (m, 5H), 7.97 (dd, J=8.8 Hz, 2.4 Hz, 1H), 8.23 (s, 1H), 8.42 (d, J=2.4 Hz, 1H), 10.36 (s, 1H), 10.47 (s, 1H), 12.23 (br, 1H).

Example 8: 2-((3-Chloro-4-(4-chloro-3-(pyridin-2-yl)phenylcarbamoyl)benzyl)(methyl)amino)-N-hydroxypyrimidine-5-carboxamide (Compound 263)

Step 8a. 1-Bromo-4-(bromomethyl)-2-chlorobenzene (Compound 6002)

A mixture of 1-bromo-2-chloro-4-methylbenzene (5 g, 24 mmol), NBS (5.19 g, 29 mmol), AIBN (0.39 g, 2.0 mmol) in CCl$_4$ (50 mL) was heated at reflux overnight. The hot reaction mixture was filtered and rinsed with CCl$_4$. The combined organic layer was washed with water and brine, dried over NaSO$_4$, evaporated in vacuo to afford compound 6002 as a white solid (5.6 g, 82% yield). $^1$H NMR (400 MHz, CDCl$_3$): δ 4.39 (s, 2H), 7.14 (dd, J=8.0 Hz, 2.0 Hz, 1H), 7.48 (d, J=2.4 Hz, 1H), 7.58 (d, J=8.4 Hz, 1H).

Step 8b. tert-Butyl 4-bromo-3-chlorobenzyl(methyl)carbamate (Compound 6003)

To a stirring solution of MeNHBoc in DMF (10 mL) cooled to 0° C. was added sodium hydride (590 mg, 24.6 mmol). The resulting mixture was stirred for 10 min followed by the addition of a solution of 6002 (4.67 g, 16.0 mmol) in DMF (5 mL). The reaction mixture was warmed to room temperature and stirred for 8 h. The reaction mixture was quenched with ice water and extracted with ethyl acetate. The combined organic layers were washed with water and brine, dried over anhydrous sodium sulfate and evaporated in vacuo. The crude product was purified by column chromatography (ethyl acetate/hexanes: 1/10) to afford 6003 as a white solid (1.8 g, 34% yield). $^1$H NMR (400 MHz, CDCl$_3$): δ 1.47 (s, 9H), 2.83 (d, J=18.4 Hz, 3H), 4.35 (s, 2H), 6.99 (s, 1H), 7.32 (s, 1H), 7.56 (d, J=8.4 Hz, 1H).

Step 8c. tert-Butyl 3-chloro-4-formylbenzyl(methyl)carbamate (Compound 6004)

To a solution of 6003 (2.15 g, 6.4 mmol) in anhydrous THF (20 mL) was added n-BuLi (3.8 mL, 2.5 M, 9.5 mmol) dropwise at −78° C. The resulting mixture was continued to stir for 2 h followed by the addition of N-formyl morpholine (884 mg, 7.7 mmol) at −78° C. The resulting mixture was warmed to room temperature and stirred overnight. The reaction mixture was quenched with water and extracted with ethyl acetate. The combined organic layers were washed with water and brine, dried over anhydrous sodium sulfate and evaporated in vacuo. The crude product was purified by column chromatography (ethyl acetate/hexanes: 1/10) to afford compound 6004 as a red oil (570 mg, 25% yield). LCMS: m/z 282.1 [M−1]$^-$. $^1$H NMR (400 MHz, CDCl$_3$): δ 1.45, 1.50 (two single peaks, 9H), 2.85, 2.90 (two single peaks, 3H), 4.46 (br, 2H), 7.23 (d, J=6.8 Hz, 1H), 7.31 (s, 1H), 7.90 (d, J=8.0 Hz, 1H), 10.45 (s, 1H).

Step 8d. Ethyl 2-((3-chloro-4-formylbenzyl)(methyl)amino)pyrimidine-5-carboxylate (Compound 6005)

A mixture of 6004 (570 mg, 2.0 mmol) in TFA (10 mL) was stirred at room temperature for 2 h. The reaction mixture was concentrated. The residue was mixed with 4005 (560 mg, 3.0 mmol) and TEA (10 ml) and the resulting mixture was stirred at room temperature overnight. The reaction mixture was quenched with water and extracted with ethyl acetate. The combined organic layers were washed with water and brine, dried over Na$_2$SO$_4$. The crude product was purified by column chromatography (ethyl acetate/hexanes: 1/5) to afford compound 6005 as a yellow solid (425 mg, 65% yield). LCMS: m/z 334.1 [M+1]$^+$. $^1$H NMR (400 MHz, DMSO-d$_6$): δ 1.29 (t, J=7.2 Hz, 3H), 3.22 (s, 3H), 4.27 (q, J=7.2 Hz, 2H), 5.02 (s, 2H), 7.36 (d, J=8.0 Hz, 1H), 7.47 (s, 1H), 7.83 (d, J=8.0 Hz, 1H), 8.79, 8.86 (two single peaks, 2H), 10.29 (s, 1H).

Step 8e. 2-Chloro-4-(((5-(ethoxycarbonyl)pyrimidin-2-yl)(methyl)amino)methyl)benzc acid (Compound 6006)

A mixture of compound 6005 (425 mg, 1.27 mmol), NaIO$_4$ (408 mg, 1.9 mmol), RuCl$_3$ (40 mg, 0.2 mmol) in CH$_3$CN (15 mL) was stirred at room temperature for 16 h. The reaction mixture was quenched with water and extracted with ethyl acetate. The combined organic layers were washed with water and brine, dried over Na$_2$SO$_4$. The crude compound 6006 was obtained as a white solid (188 mg) which used directly for the next step. LCMS: m/z 350.1 [M+1]$^+$. $^1$H NMR (400 MHz, DMSO-d$_6$): δ 1.29 (t, J=7.2 Hz, 3H), 3.21 (s, 3H), 4.28 (q, J=7.2 Hz, 2H), 4.98 (s, 2H), 7.26 (d, J=8.0 Hz, 1H), 7.40 (s, 1H), 7.76 (d, J=7.6 Hz, 1H), 8.80, 8.86 (two single peaks, 2H).

Step 8f. Ethyl 2-((3-chloro-4-(4-chloro-3-(pyridin-2-yl)phenylcarbamoyl)benzyl) (methyl)amino)pyrimidine-5-carboxylate (Compound 6007)

A mixture of 6006 (118 mg, 0.3 mmol) in DMF (0.10 mL), thionyl chloride (2 mL, 27.5 mmol) was stirred at room temperature overnight. The reaction mixture was concentrated and the residue was dissolved in anhydrous dichloromethane (5 mL) and cooled at ice bath. To the mixture was added DIPEA (1.0 mL, 6.0 mmol) and compound 1-8 (83 mg, 0.4 mmol) and the resultuing mixture was warmed to room temperature and stirred overnight. The reaction was quenched with water and extracted with ethyl acetate. The combined organic layers were washed with water and brine, dried over NaSO$_4$. The crude product was purified by column chromatography (ethyl acetate/dichloromethane: 5/1) to afford compound 6007 as a white solid (100 mg 50% yield). LCMS: m/z 536.2 [M+1]$^+$. $^1$H NMR (400 MHz, DMSO-d$_6$): δ 1.29 (t, J=7.2 Hz, 3H), 3.22 (s, 3H), 4.28 (q, J=7.2 Hz, 2H), 4.99 (s, 2H), 7.31 (d, J=7.6 Hz, 1H), 7.43-7.45 (m, 2H), 7.54-7.58 (m, 2H), 7.68 (d, J=7.6 Hz, 1H), 7.75 (dd, J=8.8 Hz, 2.4 Hz, 1H), 7.90-7.94 (m, 1H), 8.02 (d, J=2.8 Hz, 1H), 8.70 (d, J=4.4 Hz, 1H), 8.82-8.86 (m, 2H), 10.71 (s, 1H).

Step 8 g. 2-((3-Chloro-4-(4-chloro-3-(pyridin-2-yl) phenylcarbamoyl)benzyl) (methyl)amino)-N-hydroxypyrimidine-5-carboxamide (Compound 263)

Compound 6007 (100 mg, 0.2 mmol) was taken into NH$_2$OH methanolic solution (10 mL, 1.79 M). The resulting mixture was stirred at room temperature for 2 h. The reaction mixture was adjusted pH to 7~8 with acetic acid and concentrated. The residue was triturated with water and filtered to afford compound 263 as a white solid (60 mg, 60% yield). LCMS: m/z 523.2 [M+1]$^+$. $^1$H NMR (400 MHz, DMSO-d$_6$): 3.19 (s, 3H), 4.96 (s, 2H), 7.29 (d, J=8.0 Hz, 1H), 7.42-7.46 (m, 2H), 7.54-7.57 (m, 2H), 7.67 (d, J=8.0 Hz, 1H), 7.75 (d, J=8.8 Hz, 2.8 Hz, 1H), 7.90-7.94 (m, 1H), 8.01 (d, J=2.4 Hz, 1H), 8.70 (d, J=4.4 Hz, 1H), 8.74 (s, 2H), 9.03 (s, 1H), 10.75 (s, 1H), 11.21 (s, 1H).

Example 9: 2-(3-Chloro-4-(4-chloro-3-(pyridin-2-yl) phenylcarbamoyl) phenylsulfonamido)-N-hydroxypyrimidine-5-carboxamide (Compound 265)

Step 9a. Methyl 2-chloro-4-sulfamoylbenzoate (Compound 7001)

Compound 3003 (200 mg, 0.7 mmol) was dissolved in dichloromethane (5 mL) followed by the addition of saturated NH$_3$ methanolic solution (0.5 mL) at 0° C. After addition, the reaction mixture was warmed to room temperature and stirred for 5 min. After evaporation, the residue was purified by column chromatography (hexanes/ethyl acetate: 3/1) to afford compound 7001 as a white solid (160 mg, 86% yield). LCMS: m/z 248.0[M−1]$^-$. $^1$H NMR (400 MHz, DMSO-d$_6$): δ 3.91 (s, 3H), 7.69 (s, 2H), 7.88 (dd, J=8.4 Hz, 1.6 Hz, 1H), 7.97 (d, J=1.2 Hz, 1H), 8.02 (d, J=8.0 Hz, 1H).

Step 9b. 4-(N-(tert-Butoxycarbonyl)sulfamoyl)-2-chlorobenzoic acid (Compound 7002)

A mixture of 7001 (1.44 g, 5.8 mmol), Boc$_2$O (2.51 g, 11.5 mmol) and DMAP (71 mg) in dichloromethane (30 mL) was heated at reflux overnight. After cooling to room temperature, the mixture was quenched with water, extracted with ethyl acetate. The combined organic layers were washed with water and brine, dried over anhydrous Na$_2$SO$_4$. The crude product was purified by column chromatography (hexanes/ethyl acetate: 2/1) to afford compound methyl 4-(N-(tert-butoxycarbonyl)sulfamoyl)-2-chlorobenzoate as a white solid (1.20 g, 60% yield). LCMS: m/z 350.2 [M+1]$^+$. $^1$H NMR (400 MHz, DMSO-d$_6$): δ 1.32 (s, 9H), 3.91 (s, 3H), 7.94 (dd, J=8.0 Hz, 1.6 Hz, 1H), 7.97 (d, J=1.6 Hz, 1H), 8.07 (d, J=8.0 Hz, 1H), 12.03 (br, 1H).

A mixture of above product (1.22 g, 3.5 mmol), LiOH (1.46 g, 34.9 mmol) in THF/H$_2$O (10 mL/10 mL) was stirred at room temperature overnight. After evaporation, the mixture was adjusted to pH 1~2 with 1M HCl and extracted with ethyl acetate. The combined organic layers were washed with water and brine, evaporated in vacuo to afford compound 7002 as a white solid (1.00 g, 85% yield). LCMS: m/z 334.0 [M−1]$^-$. $^1$H NMR (400 MHz, DMSO-d$_6$): δ 1.32 (s, 1H), 7.90 (dd, J=8.0 Hz, 1.6 Hz, 1H), 7.94 (d, J=1.6 Hz, 1H), 8.02 (d, J=8.4 Hz, 1H), 11.99 (br, 1H).

Step 9c. tert-Butyl 3-chloro-4-(4-chloro-3-(pyridin-2-yl)phenylcarbamoyl)phenyl sulfonylcarbamate (Compound 7003)

A mixture of compound 7002 (328 mg, 1.0 mmol), 1-8 (100 mg, 0.5 mmol), HATU (559 mg, 1.5 mmol), DIPEA (253 mg, 2.0 mmol) in DMF (5 mL) was stirred at room temperature overnight. The mixture was quenched with saturated sodium bicarbonate and extracted with ethyl acetate. The combined organic layers were washed with water and brine, dried over anhydrous Na$_2$SO$_4$. The crude product was purified by column chromatography (dichloromethane/ethyl acetate: 2/1) to afford compound 7003 as a white solid (270 mg, ~100% yield). LCMS: m/z 522.2 [M+1]$^+$. $^1$H NMR (400 MHz, DMSO-d$_6$): δ 1.36 (s, 9H), 7.44-7.47 (m, 1H), 7.59 (d, J=8.8 Hz, 1H), 7.70 (d, J=8.0 Hz, 1H), 7.76 (dd, J=8.8 Hz, J=2.4 Hz, 1H), 7.91-7.98 (m, 4H), 8.01 (d, J=2.4 Hz, 1H), 8.71 (d, J=4.4 Hz, 1H), 10.93 (s, 1H), 11.98 (br, 1H).

Step 9d. 2-Chloro-N-(4-chloro-3-(pyridin-2-yl)phenyl)-4-sulfamoylbenzamide (Compound 7004)

A mixture of 7003 (270 mg, 0.5 mmol) in TFA (5 mL) was stirred at room temperature for 2 h. After evaporation, the mixture was quenched with saturated NaHCO$_3$ and extracted with ethyl acetate. The combined organic layers were washed with water and brine, dried over anhydrous Na$_2$SO$_4$, evaporated in vacuo to afford compound 7004 as a white solid (180 mg, 84% yield). LCMS: m/z 422.1 [M+1]$^+$. $^1$H NMR (400 MHz, DMSO-d$_6$): δ 7.43-7.47 (m, 1H), 7.58 (d, J=8.8 Hz, 1H), 7.64 (s, 2H), 7.69 (d, J=8.0 Hz, 1H), 7.75 (dd, J=8.8 Hz, 2.4 Hz, 1H), 7.82-7.88 (m, 2H), 7.91-7.96 (m, 2H), 8.01 (d, J=2.4 Hz, 1H), 8.71 (d, J=4.8 Hz, 1H), 10.88 (s, 1H).

Step 9e. Ethyl 2-(3-chloro-4-(4-chloro-3-(pyridin-2-yl)phenylcarbamoyl)phenyl sulfonamido)pyrimidine-5-carboxylate (Compound 7005)

A mixture of compound 7004 (460 mg, 1.1 mmo), 4005 (203 mg, 1.1 mmol), cesium carbonate (533 mg, 1.6 mmol), Xantphos (20 mg, 0.03 mmol), Pd$_2$(dba)$_3$ (20 mg, 0.02 mmol) in 1,4-dioxane (15 mL) was heated at 85° C. overnight. After cooling to room temperature, the reaction mixture was quenched with water and extracted with ethyl acetate. The combined organic layers were washed with water and brine, dried over anhydrous Na$_2$SO$_4$. The crude product was purified by column chromatography (dichloromethane/ethyl acetate: 2/1) to afford compound 7005 as a pale yellow solid (300 mg, 48% yield). LCMS: m/z 572.1 [M+1]$^+$. $^1$H NMR (400 MHz, DMSO-d$_6$): δ 1.29 (t, J=7.2 Hz, 3H), 4.29 (q, J=7.2 Hz, 2H), 7.43-7.46 (m, 1H), 7.57 (d, J=8.8 Hz, 1H), 7.67-7.73 (m, 2H), 7.84 (d, J=8.0 Hz, 1H), 7.90-7.94 (m, 1H), 7.99 (d, J=2.8 Hz, 1H), 8.06 (dd, J=8.0 Hz, 1.6 Hz, 1H), 8.10 (d, J=1.6 Hz, 1H), 8.69-8.71 (m, 1H), 8.96 (s, 2H), 9.05 (s, 1H).

Step 9f. 2-(3-Chloro-4-(4-chloro-3-(pyridin-2-yl)phenylcarbamoyl)phenylsulfonamido)-N-hydroxypyrimidine-5-carboxamide (Compound 265)

Compound 7005 (300 mg, 0.5 mmol) was taken into NH$_2$OH methanolic solution (10 mL, 1.79 M). The resulting mixture was stirred at room temperature for 1 h. The reaction mixture was adjusted pH to 7~8 with acetic acid and concentrated. The residue was triturated with water and filtered. The solid was suspended in dichloromethane and stirred at room temperature overnight and filtered. The collected solid was dried in vacuo to afford compound 265 as a white solid (60 mg, 21% yield). M.p: 215~220° C. LCMS: m/z 559.2 [M+1]$^+$. $^1$H NMR (400 MHz, DMSO-d$_6$): δ 7.42-7.46 (m, 1H), 7.56 (d, J=8.8 Hz, 1H), 7.64 (d, J=8.0 Hz, 1H), 7.68 (d, J=8.0 Hz, 1H), 7.73 (dd, J=8.8 Hz, 2.8 Hz, 1H), 7.85 (d, J=8.0 Hz, 1H), 7.90-7.94 (m, 2H), 8.01 (d, J=2.4 Hz, 1H), 8.53 (s, 2H), 8.70 (d, J=4.4 Hz, 1H), 8.93 (s, 1H), 10.79 (s, 1H), 10.96 (br, 1H).

Example 10: (E)-2-Chloro-N-(4-chloro-3-(pyridin-2-yl)phenyl)-4-(N-(3-(3-(hydroxyamino)-3-oxoprop-1-enyl)phenyl)sulfamoyl)benzamide (Compound 254)

Step 10a. 2-(3-Nitrophenyl)-1,3-dioxolane (Compound 8002)

A mixture of 3-nitrobenzaldehyde (7.0 g, 46.3 mmol), ethylene glycol (14.4 g, 231.5 mmol), p-toluenesulfonic acid (0.79 g, 4.6 mmol) in toluene (80 mL) was heated at reflux overnight. After cooling to room temperature, the reaction mixture was quenched with aqueous sodium bicarbonate and extracted with ethyl acetate. The combined organic layers were washed with water and brine, dried over anhydrous Na$_2$SO$_4$ and evaporated in vacuo to afford compound 8002 as a yellow oil (8.6 g, 95%). $^1$H NMR (400 MHz, CDCl$_3$): δ 4.05-4.11 (m, 2H), 4.12-4.16 (m, 2H), 5.89 (s, 1H), 7.56 (t, J=8.0 Hz, 1H), 7.81 (d, J=7.6 Hz, 1H), 8.21-8.24 (m, 1H), 8.35-8.36 (m, 1H).

Step 10b. 3-(1,3-Dioxolan-2-yl)aniline (Compound 8003)

A mixture of 8002 (215 mg, 1.1 mmol), Pd/C (100 mg, 50%) in ethanol (10 mL) was stirred under hydrogen at room temperature overnight. The mixture was filtered and the filtrate was evaporated in vacuo. The crude product was purified by column chromatography (hexanes/ethyl acetate: 8/1) to afford compound 8003 as a yellow solid (100 mg, 55%). LCMS: m/z 166.1 [M+1]$^+$. $^1$H NMR (400 MHz, DMSO-d$_6$): δ 3.86-4.03 (m, 4H), 5.10 (s, 1H), 5.55 (s, 1H), 6.54 (d, J=7.6 Hz, 2H), 6.63 (s, 1H), 6.99 (t, J=7.6 Hz, 1H).

Step 10c. Methyl 4-(N-(3-(1,3-dioxolan-2-yl)phenyl)sulfamoyl)-2-chlorobenzoate (Compound 8004)

A mixture of 8003 (1.12 g, 6.8 mmol), 3003 (2.21 g, 8.2 mmol), anhydrous pyridine (1.3 g, 16.4 mmol) in anhydrous CH$_2$Cl$_2$ (10 mL) was heated at reflux for 30 min. The mixture was quenched with water and adjusted pH to 2-3 with HCl (1.0M). The resulting mixture was extracted with ethyl acetate. The combined organic layers were washed with water and brine, dried over anhydrous sodium sulfate and evaporated in vacuo. The crude product was purified by column chromatography (hexanes/ethyl acetate: 10/1) to afford compound 8004 as a yellow oil (2.16 g, 80%). LCMS: m/z 398.1 [M+1]$^+$. $^1$H NMR (400 MHz, DMSO-d$_6$): δ 3.87 (s, 3H), 3.91-3.93 (m, 2H), 3.94-3.96 (m, 2H), 5.66 (s, 1H), 7.10-7.17 (m, 3H), 7.29 (t, J=8 Hz, 1H). 7.77 (dd, J=8.0 Hz, 1.6 Hz, 1H), 7.85 (d, J=1.6 Hz, 1H), 7.96 (d, J=8.0 Hz, 1H), 10.58 (s, 1H).

Step 10d. 4-(N-(3-(1,3-Dioxolan-2-yl)phenyl)sulfamoyl)-2-chlorobenzoic acid (Compound 8005)

LiOH (264 mg, 6.25 mmol) was added into a solution of 8004 (500 mg, 1.25 mmol) in THF/H$_2$O (5 mL/5 mL). The mixture was stirred at room temperature overnight. The mixture was quenched with HCl (1 M) and adjusted pH to 1-2. The resulting mixture was extracted with ethyl acetate. The combined organic layers were washed with water and brine, dried over anhydrous sodium sulfate and evaporated in vacuo to afford compound 8005 as a red solid (450 mg, 94%). LCMS: m/z 384.1 [M+1]$^+$. $^1$H NMR (400 MHz, DMSO-d$_6$): 3.91-3.93 (m, 2H), 3.95-3.97 (m, 2H), 5.67 (s, 1H), 7.11-7.18 (m, 3H), 7.30 (t, J=8.0 Hz, 1H). 7.74 (dd, J=8.4 Hz, 2.0 Hz, 1H), 7.83 (d, J=1.6 Hz, 1H), 7.92 (d, J=8.4 Hz, 1H), 10.57 (s, 1H).

Step 10e. 4-(N-(3-(1,3-Dioxolan-2-yl)phenyl)sulfamoyl)-2-chloro-N-(4-chloro-3-(pyridin-2-yl)phenyl) benzamide (Compound 8006)

A mixture of 8005 (284 mg, 0.74 mmol), 1-8 (100 mg, 0.49 mmol), HATU (373 mg, 0.98 mmol), DIPEA (159 mg, 1.23 mmol) in anhydrous DMF (5 mL) was stirred overnight. The mixture was quenched with water and extracted with ethyl acetate. The combined organic layers were washed with water and brine, dried over anhydrous sodium sulfate and evaporated in vacuo. The crude product was purified by column chromatography (hexanes/ethyl acetate: 5/1) to afford compound 8006 as a yellow solid (248 g, 88%). LCMS: m/z 570.2 [M+1]$^+$.

Step 10f. 2-chloro-N-(4-chloro-3-(pyridin-2-yl)phenyl)-4-(N-(3-formylphenyl) sulfamoyl)benzamide (Compound 8007)

A mixture of 8006 (120 mg, 0.18 mmol) and HCl (5 mL) in THF/H$_2$O (5 mL/5 mL) was refluxed for 1 h. The mixture was quenched with water and extracted with ethyl acetate. The combined organic layers were washed with water and brine until pH 7. The organic layer was dried over anhydrous Na$_2$SO$_4$ and evaporated in vacuo. The crude product was purified by column chromatography (hexanes/ethyl acetate: 5/1) to afford compound 8007 as a yellow solid (90 mg, 82%). LCMS: m/z 526.2 [M+1]$^+$. $^1$H NMR (400 MHz, DMSO-d$_6$): 7.42-7.50 (m, 2H), 7.53-7.57 (m, 2H), 7.60-7.72 (m, 5H), 7.81-7.86 (m, 2H), 7.91 (dd, J=7.6 Hz, 1.6 Hz, 1H), 7.94 (br, 1H), 7.96 (d, J=2.4 Hz, 1H), 8.70 (d, J=4.8 Hz, 2H), 9.94 (s, 1H), 10.84 (s, 1H), 10.91 (s, 1H).

Step 10 g. (E)-methyl 3-(3-(3-chloro-4-(4-chloro-3-(pyridin-2-yl)phenylcarbamoyl) phenylsulfonamido) phenyl)acrylate (Compound 8008)

A mixture of 8007 (110 mg, 0.21 mmol), methyl-(dimethoxyphosphoryl) acetate (58 mg, 0.32 mmol) and sodium methoxide (34 mg, 0.63 mmol) in anhydrous DMF was stirred at room temperature overnight. The mixture was quenched with HCl (1 M) and extracted with ethyl acetate. The combined organic layers were washed with water and brine, dried over anhydrous sodium sulfate and evaporated in vacuo. The crude product was purified by column chromatography (CH$_2$Cl$_2$/ethyl acetate: 6/1) to afford compound 8008 as a yellow solid (45 mg, 37%). LCMS: m/z 582.2 [M+1]$^+$. $^1$H NMR (400 MHz, DMSO-d$_6$): 3.72 (s, 3H), 6.52 (d, J=16.4 Hz, 1H), 7.19 (d, J=8.4 Hz, 1H), 7.34 (t, J=7.2 Hz, 1H), 7.41-7.49 (m, 3H), 7.55-7.61 (m, 2H), 7.66-7.72 (m, 2H), 7.80-7.86 (m, 2H), 7.90 (dd, J=8.0 Hz, 2.0 Hz, 1H), 7.93-7.96 (m, 2H), 8.70 (d, J=4.4 Hz, 1H), 10.71 (s, 1H), 10.83 (s, 1H).

Step 10 h. (E)-2-Chloro-N-(4-chloro-3-(pyridin-2-yl)phenyl)-4-(N-(3-(3-(hydroxyamino)-3-oxoprop-1-enyl)phenyl)sulfamoyl)benzamide (Compound 254)

Compound 8008 (45 mg, 0.077 mmol) was taken into NH$_2$OH methanolic solution (10 mL, 1.79 M). The resulting mixture was stirred at room temperature for 1 h. The reaction mixture was adjusted pH to 7~8 with acetic acid and concentrated. The residue was triturated with water and filtered. The collected solid was purified with prep-HPLC to afford compound 254 as an off-white solid (13 mg, 31% yield). M.p.: 217~221° C. LCMS: m/z 583.2 [M+1]$^+$. $^1$H NMR (400 MHz, DMSO-d$_6$): 6.41 (d, J=15.6 Hz, 1H), 7.12 (d, J=7.6, 1H), 7.18 (s, 1H), 7.25-7.38 (m, 4H), 7.42-7.45 (m, 1H), 7.56 (d, J=8.8 Hz, 1H), 7.66-7.72 (m, 2H), 7.80-7.90 (m, 1H), 7.90-7.97 (m, 3H), 8.70 (d, J=4.4 Hz, 1H), 10.71 (s, 1H), 10.80 (br, 1H), 10.84 (s, 1H).

Example 11: 2-(4-((3-Chloro-4-(4-chloro-3-(pyridin-2-yl)phenylcarbamoyl) phenylsulfonamido) methyl)piperidin-1-yl)-N-hydroxypyrimidine-5-carboxamide (Compound 90)

Step 11a. tert-Butyl 4-((3-chloro-4-(methoxycarbonyl)phenylsulfonamido)methyl) piperidine-1-carboxylate (Compound 9001)

To a mixture of tert-butyl 4-(aminomethyl)piperidine-1-carboxylate (570 mg, 2.6 mmol) and 3003 (600 mg, 2.2 mmol) in dichloromethane (10 mL) was added triethylamine (0.6 mL, 4.4 mmol). The mixture was stirred at room temperature overnight. The reaction mixture was diluted with ethyl acetate and washed with 1N HCl. The ethyl acetate layer was concentrated in vacuo and purified by column chromatography (hexanes:ethyl acetate=5:1) to give compound 9001 as a white solid (610 mg, 62% yield). LCMS: m/z 445.1 [M−1]$^-$. $^1$H NMR (400 MHz, DMSO-d6): δ 0.87-0.98 (m, 2H), 1.37 (s, 9H), 1.49-1.60 (m, 3H), 2.62-2.70 (m, 4H), 3.86 (br, 2H), 3.90 (s, 3H), 7.84 (dd, J=8.0 Hz, 1.6 Hz, 1H), 7.91 (d, J=1.6 Hz, 1H), 7.94 (t, J=5.6 Hz, 1H), 8.01 (d, J=8.0 Hz, 1H).

Step 11b. 4-(N-((1-(tert-Butoxycarbonyl)piperidin-4-yl)methyl)sulfamoyl)-2-chlorobenzoic acid (Compound 9002)

To the solution of 9001 (610 mg, 1.4 mmol) in THF (16 mL) and H$_2$O (8 mL) was added LiOH (286 mg, 12.0 mmol). The mixture was stirred at room temperature for 3 h. The reaction mixture was acidified to pH=5 with 1N HCl and extracted with ethyl acetate. The ethyl acetate layer was dried over Na$_2$SO$_4$, filtered and concentrated in vacuo to give compound 9002 as a white solid (530 mg, 90% yield).

¹H NMR (400 MHz, DMSO-d₆): δ 0.89-0.98 (m, 2H), 1.37 (s, 9H), 1.52-1.61 (m, 3H), 2.65-2.69 (m, 4H), 3.89 (d, J=12.0 Hz, 2H), 7.80 (d, J=8.0 Hz, 1H), 7.87 (s, 1H), 7.91 (t, J=6.0 Hz, 1H), 7.95 (d, J=8.0 Hz, 1H).

Step 11c. tert-Butyl 4-((3-chloro-4-(4-chloro-3-(pyridin-2-yl)phenylcarbamoyl)phenyl sulfonamido)methyl)piperidine-1-carboxylate (Compound 9003)

To a mixture of 9002 (530 mg, 1.2 mmol) and 1-8 (200 mg, 1.0 mmol) in DMF (2.0 mL) was added DIPEA (300 mg, 2.3 mmol) followed by HATU (733 mg, 1.9 mmol). The resulting solution was stirred at room temperature overnight. The reaction mixture was poured into water and extracted with ethyl acetate. The organic phase was washed with NH₄Cl solution, water and brine, dried over Na₂SO₄ and concentration in vacuo. The crude solid was purified by column chromatography eluted with ethyl acetate:dichloromethane=3:1 to give compound 9003 as a yellow solid (120 mg, 16%).

LCMS: m/z 619.2 [M+1]⁺. ¹H NMR (400 MHz, DMSO-d6): δ 0.90-1.09 (m, 2H), 1.38 (s, 9H), 1.52-1.63 (m, 3H), 2.66-2.69 (m, 4H), 3.90 (d, J=10.8 Hz, 2H), 7.40-7.47 (m, 1H), 7.58-7.60 (m, 1H), 7.68 (d, J=7.6 Hz, 1H), 7.75 (dd, J=8.8 Hz, 2.0 Hz, 1H), 7.84 (s, 2H), 7.90-7.92 (m, 3H), 8.01 (d, J=2.0 Hz, 1H), 8.65, 8.70 (2 doublet peaks, J=5.2 Hz, 1H), 10.87 (s, 1H).

Step 11d. 2-Chloro-N-(4-chloro-3-(pyridin-2-yl)phenyl)-4-(N-(piperidin-4-ylmethyl)sulfamoyl)benzamide (Compound 9004)

To the solution of 9003 (120 mg, 0.2 mmol) in dichloromethane (1 mL) was added TFA (1 mL). The mixture was stirred at room temperature for 1 h. The reaction solution was concentrated. The residue was dissolved with ethyl acetate and washed with NaHCO₃ solution. The ethyl acetate layer was dried over Na₂SO₄, filtered and concentrated in vacuo to give compound 9004 as a yellow solid (100 mg, 99% yield).

LCMS: m/z 519.2 [M+1]⁺. ¹H NMR (400 MHz, DMSO-d6): δ 1.10-1.15 (m, 2H), 1.57 (br, 1H), 1.69 (d, J=13.2 Hz, 2H), 2.60-2.69 (m, 4H), 3.10 (d, J=12.0 Hz, 2H), 7.43 (t, J=6.0 Hz, 1H), 7.59 (d, J=8.8 Hz, 1H), 7.69 (d, J=8.0 Hz, 1H), 7.75 (d, J=8.4 Hz, 1H), 7.85 (s, 2H), 7.91-7.94 (m, 2H), 8.01 (s, 1H), 8.71 (d, J=4.4 Hz, 1H), 10.88 (s, 1H).

Step 11e. Ethyl 2-(4-((3-chloro-4-(4-chloro-3-(pyridin-2-yl)phenylcarbamoyl)phenyl sulfonamido)methyl)piperidin-1-yl)pyrimidine-5-carboxylate (Compound 9005)

To the solution of 9004 (100 mg, 0.2 mmol) and Et₃N (0.2 mL, 1.4 mmol) in DCM (2 mL) was added 4005 (39 mg, 0.2 mmol). The resulting mixture was stirred at room temperature for 1 h. The reaction mixture was diluted with ethyl acetate and washed with 1N HCl. The ethyl acetate layer was dried over Na₂SO₄, filtered and concentrated to give compound 9005 as a yellow solid (135 mg, 96% yield). LCMS: m/z 669.3 [M+1]⁺. ¹H NMR (400 MHz, DMSO-d6): δ 1.10-1.18 (m, 2H), 1.29 (t, J=7.2 Hz, 3H), 1.76 (d, J=6.0 Hz, 2H), 2.68-2.72 (m, 2H), 2.94-3.00 (m, 2H), 4.27 (q, J=6.8 Hz, 2H), 4.72 (d, J=12.8 Hz, 2H), 7.45 (t, J=6.0 Hz, 1H), 7.59 (d, J=8.8 Hz, 1H), 7.70 (d, J=7.6 Hz, 1H), 7.75 (d, J=8.8 Hz, 1H), 7.86 (s, 2H), 7.92-8.01 (m, 3H), 8.71 (d, J=4.8 Hz, 1H), 8.77 (s, 2H), 9.28 (br, 1H), 10.89 (s, 1H).

Step 11f. 2-(4-((3-Chloro-4-(4-chloro-3-(pyridin-2-yl)phenylcarbamoyl) phenylsulfonamido)methyl) piperidin-1-yl)-N-hydroxypyrimidine-5-carboxamide (Compound 90)

Compound 9005 (135 mg, 0.2 mmol) was taken into NH₂OH methanolic solution (1.79M, 10 mL). The resulting mixture was stirred in sealed tube at room temperature for 3 h. TLC showed reaction complete. Acetic acid was added to adjust pH to 6~7 followed by the addition of ice-water. The reaction mixture was filtered, washed with water. The crude product was purified by prepared HPLC to afford compound 90 as a white solid (30 mg, 22% yield). M.p.: 172-173° C. LCMS: m/z 656.2 [M+1]⁺. ¹H NMR (400 MHz, DMSO-d6): δ 1.04-1.07 (m, 2H), 1.73-1.76 (m, 3H), 2.70-2.72 (m, 2H), 2.89-2.95 (m, 2H), 4.69 (d, J=12.8 Hz, 2H), 7.45 (t, J=6.0 Hz, 1H), 7.59 (d, J=8.8 Hz, 1H), 7.70 (d, J=8.0 Hz, 1H), 7.75 (d, J=8.4 Hz, 1H), 7.86 (s, 2H), 7.91-7.95 (m, 2H), 8.02 (s, 1H), 8.65 (s, 2H), 8.71 (d, J=4.4 Hz, 1H), 8.99 (br, 1H), 10.88 (s, 1H), 10.99 (br, 1H).

Example 12: 2-Chloro-N-(4-chloro-3-(pyridin-2-yl)phenyl)-4-(N-(2-(4-(hydroxycarbamoyl)phenoxy)ethyl)sulfamoyl)benzamide (Compound 266)

Step 12a. 2-Chloro-4-(N-(2-(4-(ethoxycarbonyl)phenoxy)ethyl)sulfamoyl)benzoic acid (Compound 1001)

To a mixture of ethyl 4-(2-aminoethoxy)benzoate (330 mg, 1.6 mmol) and 3003 (400 mg, 1.6 mmol) in dichloromethane (10 mL) was added triethylamine (0.6 mL, 4.4 mmol). The mixture was stirred at room temperature overnight. The reaction mixture was diluted with ethyl acetate and washed with 1N HCl. The ethyl acetate layer was concentrated in vacuo and purified by column chromatography (dichloromethane:MeOH=50:1) to give compound 1001 as a yellow solid (270 mg, 40% yield). LCMS: m/z 428.0 [M+1]⁺. ¹H NMR (400 MHz, DMSO-d6): δ 1.30 (t, J=7.2 Hz, 3H), 3.20-3.22 (m, 2H), 4.04 (t, J=4.8 Hz, 2H), 4.27 (q, J=7.2 Hz, 2H), 6.93 (d, J=8.8 Hz, 2H), 7.66 (d, J=8.4 Hz, 1H), 7.71 (d, J=8.0 Hz, 1H), 7.77 (s, 1H), 7.87 (d, J=8.4 Hz, 2H), 8.12 (br, 1H).

Step 12b. Ethyl 4-(2-(3-chloro-4-(4-chloro-3-(pyridin-2-yl)phenylcarbamoyl)phenyl sulfonamido)ethoxy)benzoate (Compound 1002)

To a mixture of compound 1001 (270 mg, 0.6 mmol) and 1-8 (108 mg, 0.5 mmol) in DMF (2.0 mL) was added DIPEA (164 mg, 1.3 mmol) followed by HATU (289 mg, 0.8 mmol). The resulting solution was stirred overnight at room temperature. The reaction mixture was poured into water and extracted with ethyl acetate. The organic phase was washed with 1N HCl solution, water, brine and dried over Na₂SO₄. The crude solid was purified by column chromatography eluted with dichloromethane/MeOH=100/1 to give compound 1002 as a yellow solid (130 mg, 33%). LCMS: m/z 614.2 [M+1]⁺. ¹H NMR (400 MHz, DMSO-d6): δ 1.28 (t, J=6.8 Hz, 3H), 3.24-3.26 (m, 2H), 4.06-4.09 (m, 2H), 4.25 (q, J=6.8 Hz, 2H), 6.89 (d, J=8.4 Hz, 2H), 7.43-7.47 (m, 1H), 7.59 (d, J=8.8 Hz, 1H), 7.70 (d, J=7.6 Hz, 1H), 7.80-7.95 (m, 7H), 8.01 (s, 1H), 8.24-8.27 (m, 1H), 8.70-8.72 (d, J=4.0 Hz, 1H), 10.86 (s, 1H).

Step 12c. 2-Chloro-N-(4-chloro-3-(pyridin-2-yl)phenyl)-4-(N-(2-(4-(hydroxycarbamoyl)phenoxy)ethyl)sulfamoyl)benzamide (Compound 266)

Compound 1002 (130 mg, 0.2 mmol) was taken into NH$_2$OH methanolic solution (1.79M, 10 mL). The resulting mixture was stirred in sealed tube at room temperature for 3 h. TLC showed reaction complete. 1N HCl was added to adjust pH to 6~7 followed by the addition of ice-water. The reaction mixture was filtered, washed with water. The crude product was purified by prep-HPLC to afford compound 266 as a yellow solid (41 mg, 32% yield). mp: 138-139° C. LCMS: m/z 601.2 [M+1]$^+$. $^1$H NMR (400 MHz, DMSO-d6): δ 3.23 (t, J=4.0 Hz, 2H), 4.06 (t, J=4.8 Hz, 2H), 6.92 (d, J=8.4 Hz, 2H), 7.45 (t, J=6.4 Hz, 1H), 7.58 (d, J=8.8 Hz, 1H), 7.68-7.76 (m, 4H), 7.86-7.96 (m, 4H), 8.02 (s, 1H), 8.19 (d, J=4.0 Hz, 1H), 8.71 (d, J=4.4 Hz, 1H), 8.89 (br, 1H), 10.88 (s, 1H), 11.05 (s, 1H).

Example 13: 2-(4-((5-(3-(1H-Benzo[d]imidazol-2-yl)-4-chlorophenylcarbamoyl)-6-methylpyridin-2-ylamino)methyl)piperidin-1-yl)-N-hydroxypyrimidine-5-carboxamide (Compound 91)

Step 13a. 6-Bromo-2-methylnicotinaldehyde (Compound 1102)

To a stirred solution of 3,6-dibromo-2-methylpyridine (2.0 g, 8.0 mmol) in dry THF (20 mL) was added n-BuLi (1.6M, 6.0 mL) dropwise at −78° C. When the addition was complete the reaction was continued for 1 h. Dichloromethane (642.4 mg, 8.8 mmol) was added at −78° C. and continued to stir for 1 h. The reaction was allowed to warm to room temperature followed by addition of HCl (1M, 10 mL). The mixture was extracted with ethyl acetate. The organic layer was washed with brine and concentrated. The crude product was purified by column chromatography eluted with dichloromethane/methanol (30:1) to afford compound 1102 as a white solid (1.4 g, 90%).

Step 13b. 6-Bromo-2-methylnicotinic acid (Compound 1103)

To a stirred solution of compound 1102 (1.4 g, 6.7 mmol) in acetone (20 mL) was added Jones reagent (2.67M, 5.2 ml) at 0° C. The reaction mixture was warmed to room temperature and stirred for 30 min. Saturated NaHCO$_3$ solution was added to adjust pH=5-6. The mixture was extracted with ethyl acetate. The organic layer was washed with brine and concentrated. The crude product was purified by column chromatography eluted with ethyl acetate/hexanes (1:8) to afford compound 1103 as a white solid (1.0 g, 66%). $^1$H NMR (400 MHz, CDCl$_3$): δ 2.87 (s, 3H), 7.46 (d, J=8.4 Hz, 1H), 8.15 (d, J=8.4 Hz, 1H).

Step 13c. N-(3-(1H-benzo[d]imidazol-2-yl)-4-chlorophenyl)-6-bromo-2-methylnicotinamide (Compound 1104)

Compound 1103 (1.0 g, 4.6 mmol) was added to a mixture of compound 2-3 (1.2 g, 4.6 mmol), HATU (3.5 g, 5.5 mmol) and Et$_3$N (19 mL, 13.8 mmol) in dichloromethane (30 mL). The reaction mixture was stirred at room temperature overnight. The mixture was quenched with water, extracted with dichloromethane, concentrated. The crude product was purified by column chromatography eluted with hexanes/ethyl acetate (1:1) to afford compound 1104 as a white solid (1.0 g, 50%). LCMS: m/z 443.1[M+1]$^+$.

Step 13d. tert-Butyl 4-((5-(3-(1H-benzo[d]imidazol-2-yl)-4-chlorophenylcarbamoyl)-6-methyl pyridin-2-ylamino)methyl)piperidine-1-carboxylate (Compound 1105)

To a stirred solution of compound 1104 (500 mg, 1.13 mmol) in i-PiOH (10 mL) was added tert-butyl 4-(aminomethyl)piperidine-1-carboxylate (930 mg, 4.4 mmol) and K$_2$CO$_3$ (1.2 g, 8.7 mmol). The mixture was stirring under 100° C. for 48 h. The mixture was quenched with water and extracted with dichloromethane. The crude product was purified by column chromatography eluted with hexane/ethyl acetate (1:1) to afford compound 1105 as a yellow solid (250 mg, 38% yield). LCMS: m/z 575.4[M+1]$^{+1}$H NMR (400 MHz, DMSO-d6): δ 1.06-1.12 (m, 2H), 1.45 (s, 9H), 1.73-1.76 (m, 3H), 2.50 (s, 3H), 2.73-2.75 (m, 2H), 3.25 (s, 2H), 3.98-4.02 (m, 2H), 6.43 (d, J=8.8 Hz, 1H), 7.02-7.05 (m, 1H), 7.25-7.34 (m, 2H), 7.63-7.66 (m, 3H), 7.76 (d, J=7.6 Hz, 1H), 7.92 (d, J=8.8 Hz, 2H), 8.41 (s, 1H), 10.28 (s, 1H), 12.72 (s, 1H).

Step 13e. Methyl 2-(4-((5-(3-(1H-benzo[d]imidazol-2-yl)-4-chlorophenylcarbamoyl)-6-methyl pyridin-2-ylamino)methyl)piperidin-1-yl)pyrimidine-5-carboxylate (Compound 1106)

To a stirred solution of compound 1105 (70 mg, 0.12 mmol) in dichloromethane was added TFA (3 mL). The mixture was stirred for 30 min. The reaction solution was concentrated and the residue was dissolved in dichloromethane (10 mL). To the solution was added 4005 (31 mg, 0.14 mmol) and Et$_3$N (1 mL). The resulting mixture was stirred at room temperature for 30 min and concentrated. The residue was purified by column chromatography eluted with hexanes/ethyl acetate (1:1) to afford compound 1106 as a yellow solid (70 mg, 94%). LCMS: m/z 611.3 [M+1]$^{+1}$H NMR (400 MHz, DMSO-d6): δ 1.08-1.14 (m, 2H), 1.72-2.02 (m, 4H), 2.45 (s, 3H), 2.94-3.05 (m, 3H), 3.80 (s, 3H), 4.77 (d, J=13.2 Hz, 2H), 6.39 (d, J=8.8 Hz, 1H), 7.03 (d, J=5.2 Hz, 1H), 7.23-7.27 (m, 2H), 7.58-7.60 (m, 2H), 7.71 (d, J=7.2 Hz, 1H), 7.87 (d, J=7.6 Hz, 2H), 8.35 (s, 1H), 8.77 (s, 2H), 10.23 (s, 1H), 12.69 (s, 1H).

Step 13f. 2-(4-((5-(3-(1H-Benzo[d]imidazol-2-yl)-4-chlorophenylcarbamoyl)-6-methylpyridin-2-ylamino)methyl)piperidin-1-yl)-N-hydroxypyrimidine-5-carboxamide (Compound 91)

Compound 1106 (70 mg, 0.11 mmol) was taken into NH$_2$OH methanolic solution (10 mL, 1.79 M). The mixture was stirred at room temperature for 40 min. The reaction mixture was adjusted pH to 8-9 with acetic acid and concentrated. The residue was purified by HPLC to afford the titled compound 91 as a white solid (37 mg, 53%).

M.p.: 194-196° C. LCMS: m/z 612.3[M+1]$^{+1}$H NMR (400 MHz, DMSO-d6): δ 1.13-1.18 (m, 2H), 1.78-2.00 (m, 3H), 2.45 (s, 3H), 2.91-2.98 (m, 2H), 3.22 (s, 2H), 4.73 (d, J=12.4 Hz, 2H), 6.38 (d, J=8.4 Hz, 1H), 7.00-7.02 (m, 1H), 7.24-7.26 (m, 2H), 7.57-7.60 (m, 3H), 7.69-7.71 (d, J=7.2 Hz, 1H), 7.86 (d, J=8.8 Hz, 1H), 8.35 (s, 1H), 8.65 (s, 2H), 8.97 (br, 1H), 10.23 (s, 1H), 10.98 (br, 1H), 12.68 (s, 1H).

Example 14: 2-(3-(4-Chloro-3-(5-(dimethylamino)-1H-benzo[d]imidazol-2-yl)phenylcarbamoyl)-5-methoxybenzylamino)-N-hydroxypyrimidine-5-carboxamide (Compound 258)

Step 14a. Methyl 3-(hydroxymethyl)-5-methoxybenzoate (Compound 1202)

To a stirred solution of dimethyl 5-methoxyisophthalate (1.0 g, 4.5 mmol) in THF (10 mL) was added DIBAL-H (6.6 mL, 6.6 mmol). The reaction mixture was stirred for overnight at room temperature. The reaction mixture was diluted with ethyl acetate and washed with water and brine. The organic phase was dried over $Na_2SO_4$ and concentrated. The crude product was purified by column chromatography eluted with hexanes/EA (2:1) to afford compound 1202 as a yellow solid (600 mg, 68% yield).

LCMS: m/z 197.1[M+1]$^+$. $^1$H NMR (400 MHz, DMSO-$d_6$): δ 3.80 (s, 3H), 3.85 (s, 3H), 4.53 (d, J=6.0 Hz, 2H), 5.35 (t, J=5.8 Hz, 1H), 7.15 (s, 1H), 7.31 (s, 1H), 7.54 (s, 1H).

Step 14b. Methyl 3-(bromomethyl)-5-methoxybenzoate (Compound 1203)

To a stirred solution of compound 1202 (800 mg, 4.0 mmol) in dichloromethane (10 mL) was added $PBr_3$ (0.4 mL, 4.3 mmol). The reaction mixture was stirred for 1 h at room temperature. The reaction was diluted with ethyl acetate and washed with water and brine. The organic phase was dried over $Na_2SO_4$ and concentrated. The crude product was purified by column chromatography eluted with hexanes/ethyl acetate (5:1) to obtain compound 1203 as a yellow oil. (640 mg, 61% yield). $^1$H NMR (400 MHz, $CDCl_3$): δ 3.85 (s, 3H), 3.92 (s, 3H), 7.12 (br, 1H), 7.49 (br, 1H), 7.65 (br, 1H).

Step 14c. Methyl 3-(azidomethyl)-5-methoxybenzoate (Compound 1204)

To a stirred solution of compound 1203 (640 mg, 2.5 mmol) in DMF (5 mL) was added $NaN_3$ (1.1 g 16.9 mmol). The reaction mixture was stirred at room temperature for 2 h. The reaction solution was diluted with ethyl acetate and washed with water and brine. The organic phase was dried over $Na_2SO_4$ and concentrated. The crude product was purified by column chromatography eluted with hexanes/ethyl acetate (5:1) to afford compound 1204 as a yellow oil (500 mg, 91% yield). LCMS: m/z 263.2[M+1+41]$^+$.

Step 14d. Methyl 3-(aminomethyl)-5-methoxybenzoate (Compound 1205)

To a stirred solution of compound 1204 (500 mg, 2.3 mmol) in THF (10 mL) was added $PPh_3$ (650 mg, 2.5 mmol) and stirred for 30 min. Water (100 mg, 5.5 mmol) was added. The mixture was warmed to 60° C. and stirred for 2 h. The reaction mixture was diluted with ethyl acetate and washed with water and brine. The organic phase was dried over $Na_2SO_4$ and concentrated. The crude product was purified by column chromatography eluted with dichloromethane/MeOH (50:1) to afford compound 1205 as a yellow oil (300 mg, 68% yield). LCMS: m/z 196.1[M+1]$^+$.

Step 14e. 3-(Aminomethyl)-5-methoxybenzoic acid (Compound 1206)

Compound 1205 (300 mg, 1.5 mmol) was added to a mixture of LiOH (180 mg, 7.5 mmol) in EtOH (2 mL) and $H_2O$ (2 mL). The reaction mixture was stirred at room temperature for 3 h. The reaction mixture was adjusted pH to 6 with 2N HCl. The mixture was concentrated and directly used to next step without further purification.

Step 14f. 3-Methoxy-5-((5-(methoxycarbonyl)pyrimidin-2-ylamino)methyl)benzoic acid (Compound 1207)

To a stirred solution of 1206 (200 mg, 1.0 mmol) and $Et_3N$ (300 mg, 3.0 mmol) in dichloromethane (5 mL) was added 4005 (176 mg, 1.0 mmol). The reaction mixture was stirred at room temperature for 1 h. The reaction solution was diluted with ethyl acetate and washed with water and brine. The organic phase was dried over $Na_2SO_4$, then concentrated. The crude product was purified by column chromatography eluted with dichloromethane/MeOH (50:1) to afford compound 1207 as a yellow solid (110 mg, 31% yield). LCMS: m/z 318.2[M+1]$^+$. $^1$H NMR (400 MHz, DMSO-$d_6$): δ 3.78 (s, 3H), 3.79 (s, 3H), 4.60 (d, J=6.4 Hz, 2H), 7.13 (s, 1H), 7.31 (s, 1H), 7.49 (s, 1H), 8.67 (t, J=6.0 Hz, 1H), 8.75 (s, 2H).

Step 14 g. Methyl 2-(3-(4-chloro-3-(5-(dimethylamino)-1H-benzo[d]imidazol-2-yl)phenyl carbamoyl)-5-methoxybenzylamino)pyrimidine-5-carboxylate (Compound 1208)

To a stirred solution of compound 1207 (110 mg, 0.3 mmol), 2-3 (90 mg, 0.3 mmol) and DIPEA (90 mg, 0.7 mmol) in DMF was added HATU (160 mg, 0.4 mmol). The reaction mixture was stirred at room temperature overnight. The reaction mixture was diluted with ethyl acetate and washed with water and brine. The organic phase was dried over $Na_2SO_4$ and concentrated. The crude product was purified by column chromatography eluted with hexanes/ethyl acetate (1:1) to afford compound 1208 as a yellow solid (60 mg, 30% yield). LCMS: m/z 586.3[M+1]$^+$.

Step 14 h. 2-(3-(4-Chloro-3-(5-(dimethylamino)-1H-benzo[d]imidazol-2-yl)phenylcarbamoyl)-5-methoxybenzylamino)-N-hydroxypyrimidine-5-carboxamide (Compound 258)

Compound 1208 (70 mg, 0.1 mmol) was taken into $NH_2OH$ methanolic solution (10 mL, 1.79 M). The mixture was stirred at room temperature for 40 min. The reaction mixture was adjusted pH to 8-9 with acetic acid and concentrated. The residue was purified by prep-HPLC to afford the titled compound 258 as a yellow solid (35 mg, 50%). M.p.: 158-159° C. LCMS: m/z 587.3[M+1]$^+$. $^1$H NMR (400 MHz, DMSO-d6): δ 2.93 (s, 6H), 3.82 (s, 3H), 4.60 (d, J=6.0 Hz, 2H), 6.78-6.97 (m, 2H), 7.10 (s, 1H), 7.41 (s, 1H), 7.49-7.52 (m, 2H), 7.58 (d, J=8.8 Hz, 1H), 7.94 (dd, J=8.8, 2.8 Hz, 1H), 8.30 (t, J=6.2 Hz, 1H), 8.37 (br, 1H), 8.61 (s, 2H), 8.94 (br, 1H), 10.42 (s, 1H), 10.98 (br, 1H), 12.17, 12.30 (two single peaks, 1H).

Example 15: 2-((3-(4-Chloro-3-(5-(dimethylamino)-1H-benzo[d]imidazol-2-yl)phenylcarbamoyl)-5-methoxybenzyl)(methyl)amino)-N-hydroxypyrimidine-5-carboxamide (Compound 259)

Step 15a. Methyl 3-methoxy-5-((methylamino)methyl)benzoate (Compound 1301)

To a solution of 1203 (150 mg, 0.6 mmol) in DMF (3 mL) was added methylamine methanol solution (2.5 mL). The reaction mixture was stirred at room temperature for 10 min. Water (10 mL) was added to the reaction mixture and the resulting reaction mixture was extracted with ethyl acetate (10 mL×2). The combined organic layers were washed with water. The organic phase was dried over $Na_2SO_4$, filtered and evaporated to give product 1301 as light yellow oil (100 mg, 83%). LCMS: m/z 210.1 [M+1]$^+$. $^1$H NMR (400 MHz, CDCl$_3$): δ 2.45 (s, 3H), 3.77 (s, 2H), 3.85 (s, 3H), 3.92 (s, 3H), 7.10 (s, 1H), 7.45 (s, 1H), 7.59 (s, 1H).

Step 15b. Methyl 3-((tert-butoxycarbonyl(methyl)amino)methyl)-5-methoxybenzoate (Compound 1302)

(Boc)$_2$O (154 mg, 0.7 mmol), NEt$_3$ (101 mg, 1.0 mmol) and DMAP (6 mg, 0.05 mmol) were added to a solution of compound 1301 (100 mg, 0.5 mmol) in anhydrous dichloromethane (10 mL). The reaction mixture was stirred at room temperature for 2 h until TLC indicated that compound 1301 had been consumed. The reaction mixture was concentrated and the residue was purified by column chromatography eluted with CH$_2$Cl$_2$: MeOH (10:1) to afford the titled compound 1302 as light yellow oil (110 mg, 75%).

Step 15c. 3-((tert-Butoxycarbonyl(methyl)amino)methyl)-5-methoxybenzoic acid (Compound 1303)

NaOH aqueous solution (4.0M, 10 mL) was added to a solution of compound 1302 (160 mg, 0.5 mmol) in methanol (5 mL). The solution was stirred at room temperature for 2 h. The reaction mixture was acidified to pH 3~4 with conc. HCl solution and extracted with ethyl acetate (10 mL×2) and dried over Na$_2$SO$_4$. The title compound 1303 was obtained as a yellow solid after concentration (100 mg, 66%). $^1$H NMR (400 MHz, CDCl$_3$): δ 1.42 (s, 9H), 2.78 (s, 3H), 3.78 (s, 3H), 4.37 (s, 2H), 6.96 (s, 1H), 7.44 (s, 1H), 7.50 (s, 1H).

Step 15d. tert-Butyl 3-(4-chloro-3-(5-(dimethylamino)-1H-benzo[d]imidazol-2-yl) phenylcarbamoyl)-5-methoxybenzyl(methyl)carbamate (Compound 1304)

Compound 2-3 (97 mg, 0.3 mmol) was added to a solution of compound 1303 (100 mg, 0.3 mmol), HATU (137 mg, 0.4 mmol) and DIPEA (78 mg, 0.6 mmol) in DMF (4 mL). The reaction mixture was stirred at room temperature overnight. The mixture was diluted with water (10 mL) and extracted with ethyl acetate (10 mL×2). The organic layer was washed with water and dried over Na$_2$SO$_4$. The titled compound 1304 was obtained as yellow solid after concentration (150 mg, 89%). LCMS: m/z 564.3 [M+1]$^+$.

Step 15e. N-(4-Chloro-3-(5-(dimethylamino)-1H-benzo[d]imidazol-2-yl)phenyl)-3-methoxy-5-((methylamino)methyl)benzamide (Compound 1305)

Compound 1304 (150 mg) was dissolved in trifluoroacetic acid (10 mL). The reaction mixture was stirred at room temperature for 1 h. The reaction was then concentrated to remove most trifluoroacetic acid. The residue was adjusted to pH 7~8 with saturated aqueous NaHCO$_3$ solution and extracted with ethyl acetate. The organic layer was washed with brine and dried over Na$_2$SO$_4$ and concentrated. The crude product was purified by column chromatography eluted with CH$_2$Cl$_2$: MeOH (20:1) to afford the titled compound 1305 as a light yellow solid (50 mg, 40%). $^1$H NMR (400 MHz, CDCl$_3$): δ 2.69 (s, 3H), 3.00 (s, 6H), 3.76 (s, 3H), 3.91 (s, 2H), 6.85 (s, 2H), 6.90 (dd, J=9.2 Hz, 2.4 Hz, 1H), 7.33~7.38 (m, 2H), 7.52 (d, J=8.8 Hz, 1H), 7.58 (s, 1H), 8.06~8.11 (m, 2H), 9.03 (br, 1H).

Step 15f. Ethyl 2-((3-(4-chloro-3-(5-(dimethylamino)-1H-benzo[d]imidazol-2-yl)phenylcarbamoyl)-5-methoxybenzyl)(methyl)amino)pyrimidine-5-carboxylate (Compound 1306)

To a solution of compound 1305 (50 mg, 0.1 mmol) in dichloromethane was added compound 4005 (19 mg, 0.1 mmol) and NEt$_3$ (30 mg, 0.3 mmol). The reaction mixture was stirred at room temperature for 2 h. The reaction mixture was washed with water and concentrated to afford the title compound 1306 (90 mg). LCMS: 614.3 [M+1]$^+$. $^1$H NMR (400 MHz, CDCl$_3$): δ 1.36 (t, J=7.2 Hz, 3H), 3.00 (s, 6H), 3.24 (s, 3H), 3.85 (s, 3H), 4.34 (q, J=7.2 Hz, 2H), 4.99 (s, 2H), 6.87~6.92 (m, 2H), 6.98 (s, 1H), 7.32 (s, 2H), 7.47 (d, J=9.2 Hz, 1H), 7.57 (d, J=8.8 Hz, 1H), 8.23~8.24 (m, 3H), 8.90 (s, 2H).

Step 15 g. 2-((3-(4-Chloro-3-(5-(dimethylamino)-1H-benzo[d]imidazol-2-yl)phenylcarbamoyl)-5-methoxybenzyl)(methyl)amino)-N-hydroxypyrimidine-5-carboxamide (Compound 259)

Compound 1306 (90 mg, 0.1 mmol) was dissolved in NH$_2$OH methanol solution (20 mL, 1.79M). The mixture was stirred at room temperature for 1 h. The reaction mixture was adjusted pH to 8-9 with 2N HCl and evaporated in vacuo. The residue was triturated with water to afford the crude product. The crude product was further purified by prep-HPLC to afford compound 259 as a yellow solid (18 mg, 20%). M.p.: 207~208° C. LCMS: m/z 601.3 [M+1]$^+$. $^1$H NMR (400 MHz, DMSO-d6): δ 2.93 (s, 6H), 3.18 (s, 3H), 3.82 (s, 3H), 4.96 (s, 2H), 6.78~6.88 (m, 2H), 7.00 (s, 1H), 7.41~7.51 (m, 3H), 7.57 (d, J=8.4 Hz, 1H), 7.94 (d, J=8.4 Hz, 1H), 8.14 (s, 1H), 8.37 (s, 1H), 8.71 (s, 2H), 8.98 (br, 1H), 10.42 (s, 1H), 11.03 (s, 1H), 12.15 (s, 1H).

Example 16: An In Vitro Assay which Determines the Ability of a Test Compound to Inhibit HDAC Enzymatic Activity HDAC inhibitory activity was assessed using the Biomol Color de Lys system (AK-500, Biomol, Plymouth Meeting, Pa.). Briefly, HeLa cell nuclear extracts were used as a source of HDACs. Different concentrations of test compounds were serially diluted in dimethylsulfoxide (DMSO) and added to HeLa cell nuclear extracts in the presence of a colorimetric artificial substrate. Final assay conditions contained 50 mM Tris/Cl, pH 8.0, 137 mM NaCl, 2.7 mM KCl and 1 mM MgCl$_2$. Reactions were carried out at room temperature (25° C.) for 1 hour before addition of developer for termination. Relative enzyme activity was measured in the WALLAC Victor II 1420 microplate reader as fluorescence intensity (excitation: 350-380 nm; emission: 440-460

Example 17: An In Vitro Assay which Determines the Ability of a Test Compound to Inhibit Hedgehog Signalling Compounds to be tested were dissolved in DMSO to a concentration of 10 mM, and stored at −20° C. To activate the Hedgehog pathway in the assay cells, an octylated (lipid-modified) form of the N-terminal fragment of the Sonic Hedgehog protein (OCT-SHH) was used. This N-terminal SHH fragment is produced bacterially. See, for example, Taylor F R, et al., Biochemistry, 2001, 40: 4359-71.

Compounds were tested in the "Gli-Luc" assay below, using the cell line 10 T1/2 (s12), wherein the cells contain a Hedgehog-responsive reporter construct utilizing Luciferase as the reporter gene. In this way, Hedgehog pathway signaling activity is measured via the Gli-Luc response.

10 T1/2 (s12) cells were plated in a 96-well micro-titer plate (MTP) at 20,000 cells/well in full medium [DMEM with 10% FBS]. Then plates were placed in the incubator for incubation overnight (O/N), at 37° C. and 5% $CO_2$. After 24 h, the medium was replaced with Luciferase-assay medium (DMEM with 0.5% FBS). Test compounds were thawed and diluted in assay medium at 3:1000 (about 300-fold) resulting in a starting concentration of about 0.0003 uM to 30 uM. Subsequently, 150 ul of each sample was added to the first wells (in triplicate). The MTP samples were then diluted at 3-fold dilutions to a total of seven wells, ultimately resulting in a regiment of seven dilutions in triplicate, for each compound. Next, the protein ligand OCT-SHH was diluted in Luciferase-assay medium and added to each well at a final concentration of 0.3 μg/ml. Plates were then returned to the incubator for further incubation O/N, at 37° C. and 5% $CO_2$. After about 24 h, plates were removed from the incubator and the medium was aspirated/discarded.

Wells were washed once with assay buffer [PBS+1 mM $Mg^{2+}$ and 1 mM $Ca^{2+}$]. Then 50 μl of assay buffer was added to each well. The Luciferase assay reagent was prepared as described by the vendor (LucLite kit from Packard), and 50 μl was added to each well. Plates were incubated at room temperature (RT) for about 30 minutes after which the signals were read, again at RT, on a Topcount (Packard).

Similar assays were performed using human cell lines (specifically, human embryonic palatal mesenchyme cells, modified with the Gli-Luc construct as described above) in a growth medium of MEM/Sodium Pyruvate w/10% FBS, and an assay medium of MEM/Sodium Pyruvate w/0.5% FBS. OCT-SHH was added to reach a final concentration of 1 μg/ml.

Results of the HDAC inhibition and hedgehog inhibition assays described in Examples 16 and 17, respectively, are set forth in the table below, which indicates the IC50 determined in each assay as follows: I>1000 nM; 1000 nM≥II>100 nM; 100 nM≥III>10 nM; 10 nM≥IV>1 nM; 1 nM≥V.

| Compound No. | HDAC | Hh Reporter assay |
|---|---|---|
| 1 | II | II |
| 5 | II | II |
| 7 | II | I |
| 23 | III | II |
| 59 | II | III |
| 86 | III | III |
| 90 | III | IV |
| 91 | III | III |
| 111 | III | II |
| 254 | II | III |
| 258 | III | III |
| 259 | III | III |
| 263 | III | II |
| 265 | I | |
| 266 | II | IV |
| SAHA | ~40 nM | 477 nM |
| Compound A | | 17/24/13.1 nM |
| LBH 589 | 7 nM | |

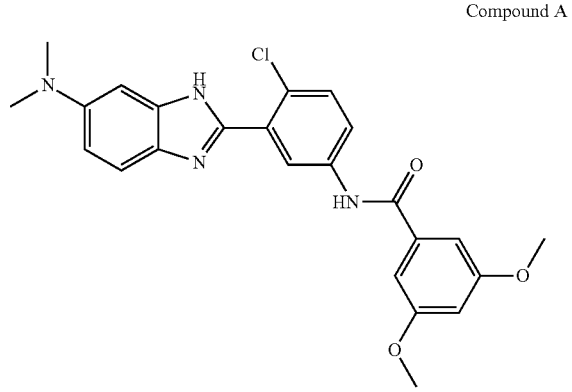

Compound A

Example 18. An In Vitro Assay which Determines the Ability of a Test Compound to Inhibit Binding of Hedgehog to Smoothened Smo is transiently overexpressed in 293T cells, the membranes are harvested and a filtration membrane-competition-binding assay is performed in a 96-well plate with [$^3$H]-Hh-Ag 1.5 added at 2 nM. Membranes are prepared as follows. Briefly, approximately $10^8$ cells are transfected with pCMV6-XL5 constructs bearing human Smoothened (OriGene) using Fugene 6 (Roche). After 48 hours cells are harvested by scraping in PBS, centrifuged at 1,000×g for 10 minutes, and gently resuspended in around 10 ml of a 50 mM Tris pH 7.5, 250 mM sucrose buffer containing an EDTA-free protease inhibitor cocktail (Roche). This cell suspension is then placed in a nitrogen cavitation device (Parr Instrument Co, Moline, USA) and exposed to nitrogen gas (230 psi) for 10 minutes. Lysed cells are released from the device and centrifuged at 20,000 rpm in an SS34 rotor for 20 minutes at 4° C. Supernatants are discarded and the pellets are resuspended in 10% sucrose, 50 mM Tris pH 7.5, 5 mM $MgCl_2$, 1 mM EDTA solution using three 10-second pulses with a Polytron (Brinkman; Westbury, USA) at a power setting of 12. Using these membranes, filtration binding assays are performed according to standard protocols. Briefly, a test compound is incubated for 1 hour at room temperature in the following binding buffer (50 mm Tris 7.5, 5 mM $MgCl_2$, 1 mM EDTA, 0.1% BSA) containing cell membrane lysate, [$^3$H]-Hh-Ag 1.5 and protease inhibitors. After incubation, the reaction is transferred to a 96-well filter plate, vacuum is applied to pull down the reaction buffer, the wells are washed twice and scintillation solution is added.

The reactions are read on a Top Count microplate reader to determine the fraction of [³H]-Hh-Ag 1.5 bound to the smoothened containing membrane preparation.

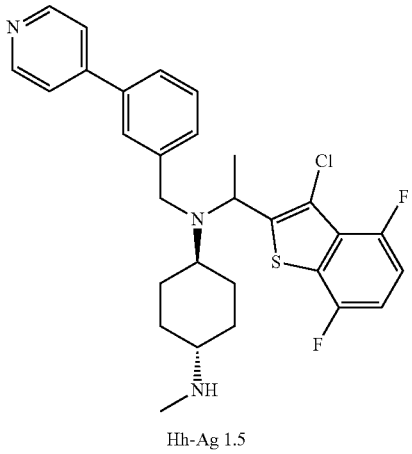 [SMILES: CN[C@H]1CC[C@H](N(Cc2cccc(-c3ccncc3)c2)C(C)c2sc3c(F)ccc(F)c3c2Cl)CC1]

Hh-Ag 1.5

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound of Formula (VI):

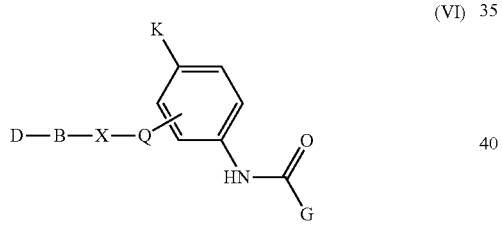

(VI)

or a pharmaceutically acceptable salt or prodrug thereof; wherein

Q is substituted or unsubstituted aryl or substituted or unsubstituted heteroaryl;

G is substituted or unsubstituted aryl or substituted or unsubstituted heteroaryl;

K is halogen;

X is absent, —O—, —N(R$_2$)—, —S—, —S(O)—, —S(O)$_2$—, —C(O)—, —C(O)O—, —OC(O)—, —C(O)N(R$_2$)—, —N(R$_2$)C(O)—, —S(O)$_2$N(R$_2$)—, or —N(R$_2$)S(O)$_2$—;

R$_2$ is hydrogen or C$_1$-C$_6$-alkyl;

B is a direct bond, straight chain C$_1$-C$_{10}$ alkyl, C$_1$-C$_{10}$ alkenyl, C$_1$-C$_{10}$ alkynyl, C$_1$-C$_{10}$ alkoxy, alkoxyC$_1$-C$_{10}$alkoxy, C$_1$-C$_{10}$ alkylamino, alkoxyC$_1$-C$_{10}$alkylamino, C$_1$-C$_{10}$ alkylcarbonylamino, C$_1$-C$_{10}$ alkylaminocarbonyl, aryloxyC$_1$-C$_{10}$alkoxy, aryloxyC$_1$-C$_{10}$alkylamino, aryloxyC$_1$-C$_{10}$alkylamino carbonyl, C$_1$-C$_{10}$-alkylaminoalkylaminocarbonyl, C$_1$-C$_{10}$ alkyl (N-alkyl)aminoalkyl-aminocarbonyl, alkylaminoalkylamino, alkylcarbonylaminoalkylamino, alkyl(N-alkyl)aminoalkylamino, (N-alkyl) alkylcarbonylaminoalkylamino, alkylaminoalkyl, alkylaminoalkylaminoalkyl, alkylpiperazinoalkyl, piperazinoalkyl, alkylpiperazino, alkenylaryloxyC$_1$-C$_{10}$alkoxy, alkenylarylaminoC$_1$-C$_{10}$alkoxy, alkenylaryllalkylaminoC$_1$-C$_{10}$alkoxy, alkenylaryloxyC$_1$-C$_{10}$alkylamino, alkenylaryloxyC$_1$-C$_{10}$alkylaminocarbonyl, piperazinoalkylaryl, heteroarylC$_1$-C$_{10}$alkyl, heteroarylC$_2$-C$_{10}$alkenyl, heteroarylC$_2$-C$_{10}$alkynyl, heteroarylC$_1$-C$_{10}$alkylamino, heteroarylC$_1$-C$_{10}$alkoxy, heteroaryloxyC$_1$-C$_{10}$alkyl, heteroaryloxyC$_2$-C$_{10}$alkenyl, heteroaryloxyC$_2$-C$_{10}$alkynyl, heteroaryloxyC$_1$-C$_{10}$alkylamino and heteroaryloxyC$_1$-C$_{10}$alkoxy, in each of which one or more methylenes is optionally interrupted or terminated by —O—, —N(R$_2$)—, —C(O)—, —C(O)N(R$_2$)—, or —C(O)O—; and D is

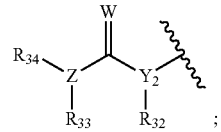

where Y$_2$ and R$_{32}$ are absent, Z is N, W is O, R$_{33}$ is H and R$_{34}$ is hydroxyl.

2. The compound of claim 1 represented by Formula XII:

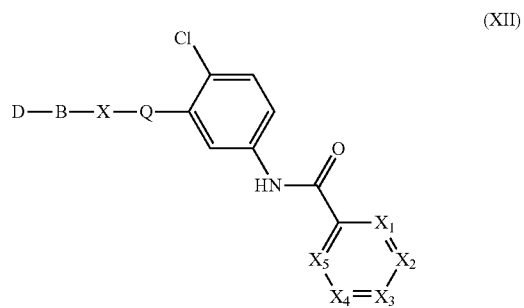

(XII)

or a pharmaceutically acceptable salt or prodrug thereof; wherein

X$_1$-X$_5$ are each independently selected from N and CR$_3$, provided that at least 2 of X$_1$-X$_5$ are CR$_3$;

each R$_3$ is independently selected from hydrogen, hydroxy, amino, halogen, alkoxy, alkylamino, dialkylamino, CF$_3$, CN, NO$_2$, sulfonyl, acyl, aliphatic, substituted aliphatic, aryl, substituted aryl, heteroaryl, substituted heteroaryl, heterocyclic, and substituted heterocyclic; and Q, D, B and X have the meanings given for these variables in claim 1.

3. The compound of claim 2, wherein Q is substituted or unsubstituted pyridyl, substituted or unsubstituted pyrimidyl or substituted or unsubstituted benzimidazolyl.

4. The compound of claim 3, wherein Q is selected from the groups below:

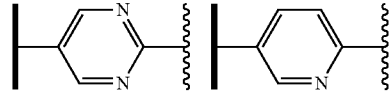

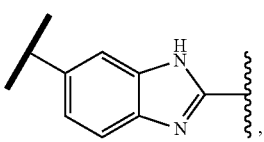

wherein the bond the benzene ring is denoted by §, and the bond to X is denoted by |.

5. The compound of claim 2, wherein:

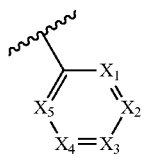

is substituted or unsubstituted phenyl, substituted or unsubstituted pyridyl, or substituted or unsubstituted pyrimidyl.

6. The compound of claim 5, wherein:

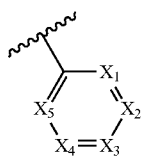

is selected from the group consisting of

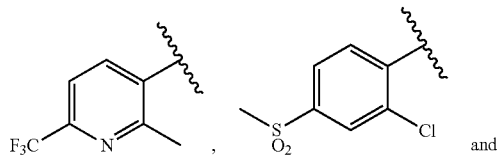

and

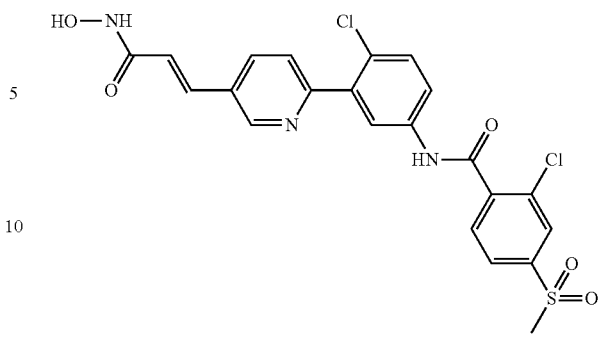

7. A pharmaceutical composition comprising a compound of claim 1 and a pharmaceutically acceptable carrier.

8. The compound of claim 1, selected from the compounds set forth in the table below, wherein n is 0 to 6, or a pharmaceutically acceptable salt thereof:

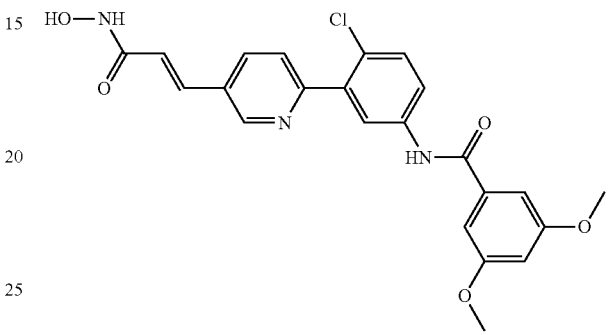

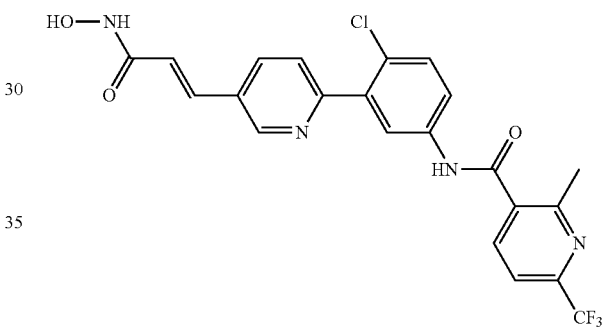

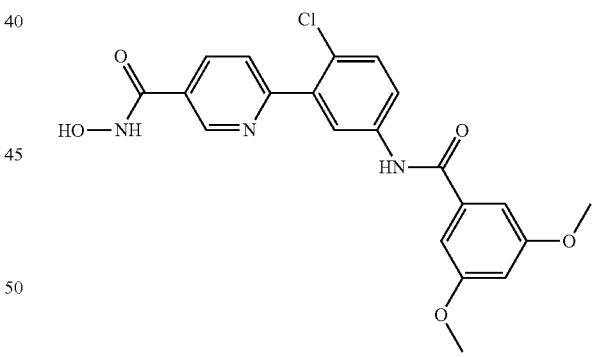

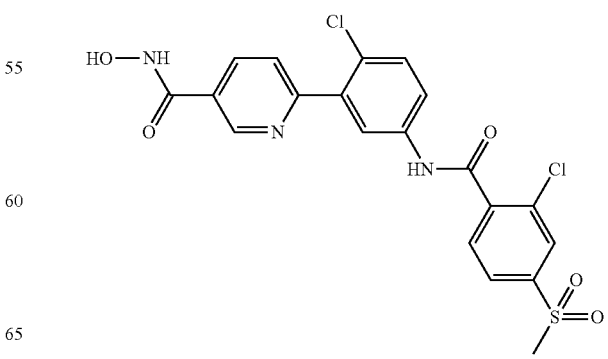

157
-continued
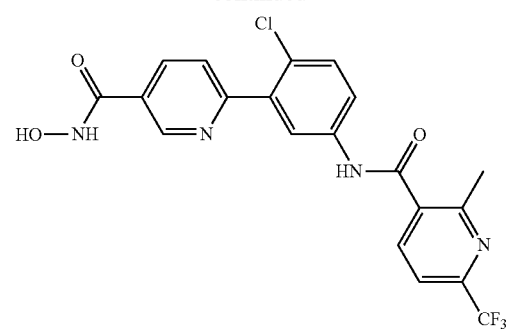
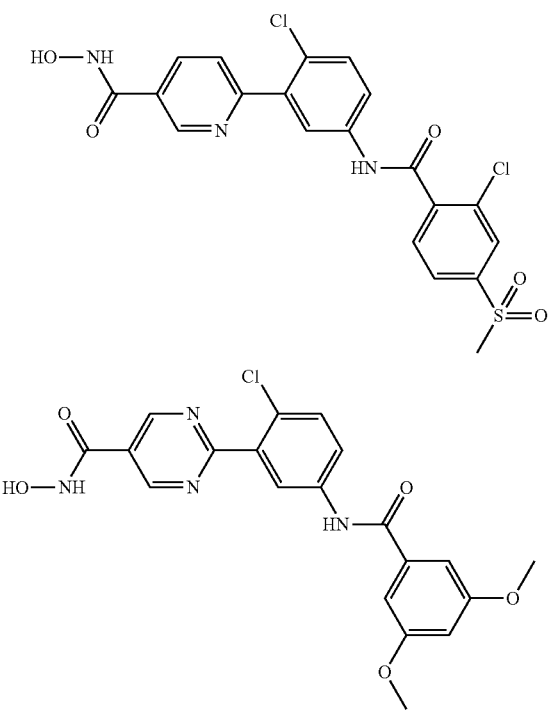
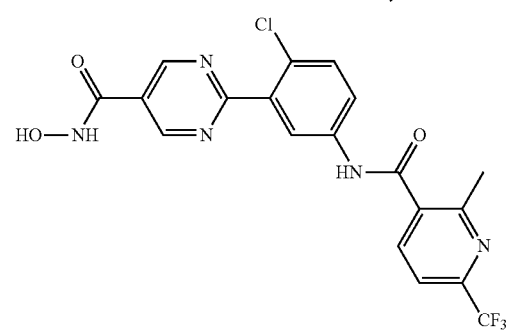
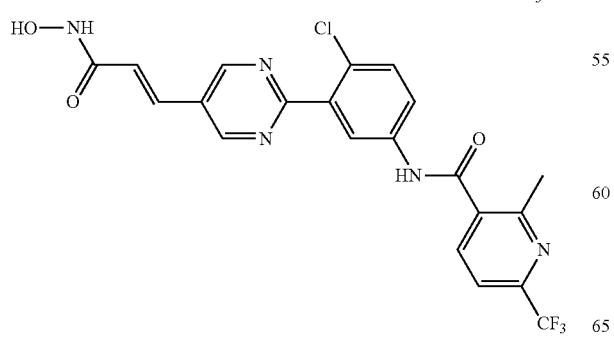
158
-continued
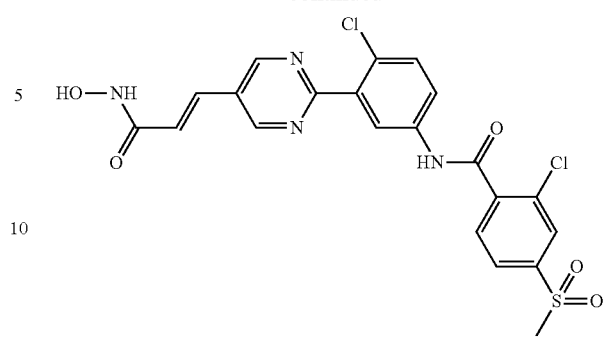
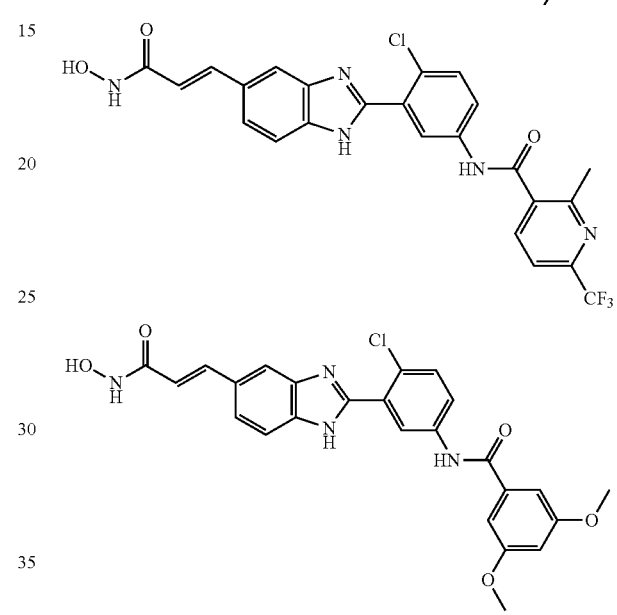
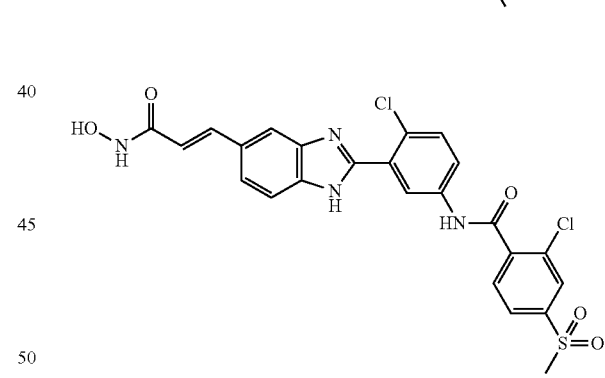
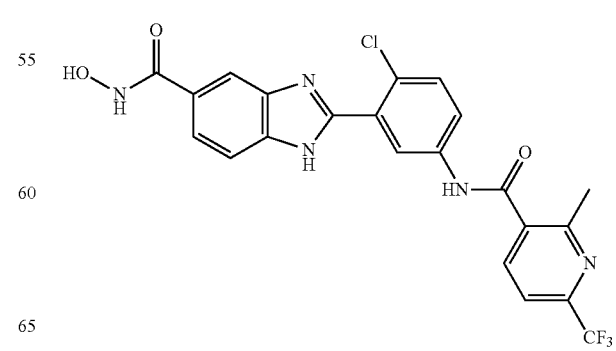

159
-continued
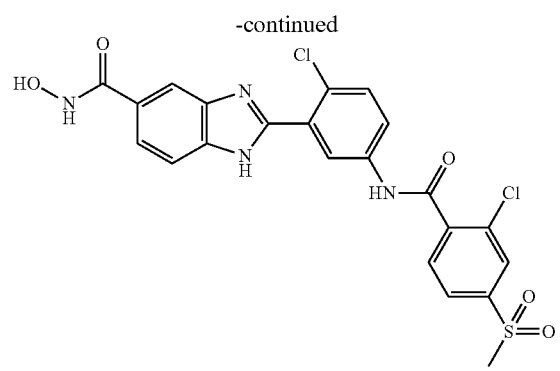
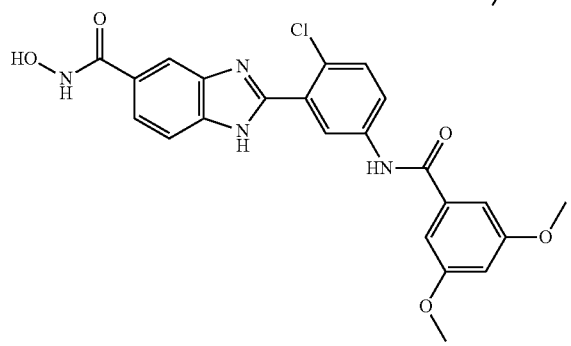
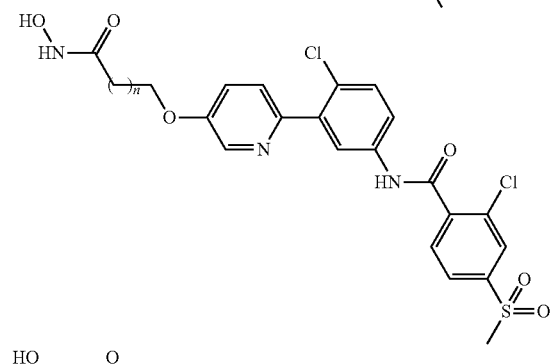
160
-continued
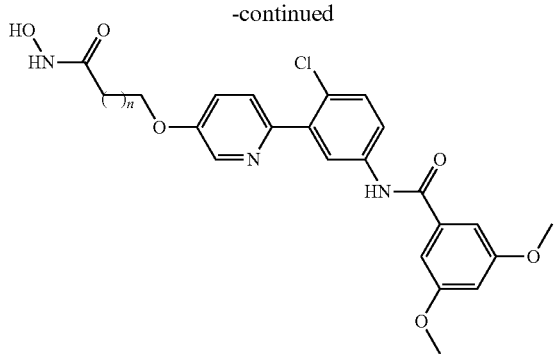
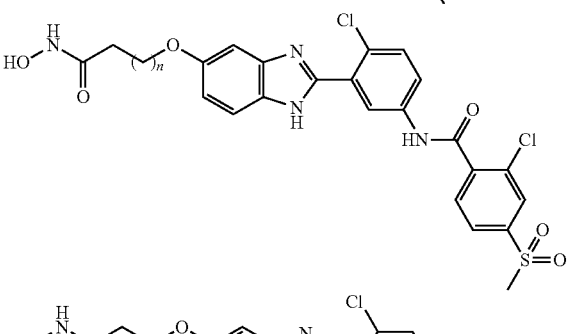
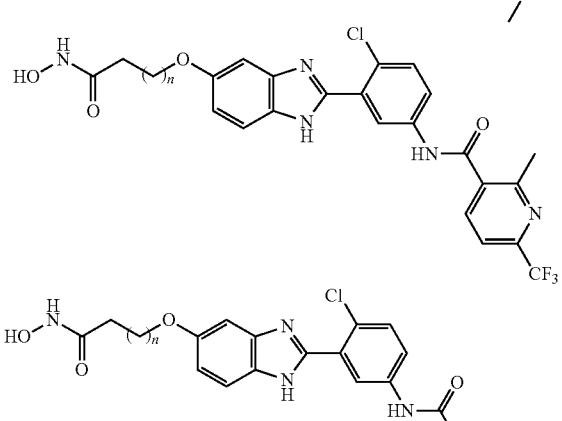
9. The compound of claim 1, wherein B is a direct bond, aryl, heteroaryl, $C_2$-$C_{10}$-alkyl, $C_2$-$C_{10}$-alkenyl, aryl-$C_2$-$C_{10}$-alkyl, aryl-$C_2$-$C_{10}$-alkenyl, aryloxy-$C_1$-$C_{10}$-alkyl, heterocyclylheteroaryl, $C_1$-$C_{10}$-alkylheterocyclylheteroaryl, or $C_1$-$C_{10}$-alkylaminoheteroaryl.
* * * * *

UNITED STATES PATENT AND TRADEMARK OFFICE
CERTIFICATE OF CORRECTION

PATENT NO. : 10,214,514 B2  
APPLICATION NO. : 15/629081  
DATED : February 26, 2019  
INVENTOR(S) : Xiong Cai et al.

Page 1 of 1

It is certified that error appears in the above-identified patent and that said Letters Patent is hereby corrected as shown below:

In the Claims

Column 158, Claim 8, Lines 1-5:

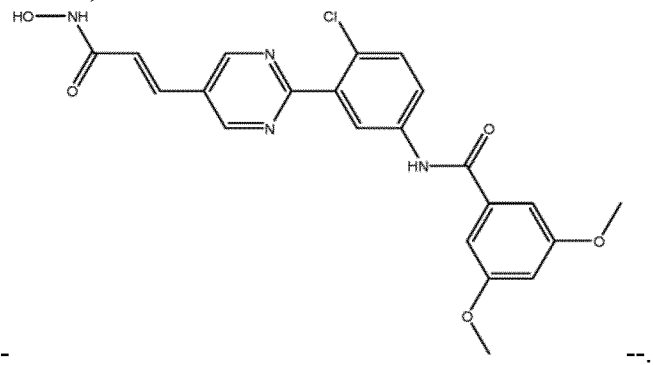

Please insert -- -- .

Signed and Sealed this  
Sixteenth Day of July, 2019

Andrei Iancu  
*Director of the United States Patent and Trademark Office*